(12) United States Patent
Brahmbhatt et al.

(10) Patent No.: US 11,357,860 B2
(45) Date of Patent: *Jun. 14, 2022

(54) TARGETED DELIVERY OF DRUGS, THERAPEUTIC NUCLEIC ACIDS AND FUNCTIONAL NUCLEIC ACIDS TO MAMMALIAN CELLS VIA INTACT KILLED BACTERIAL CELLS

(71) Applicant: EnGeneIC Molecular Deliver Pty Ltd, Sydney (AU)

(72) Inventors: Himanshu Brahmbhatt, Sydney (AU); Jennifer MacDiarmid, Sydney (AU)

(73) Assignee: EngeneIC Molecular Delivery Pty Ltd, Sydney (AU)

( * ) Notice: Subject to any disclaimer, the term of this patent is extended or adjusted under 35 U.S.C. 154(b) by 82 days.

This patent is subject to a terminal disclaimer.

(21) Appl. No.: 15/881,801

(22) Filed: Jan. 28, 2018

(65) Prior Publication Data
US 2018/0250413 A1 Sep. 6, 2018

Related U.S. Application Data

(62) Division of application No. 11/765,635, filed on Jun. 20, 2007, now Pat. No. 9,878,043.

(60) Provisional application No. 60/909,078, filed on Mar. 30, 2007, provisional application No. 60/815,883, filed on Jun. 23, 2006.

(51) Int. Cl.
| | | |
|---|---|---|
| *A61K 47/46* | (2006.01) | |
| *A61K 47/68* | (2017.01) | |
| *A61K 47/69* | (2017.01) | |
| *A61K 31/7088* | (2006.01) | |
| *A61K 31/7105* | (2006.01) | |
| *A61K 31/711* | (2006.01) | |
| *A61K 31/713* | (2006.01) | |
| *A61K 48/00* | (2006.01) | |
| *C07K 16/12* | (2006.01) | |
| *C07K 16/28* | (2006.01) | |
| *A61K 31/337* | (2006.01) | |
| *A61K 31/704* | (2006.01) | |
| *A61K 39/00* | (2006.01) | |

(52) U.S. Cl.
CPC ............ *A61K 47/46* (2013.01); *A61K 31/337* (2013.01); *A61K 31/704* (2013.01); *A61K 31/7088* (2013.01); *A61K 31/711* (2013.01); *A61K 31/713* (2013.01); *A61K 31/7105* (2013.01); *A61K 47/6849* (2017.08); *A61K 47/6901* (2017.08); *A61K 48/0008* (2013.01); *C07K 16/1203* (2013.01); *C07K 16/1235* (2013.01); *C07K 16/2863* (2013.01); *A61K 48/00* (2013.01); *A61K 2039/505* (2013.01); *C07K 2317/31* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 4,975,278 A | 12/1990 | Senter et al. | |
| 4,987,071 A | 1/1991 | Cech et al. | |
| 6,177,083 B1 | 1/2001 | Lubitz | |
| 6,635,448 B2 | 10/2003 | Bucciarelli et al. | |
| 7,011,946 B2 | 3/2006 | Raychaudhuri et al. | |
| 7,125,679 B2 | 10/2006 | Ashkar | |
| 7,183,105 B2 | 2/2007 | Sabbadini et al. | |
| 9,878,043 B2 * | 1/2018 | Brahmbhatt | A61K 31/7088 |
| 2003/0004123 A1 | 1/2003 | Boucher, Jr. et al. | |
| 2004/0198690 A1 | 10/2004 | Satishchandran et al. | |
| 2004/0265994 A1 | 12/2004 | Brahmbhatt et al. | |
| 2005/0222057 A1 | 10/2005 | Brahmbhatt et al. | |
| 2006/0018877 A1 | 1/2006 | Mikazta et al. | |
| 2007/0237744 A1 | 10/2007 | Brahmbhatt et al. | |
| 2007/0241067 A1 | 10/2007 | Brahmbhatt et al. | |
| 2007/0298056 A1 | 12/2007 | Brahmbhatt et al. | |
| 2008/0051469 A1 | 2/2008 | Brahmbhatt et al. | |
| 2008/0299084 A1 | 12/2008 | Brahmbhatt et al. | |

FOREIGN PATENT DOCUMENTS

| | | |
|---|---|---|
| CA | 2 370 714 A1 | 9/2000 |
| DE | 199 09 770 A1 | 3/1999 |
| WO | WO 81/01145 | 4/1981 |
| WO | WO 88/07378 | 10/1988 |
| WO | WO 95/07346 | 3/1995 |

(Continued)

OTHER PUBLICATIONS

Kurreck (Journal of Biomedicine and Biotechnology, vol. 2006, Article ID 83757. pp. 1-7).*

(Continued)

*Primary Examiner* — Patricia Duffy
(74) *Attorney, Agent, or Firm* — Foley & Lardner LLP

(57) ABSTRACT

A composition comprising intact killed bacterial cells that contain a therapeutic nucleic acid, a drug or a functional nucleic acid is useful for targeted delivery to mammalian cells. The targeted delivery optionally employs bispecific ligands, comprising a first arm that carries specificity for a killed bacterial cell surface structure and a second arm that carries specificity for a mammalian cell surface receptor, to target killed bacterial cells to specific mammalian cells and to cause endocytosis of the killed bacterial cells by the mammalian cells. Alternatively, the delivery method exploits the natural ability of phagocytic mammalian cells to engulf killed bacterial cells without the use of bispecific ligands.

19 Claims, 3 Drawing Sheets

(56) References Cited

FOREIGN PATENT DOCUMENTS

| | | |
|---|---|---|
| WO | WO 95/21191 | 8/1995 |
| WO | WO 00/63364 | 10/2000 |
| WO | WO 00/67776 | 11/2000 |
| WO | WO 02/32395 A2 | 4/2002 |
| WO | WO 03/072014 | 9/2003 |
| WO | WO 2005/056749 | 6/2005 |
| WO | WO 2006/066048 | 6/2006 |

OTHER PUBLICATIONS

Shuji Kurane et al., "Targeted Gene Transfer for Adenocarcinoma Using a Combination of Tumor-specific Antibody and Tissue-specific Promoter", Jpn. J. Cancer Res. 89, 1212-1219, Nov. 1998.

Aya Leder et al., "Consequences of Widespread Deregulation of the c-myc Gene in Transgenic Mice: Multiple Neoplasms and Normal Development", Cell, vol. 45, 485-495, May 23, 1986.

Kyung-Dall Lee et al., "Delivery of Macromolecules into Cytosol Using Liposomes Containing Hemolysin from *Listeria monocytogenes*", The Journal of Biological Chemistry, vol. 271, No. 13, Issue of Mar. 29, 1996, pp. 7249-7252.

Che-Hsin Lee et al., "Endostatin gene therapy delivered by *Salmonella choleraesuis* in murine tumor models", The Journal of Gene Medicine, J. Gene Med 2004; 6: 1382-1393.

Che-Hsin Lee et al., "Systemic administration of attenuated *Salmonella choleraesuis* carrying thrombospondin-1 gene leads to tumor-specific transgene expression, delayed tumor growth and prolonged survival in the murine melanoma model", Cancer Gene Therapy (2005) 12, 175-184.

MJ Lemmon et al., "Anaerobic bacteria as a gene delivery system that is controlled by the tumor microenvironment", Gene Therapy (1997), 4, 791-796.

Joanne R. Less et al., "Microvascular Architecture in a Mammary Carcinoma: Branching Patterns and Vessel Dimensions", Cancer Research 51, 265-273, Jan. 1, 1991.

Joanne R. Less et al., "Interstitial Hypertension in Human Breast and Colorectal Tumors", Cancer Research 52, 6371-6374, Nov. 15, 1992.

Joanne R. Less et al., "Rapid Communication Geometric Resistance and Microvascular Network Architecture of Human Colorectal Carcinoma", Microcirculation 1997, vol. 4, No. 1, 25-33.

Emmanuel T. Akporiaye et al., "Clinical aspects of intratumoral gene therapy", Current Opinion in Molecular Therapeutics (1999) 1(4):443-453.

Suresh V. Ambudkar et al., "Biochemical, Cellular, and Pharmacological Aspects of the Multidrug Transporter", Annu. Rev. Pharmacol. Toxicol. 1999, 39:361-398.

Raj K. Batra et al., "Receptor-mediated gene delivery employing lectin-binding specificity", Gene Therapy (1994) 1, 255-260.

Christian M. Becker et al., "Gene Therapy of Prostate Cancer with the Soluble Vascular Endothelial Growth Factor Receptor Flk1", Cancer Biology & Therapy, 1:5, 548-553, Sep./Oct. 2002.

Anne Blangy et al., "Phosphorylation by p34$^{cdc2}$ Regulates Spindle Association of Human Eg5, a Kinesin-Related Motor Essential for Bipolar Spindle Formation in Vivo", Cell, vol. 83, pp. 1159-1169, Dec. 29, 1995.

Per A. Bullough et al., "Structure of influenza haemagglutinin at the pH of membrane fusion", Nature, vol. 371, Sep. 1, 1995, pp. 37-43.

Natasha J. Caplen, "RNAi as a gene therapy approach", Expert Opin. Biol. Ther. (2003 3(4) 575-586.

Natasha J. Caplen et al., "Short Interfering RNA (siRNA)—Mediated RNA Interference (RNAi) in Human Cells", Ann. N.Y. Acad. Sci. 1002: 56-62 (2003).

Paul Carter, "Improving the Efficacy of Antibody-Based Cancer Therapies", Natures Review vol. 1, Nov. 2001, pp. 118-129.

Gennaro Ciliberto et al., "Cell-Specific Expression of a Transfected Human $\alpha_1$-Antitrypsin Gene", Cell vol. 41, 531-540, Jun. 1985.

Li Mei Chen et al., "*Salmonella* spp. Are cytotoxic for cultured macrophages", Molecular Microbiology (1996) 21(5), 1101-1115.

D. Chen et al., "Adaptive and innate immune responses to gene transfer vectors: role of cytokines and chemokines in vector function", Gene Therapy (2003) 10, 991-998.

Paul R. Clark et al., "Cationic lipid-mediated gene transfer: Current concepts", Current Opinion in Molecular Therapeutics 1999 1(2): 158-176.

Richard A. Collins et al., "Reaction Conditions and Kinetics of Self-Cleavage of a Ribozyme Derived from *Neurospora* VS RNA", Biochemistry, 1993, 32, pp. 2795-2799.

Tyler J. Curiel et al., "Long-Term Inhibition of Clinical and Laboratory Human Immunodeficiency Virus Strains in Human T-Cell Lines Containing an HIV-Regulated Diphtheria Toxin A Chain Gene", Human Gene Therapy 4:741-747 (1993).

E.M. Dagenbach et al., "Erratum", J. Cell Sci. 117, (2004) 3-7.

Long H. Dang et al., "Combination bacteriolytic therapy for the treatment of experimental tumors", PNAS Dec. 18, 2001, vol. 98, No. 26, pp. 15155-15160.

Hans J. De Haard et al., "A Large Non-immunized Human Fab Fragment Phage Library That Permits Rapid Isolation and Kinetic Analysis of High Affinity Antibodies", The Journal of Biological Chemistry, vol. 274, No. 26, Issue of Jun. 25, 1999, pp. 18218-18230.

G. De Jong et al., "Efficient in-vitro transfer of a 60-Mb mammalian artificial chromosome into murine and hamster cells using cationic lipids and dendrimers", Chromosome Research, 9: 475-485, 2001.

Martin M. Dinges et al., "HIV-Regulated Diphtheria Toxin A Chain Gene Confers Long-Term Protection Against HIV Type 1 Infection in the Human Promonocytic Cell Line U937", Human Gene Therapy: 6:1437-1445, Nov. 1995.

Steven W. Dow et al., "Lipid-DNA Complexes Induce Potent Activation of Innate Immune Responses and Antitumor Activity When Administered Intravenously", The Journal of Immunology 1999, 163:1552-1561.

S. Dramsi et al., "Intracellular Pathogens and the Actin Cytoskeleton", Annu. Rev. Cell Dev. Biol. 1998, 14: 137-166.

Rakesh K. Jain, "Delivery of molecular and cellular medicine to solid tumors", Advanced Drug Delivery Reviews 46 (2001) 149-168.

Molly B. James et al., "Nuclear-Associated Plasmid, but Not Cell-Associated Plasmid, is Correlated with Transgene Expression in Cultured Mammalian Cells", Molecular Therapy, vol. 1, No. 4, Apr. 2000, pp. 339-346.

Peter T. Jones et al., "Replacing the complementarity-determining regions in a human antibody with those from a mouse", Nature, vol. 321, May 29, 1986, pp. 522-525.

C.S. Kaetzel et al., "The Polymeric Immunoglobulin Receptor: structure and synthesis", Immunoglobulins and Mechanisms of Mucosal Immunity, BCSTB5 25(2) (1997), pp. 475-480.

M. Kanke et al., "Interaction of Microspheres with Blood Constituents: I. Uptake of Polystyrene Spheres by Monocytes and Granulocytes and Effect on Immune Responsiveness of Lymphocytes", Journal of Parenteral Science and Technology, vol. 37, No. 6, Nov.-Dec. 1983, pp. 210-217.

Tarun M. Kapoor et al., "Probing Spindle Assembly Mechanisms with Monastrol, a Small Molecule Inhibitor of the Mitotic Kinesin, Eg5", The Journal of Cell Biology, vol. 150, No. 5; Sep. 4, 2000, pp. 975-988.

Boris Karpovsky et al., "Production of Target-Specific Effector Cells Using Hetero-Cross-Linked Aggregates Containing Anti-Target Cell and Anti-Fcγ Receptor Antibodies", Journal of Experimental Medicine, vol. 160, Dec. 1984, 1686-1701.

Maha M. Katabi et al., "Hexokinase Type II: A Novel Tumor-Specific Promoter for Gene-Targeted Therapy Differentially Expressed and Regulated in Human Cancer Cells", Human Gene Therapy, 10:155-164 Jan. 20, 1999.

Gavin D. Kelsey et al., "Species- and tissue-specific expression of human $\alpha_1$antitrypsin in transgenic mice", Genes and Development 1:161-171, 1987.

Bat-Sheva Kerem et al., "Identification of the Cystic Fibrosis Gene: Genetic Analysis", Science, Sep. 8, 1989, vol. 245, pp. 1073-1080.

Ivan King et al., "Tumor-Targeted Salmonella Expressing Cytosine Deaminase as an Anticancer Agent", Human Gene Therapy 13:1225-1233 (Jul. 1, 2002).

(56) References Cited

OTHER PUBLICATIONS

Jorg Kleeff et al., "Targeting of suicide gene delivery in pancreatic cancer cells via FGF receptors", Cancer Gene Therapy (2002) 9, 522-532.
Ann R. Klemm et al., "Effects of Polyethyleneimine on Endocytosis and Lysosome Stability", Biochemical Pharmacology, vol. 56, pp. 41-46, 1998.
Achim Knappik et al., "Fully Synthetic Human Combinatorial Antibody Libraries (HuCAL) Based on Modular Consensus Frameworks and CDRs Randomized with Trinucleotides" J. Mol. Biol. (2000), 296, pp. 57-86.
M.A. Konerding et al., "Microvascular Corrosion Casting in the Study of Tumor Vascularity: A Review", Scanning Microscopy, vol. 9, No. 4, 1995, pp. 1233-1244.
Sheri A.Kostelny et al., "Formation of a Bispecific Antibody By the Use of Leucine Zippers", The Journal of Immunology, vol. 148, No. 5, Mar. 1, 1992, pp. 1547-1553.
Patrick Kreiss et al., "Plasmid DNA size does not affect the physicochemical properties of lipoplexes but modulates gene transfer efficiency", Nucleic Acids Research, 1999, vol. 27, No. 19, pp. 3792-3798.
Tohru Hoshida et al., "Gene Therapy for Pancreatic Cancer Using an Adenovirus Vector Encoding Soluble flt-1 Vascular Endothelial Growth Factor Receptor", Pancreas, vol. 25, No. 2, pp. 111-121, 2002.
Shi-zhen Hu et al., "Minibody: A Novel Engineered Anti-Carcinoembryonic Antigen Antibody Fragment (Single-Chain Fv-$C_H3$) Which Exhibits Rapid, High-Level Targeting of Xenografts", Cancer Research 56, 3055-3061, Jul. 1, 1996.
Christelle Souriau et al., "Recombinant antibodies for cancer diagnosis and therapy", Expert. Opin. Biol. Ther. (2001) 1(5):845-855.
Peter J. Hudson et al., "Engineered antibodies", Nature Medicine, vol. 9, No. 1, Jan. 2003, pp. 129-134.
M.C. Hung et al., "Development of Clinical Trial of E1A Gene Therapy Targeting HER-2lneu-Overexpressing Breast and Ovarian Cancer", Cancer Gene Therapy: Past Achievements and Future Challenges, 2000, pp. 171-180.
Rakesh K.Jain, "Transport of Molecules Across Tumor Vasculature", Cancer and Metastasis Reviews 6: 559-593 (1987).
Rakesh K. Jain, "Delivery of Molecular Medicine to Solid Tumors", Science, vol. 271, Feb. 23, 1996, pp. 1079-1080.
Rakesh K. Jain, "Delivery of Molecular and Cellular Medicine to Solid Tumors", Microcirculation, 1997, vol. 4, No. 1, 1-23.
Rakesh K. Jain "Delivery of Molecular and Cellular Medicine to Solid Tumors", Journal of Controlled Release, 53 (1998) 49-67.
Urs F. Greber et al., "The role of the adenovirus protease in virus entry into cells", The EMBO Journal vol. 15, No. 8, pp. 1766-1777, 1996.
Nicola K. Green et al., "Adenoviral vectors: Systemic delivery and tumor targeting", Cancer Gene Therapy (2002) 9, pp. 1036-1042.
Andrew D. Griffiths et al., "Isolation of high affinity human antibodies directly from large synthetic repertoires", The EMBO Journal, vol. 13, No. 14, pp. 3245-3260, 1994.
Cecilia Guerrier-Takada et al., "The RNA Moiety of Ribonuclease P is the Catalytic Subunit of the Enzyme", Cell, vol. 35, 849-857, Dec. 1983.
Im Hafez et al., "On the mechanism whereby cationic lipids promote intracellular delivery of polynucleic acids", Gene Therapy (2001) 8, 1188-1196.
Arnold Hampel et al., "RNA Catalytic Properties of the Minimum (−)sTRSV Sequence", Biochemistry, 1989, 28, pp. 4929-4933.
Douglas Hanahan, "Heritable formation of pancreatic β-cell tumours in transgenic mice expressing recombinant insulin/simian virus 40 oncogenes", Nature, vol. 315, May 9, 1985, 115-122.
Gail Singer Harrison et al., "Inhibition of Human Immunodeficiency Virus-1 Production Resulting from Transduction with a Retrovirus Containing an HIV-Regulated Diptheria Toxin A Chain Gene", Human Gene Therapy, 3: 461-469 (1992).

Ian R. Hart, "Tissue Specific Promoters in Targeting Systemically Delivered Gene Therapy", Seminars in Oncology, vol. 23, No. 1, Feb. 1996, pp. 154-158.
Roger Heim et al., "Wavelength mutations and posttranslational autoxidation of green fluorescent protein", Proc. Natl. Acad. Sci. USA vol. 91, pp. 12501-12504, Dec. 1994.
Susan H. Hobbs et al., "Regulation of transport pathways in tumor vessels: Role of tumor type and microenvironment", Proc. Natl. Acad. Sci. USA vol. 95, pp. 4607-4612, 1998.
Zhenfeng Duan et al., "Inhibition of ABCB1 (MDR1) and ABCB4 (MDR3) expression by small interfering RNA and reversal of paclitaxel resistance in human ovarian cancer cells", Molecular Cancer Therapeutics, 2004:3(7), 833-838.
S. Dübel et al., "Bifunctional and multimeric complexes of streptavidin fused to single chain antibodies (scFv)", Journal of Immunological Methods, 178(1995)201-209.
Stephen P. Dunham, "The application of nucleic acid vaccines in veterinary medicine", Research in Veterinary Science, 2002, 73, 9-16.
Mark S. Duxbury et al., "siRNA Directed Against c-Src Enhances Pancreatic Adenocarcinoma Cell Gemcitabine Chemosensitivity", J. Am. Coll. Surg. Jun. 2004; vol. 198, No. 6; 953-959.
A. El Ouahabi et al., "The role of endosome destabilizing activity in the gene transfer process mediated by cationic lipids", FEBS Letters, 414, (1997) 187-192.
Annmarie Pallone Enos et al., "Mutation of a Gene That Encodes a Kinesin-like Protein Blocks Nuclear Division in A. nidulans". Cell vol. 60, 1019-1027, Mar. 23, 1990.
Karim Essani et al., "Biogenesis of Vaccinia: Evidence for More than 100 Polypeptides in the Virion", Virology 95, 385-394 (1979).
Hassan Farhood et al., "The role of dioleoyl phosphatidylethanolamine in cationic liposome mediated gene transfer", Biochimica et Biophysica Acta 1235 (1995) 289-295.
A. Fasbender et al., "Effect of co-lipids in enhancing cationic lipid-mediated gene transfer in vitro and in vivo", Gene Therapy (1997) 4, 716-725.
P.L. Felgner et al., "Cationic liposome-mediated transfection", Nature, vol. 337, Jan. 26, 1989, pp. 387-388.
S. Ferrari et al., "Immunological hurdles to lung gene therapy", Clin. Exp. Immunol. 2003, 132:1-8.
B. Brett Finlay et al., "Exploitation of Mammalian Host Cell Functions by Bacterial Pathogens", Science vol. 276, May 2, 1997, pp. 718-725.
Me Fox et al., "Anaerobic bacteria as a delivery system for cancer gene therapy: in vitro activation of 5-fluorocytosine by genetically engineered clostridia", Gene Therapy (1996) 3, 173-178.
Monique Frain et al., "Binding of a Liver-Specific Factor to the Human Albumin Gene Promoter and Enhancer", Molecular and Cellular Biology, vol. 10, No. 3, Mar. 1990, pp. 991-999.
J.E. Galan, "Molecular and Cellular Bases of *Salmonella* Entry into Host Cells", Bacterial Invasiveness, 1996, 43-60.
Huajian Gao et al., "Mechanics of receptor-mediated endocytosis", PNAS Jul. 5, 2005, vol. 102, No. 27, pp. 9469-9474.
Leonard E. Gerlowski et al., "Microvascular Permeability of Normal and Neoplastic Tissues", Microvascular Research, 31, 288-305, 1986.
Martine J. Glennie et al., "Preparation and Performance of Bispecific F(ab'γ)$_2$ Antibody Containing Thioether-Linked Fab'γ Fragments", The Journal of Immunology vol. 139, No. 7, Oct. 1, 1987, pp. 2367-2375.
Michael A. Gosselin et al., "Folate receptor-targeted liposomes as vectors for therapeutic agents", Biotechnology Annual Review, vol. 8, 2002, pp. 103-131.
Xi Li et al., "Bifidobacterium adolescentis as a delivery system of endostatin for cancer gene therapy: Selective inhibitor of angiogenesis and hypoxic tumor growth", Cancer Gene Therapy (2003) 10, 105-111.
Q. Liu et al., "Molecular basis of the inflammatory response to adenovirus vectors", Gene Therapy (2003) 10, 935-940.
S-C Liu et al., "Anticancer efficacy of systemically delivered anaerobic bacteria as gene therapy vectors targeting tumor hypoxia/necrosis", Gene Therapy (2002) 9, 291-296.

(56) References Cited

OTHER PUBLICATIONS

Gretchen L. Lorenzi et al., "Enhanced plasmid DNA delivery using anionic LPDII by listeriolysin O incorporation", The Journal of Gene Medicine, 2005, 7, 1077-1085.
K. Brooks Low et al., "Lipid A mutant *Salmonella* with suppressed virulence and TNFα Induction retain tumor-targeting in vivo", Nature Biotechnology vol. 17, Jan. 1999, pp. 37-41.
Xiang Luo et al., "Antitumor Effect of VNP20009, an Attenuated *Salmonella*, in Murine Tumor Models", Oncology Research, vol. 12, 2001, pp. 501-508.
Raymond J. MacDonald, "Expression of the Pancreatic Elastase I Gene in Transgenic Mice", Hepatology, vol. 7, No. 1, pp. 42S-51S, 1987.
Hiroshi Maeda, "The Enhanced Permeability and Retention (EPR) Effect in Tumor Vasculature: The Key Role of Tumor-Selective Macromolecular Drug Targeting", Advan. Enzyme Regul. vol. 41, pp. 189-207, 2001.
Hiroshi Maeda et al., "Tumoritropic and Lymphotropic Principles of Macromolecular Drugs",. Critical Reviews in Therapeutic Drug Carrier Systems, vol. 6, Issue 3, 1989, pp. 193-210.
Mark Marsh et al., "Virus Entry into Animal Cells", Advances in Virus Research, vol. 36, 1989, pp. 107-151.
John Marshall, "Carcinoembryonic Antigen-Based Vaccines", Seminars in Oncology, vol. 30, No. 3, Suppl. 8, Jun. 2003, pp. 30-36.
Anthony J. Mason et al., "The Hypogonadal Mouse: Reproductive Functions Restored by Gene Therapy", Science, vol. 234, Dec. 12, 1986, pp. 1372-1378.
Thomas U Mayer et al., "Small Molecule Inhibitor of Mitotic Spindle Bipolarity Identified in a Phenotype-Based Screen", Science, vol. 286, Oct. 29, 1999, pp. 971-974.
Robert Menard et al., "Bacterial entry into epithelial cells: the paradign of *Shigella*", Trends in Microbiology vol. 4, No. 6, Jun. 1996, pp. 220-226.
Kathleen B. Meyer et al., "Manipulating the Intracellular Trafficking of Nucleic Acids", Gene Therapy for Diseases of the Lung, 1997, pp. 135-180.
Nigel P. Minton et al., "Chemotherapeutic tumour targeting using clostridial spored", FEMS Microbiology Reviews 17 (1995) 357-364.
Denise M. Monack et al., "*Salmonella typhimurium* invasion induces apoptosis in infected macrophages", Proc. Natl. Acad. Sci. USA, vol. 93, pp. 9833-9838, Sep. 1996.
Christopher L. Morton et al., "Rhabdomyosarcoma-Specific Expression of the Herpes Simplex Virus Thymidine Kinase Gene Confers Sensitivity to Ganciclovir", The Journal of Pharmacology and Experimental Therapeutics, vol. 286, No. 2, 1998, pp. 1066-1073.
B. Mui et al., "Membrane perturbation and the mechanism of lipid-mediated transfer of DNA into cells", Biochimica et Biophysica Acta 1467 (2000) pp. 281-292.
Takashi Nakai et al., "Remarkably Size-Regulated Cell Invasion by Artificial Viruses. Saccharide-Dependent Self-Aggregation of Glycoviruses and Its Consequences in Glycoviral Gene Delivery", J. Am. Chem. Soc., 2003, pp. 8465-8475.
Dirk M. Nettelbeck et al., "Targeting of Adenovirus to Endothelial Cells by a Bispecific Single-Chain Diabody Directed against the Adenovirus Fiber Knob Domain and Human Endoglin (CD105)", Molecular Therapy, vol. 3, No. 6, Jun. 2001, pp. 882-891.
Christiane Nieth et al., "Modulation of the classical multidrug resistance (MDR) phenotype by RNA interference (RNAi)", FEBS Letters 545 (2003) 144-150.
S. Nuyts et al., "Clostridium spores for tumor-specific drug delivery", Anti-Cancer Drugs 2002, 13, pp. 115-125.
S. Nuyts et al., "Radio-responsive recA promoter significantly increases TNFα production in recombinant Clostridia after 2 Gy irradiation", Gene Therapy (2001) 8, 1197-1201.
Manfred Ogris et al., "Targeting tumors with non-viral gene delivery system", Drug Discovery Today, vol. 7, No. 8, Apr. 2002, pp. 479-485.
Fumio Osaki et al., "A Quantum Dot Conjugated Sugar Ball and Its Cellular Uptake. On the Size Effects of Endocytosis in the Subviral Region", J. Am. Chem. Soc. 2004, 126, pp. 6520-6521.
Fan Yuan et al., "Microvascular Permeability and Interstitial Penetration of Sterically Stabilized (Stealth) Liposomes in a Human Tumor Xenograft", Cancer Research 54, Jul. 1, 1994, pp. 3352-3356.
Fan Yuan et al., "Vascular Permeability in a Human Tumor Xenograft: Molecular Size Dependent and Cutoff Size", Cancer Research 55, Sep. 1, 1995, pp. 3752-3756.
Li Yuhua et al., "Oral Cytokine Gene Therapy Against Murine Tumor Using Attenuated *Salmonella typhimurium*", Int. J. Cancer: 94, 438-443 (2001).
Olivier Zelphati et al., "Intracellular Distribution and Mechanism of Delivery of Oligonucleotides Mediated by Cationic Lipids", Pharmaceutical Research vol. 13, No. 9, 1996, pp. 1367-1372.
Olivier Zelphati et al., "Mechanism of oligonucleitde release from cationic liposomes", Proc. Natl. Acad. Sci. USA vol. 93, pp. 11493-11498, Oct. 1996.
Yi Zhao et al., "Identification of the block in targeted retroviral-mediated gene transfer", Proc. Natl. Acad. Sci. USA, vol. 96, pp. 4005-4010, Mar. 1999.
Xin Zhou et al., "*Salmonella typhimurium* Induces Apoptosis in Human Monocyte-Derived Macrophages", Microbial. Immunol. 44(12), 987-995, 2000.
Assem-Galal Ziady et al., "Gene transfer into hepatoma cell lines via the serpin enzyme complex receptor", The American Physiological Society, 1997, pp. G545-G552.
Mark M. Whitmore et al., "Systemic administration of LPD prepared with CpG oligonucleotides inhibits the growth of established pulmonary metastases by stimulating innate and acquired antitumor immune responses", Cancer Immunol. Immunother. (2001) 50: 503-514.
Thomas J. Wickham et al., "Targeted Adenovirus Gene Transfer to Endothelial and Smooth Muscle Cells by Using Bispecific Antibodies", Journal of Virology, vol. 70, No. 10, Oct. 1996, pp. 6831-6838.
Samuel D. Wright et al., "Interferon-γ Depresses Binding of Ligand By C3b and C3bi Receptors on Cultured Human Monocytes, an Effect Reversed By Fibronectin", J. Exp. Med. vol. 163, May 1986, pp. 1245-1259.
Iwona Wrobel et al., "Fusion of cationic liposomes with mammalian cells occurs after endocytosis", Biochimica et Biophysica Acta 1235 (1995) 296-304.
Hao Wu et al., "Small Interfering RNA-Induced Suppression of MDR1 (P-Glycoprotein) Restores Sensitivity to Multidrug-resistant Cancer Cells", Cancer Research 63, 1515-1519, Apr. 1, 2003.
Yuhong Xu et al., "Mechanism of DNA Release from Cationic Liposome/DNA Complexes Used in Cell Transfection", Biochemistry 1996, 35, pp. 5616-5623.
E. Yague et al., "Complete reversal of multidrug resistance by stable expression of small interfering RNAs targeting MDR1 ", Gene Therapy 2004, 11, 1170-1174.
Hiroshi Yamada et al., "Murine IL-2 Secreting Recombinant Bacillus Calmette-Guérin Augments Macrophage-Mediated Cytotoxicity Against Murine Bladder Cancer MBT-2", The Journal of Urology, vol. 164, 526-531, Aug. 2000.
Kazuyuki Yazawa et al., "*Bifidobacterium longum* as a delivery system for cancer gene therapy: Selective localization and growth in hypoxic tumors", Cancer Gene Therapy, vol. 7, No. 2, 2000: pp. 269-274.
Kazuyuki Yazawa et al., "Bifidobacterium longum as a delivery system for gene therapy of chemically induced rat mammary tumors", Breast Cancer Research and Treatment 66: 165-170, 2001.
Kazuyuki Yazawa M.D et al., "Current Progress in Suicide Gene Therapy for Cancer", World J. Surg. 26, 783-789, 2002.
Nelson S. Yew et al., "Contribution of Plasmid DNA to Inflammation in the Lung after Administration of Cationic Lipid:pDNA Complexes", Human Gene Therapy, 10:223-234, Jan. 20, 1999.
Yong A. Yu et al., "Visualization of tumors and metastases in live animals with bacteria and vaccinia virus encoding light-emitting proteins", Nature Biotechnology, vol. 22, No. 3, Mar. 2004, pp. 313-320.

(56) References Cited

OTHER PUBLICATIONS

Aneta Todorovska et al., "Design and application of diabodies, triabodies and tetrabodies for cancer targeting", Journal of Immunological Methods 248(2001) 47-66.
Ian Tomlinson et al., "[28] Methods for Generating Multivalent and Bispecific Antibody Fragments", Methods in Enzymology, vol. 326, 2000, pp. 461-479.
Tristan J. Vaughan et al., "Human Antibodies with Sub-nanomolar Affinities Isolated from a Large Non-immunized Phage Display Library", Nature Biotechnology vol. 14, Mar. 1996, pp. 309-314.
Martine Verhoeyen et al., "Reshaping Human Antibodies: Grafting an Antilysozyme Activity", Science, vol. 239, pp. 1534-1536.
H. Wakimoto et al., "Effects of innate immunity on herpes simplex virus and its ability to kill tumor cells", Gene Therapy, (2003) 10, 983-990.
Robert Wattiaux et al., "Endosomes, lysosomes: their implication in gene transfer", Advanced Drug Delivery Reviews 41, (2000) 201-208.
Siegfried Weiss et al., "Tranfer of eukaryotic expression plasmids to mammalian host cells by bacterial carriers", Current Opinion in Biotechnology 2001, 12: 467-472.
M. Whitmore et al., "LPD lipopolyplex initiates a potent cytokine response and inhibits tumor growth", Gene Therapy (1999) 6, 1867-1875.
Kirsten Sandvig et al., "Endocytosis without clathrin", Trends in Cell Biology, vol. 4, Aug. 1994, pp. 275-277.
Barry J. Seville et al., "A Site-Specific Self-Cleavage Reaction Performed by a Novel RNA in Neurospora Mitochondria", Cell, vol. 61, 685-696, May 18, 1990.
Barry J. Saville et al., "RNA-mediated ligation of self-cleavage products of a Nuerospora mitochondrial plasmid transcript", Proc. Natl. Acad. Sci. USA vol. 88, pp. 8826-8830, Oct. 1991.
Ronald K. Scheule, "The role of CpG motifs in immunostimulation and gene therapy", Advanced Drug Delivery Reviews 44 (2000) 119-134.
Prem Seth et al., "Binding of Adenovirus and Its External Proteins to Triton X-114", The Journal of Biological Chemistry, vol. 260, No. 27, pp. 14431-14434, Issue of Nov. 25, 1985.
N.D. Sonawane et al., "Chlopride Accumulation and Swelling in Endosomes Enhances DNA Transfer by Polyamine DNA Polyplexes", The Journal of Biological Chemistry, vol. 278, No. 45, Issue of Nov. 7, 2003, pp. 44826-44831.
David P. Speert et al., "Functional Characterization of Microphage Receptors for in Vitro Phagocytosis of Unopsonized *Pseudomonas aeruginosa*", J. Clin. Invest. vol. 82, Sep. 1988, 872-879.
David M. Spencer, "Developments in suicide genes for preclinical and clinical applications", Current Opinions in Molecular Therapeutics (2000) 2(4) 433-440.
Barry S. Stein et al., "pH-lndependent HIV Entry into CD4-Positive T Cells via Virus Envelope Fusion to the Plasma Membrane", Cell., vol. 49, 659-668, Jun. 5, 1987.
Richard J. Stockert, "The Asialoglycoprotein Receptor: Relationships Between Structure, Function and Expression", Physiological Reviews, vol. 75, No. 3, Jul. 1995, pp. 591-609.
Joel A. Swanson et al., "Macropinocytosis", Trends in Cell Biology, vol. 5, Nov. 5, 1995, pp. 424-428.
Galvin H. Swift et al., "Tissue-Specific Expression of the Rat Pancreatic Elastase I Gene in Transgenic Mice", Cell, vol. 38, 639-646, Oct. 1984.
Yasuhiko Tabata et al., "Macrophage phagocytosis of biodegradable microspheres composed of L-lactic acid/glycolic acid homo- and copolymers", Journal of Biomedical Materials Research, vol. 22, 837-858, 1988.
Rieko Tachibana et al., "Quantitative Analysis of Correlation between Number of Nuclear Plasmids and Gene Expression Activity After Transfection with Cationic Liposomes", Pharmaceutical Research vol. 19, No. 4, Apr. 2002, pp. 377-381.

Weikang Tao et al., "Induction of apoptosis by an inhibitor of the mitotic kinesin KSP requires both activation of the spindle assembly checkpoint and mitotic slippage", Cancer Cell, Jul. 2005, vol. 8, pp. 49-59.
Jan Theys et al., "Specific targeting of cytosine deaminase to solid tumors by engineered *Clostridium acetobutylicum*", Cancer Gene Therapy, vol. 8, No. 4, 2001: pp. 294-297.
Martin Thurnher et al., "Carbohydrate receptor-mediated gene transfer to human T leukaemic cells", Glycobiology vol. 4, No. 4, pp. 429-435, 1994.
Jane Osbourn et al., "Current methods for the generation of human antibodies for the treatment of autoimmune diseases", DDT vol. 8, No. 18, Sep. 2003, pp. 845-851.
Peter Pack et al., "Miniantibodies: Use of Amphipathic Helices to Produce Functional Flexibly Linked Dimeric $F_v$Fragments with High Avidity in *Escherichia coli*", Biochemistry, vol. 31, No. 6, Feb. 18, 1992, pp. 1579-1584.
P. Paglia et al., "In vivo correction of genetic defects of monocyte/ macrophages using attenuated *Salmonella* as oral vectors for targeted gene delivery", Gene Therapy, (2000) 7, 1725-1730.
John M. Pawelek et al., "Tumor-targeted *Salmonella* as a Novel Anticancer Vector", Cancer Research 57, pp. 4537-4544, Oct. 15, 1997.
John M. Pawelek et al., "Bacteria as tumour-targeting vectors", The Lancet Oncology vol. 4, Sep. 2003, pp. 548-556.
Anne T. Perrotta et al., "Cleavage of Oligoribonucleotides by a Ribozyme Derives from the Hepatitis 6 Virus RNA Sequence", Biochemistry 1992, 31, 16-21.
Hans-Inge Peterson et al., "Tumour Vessel Permeability and Transcapillary Exchange of Large Molecules of Different Size", $9^{th}$ Europ. Conf. Microcirculation, Antwerp 1976, Bibl. Anat. No. 15, pp. 262-265.
Jacquelien C. Pikaar et al., "Opsonic Activities of Surfactant Proteins A and D in Phagocytosis of Gram-Negative Bacteria by Alveolar Macrophages", The Journal of Infectious Diseases, 1995, 172:481-489.
Carl A. Pinkert et al., "An albumin enhancer located 10 kb upstream functions along with its promoter to direct efficient, liver-specific expression in transgenic mice", Genes & Development 1:268-276, 1987.
J. Platt et al., "Antitumour effects of genetically engineered *Salmonella* in combination with radiation", European Journal of Cancer 36 (2000) 2397-2402.
Douglas C. Prasher, "Using GFP to see the light", TIP Aug. 1995, vol. 11, No. 8, pp. 320-323.
Jack A. Ragheb et al., "Inhibition of Human Immundeficiency Virus Type 1 by Tat/Rev-Regulated Expression of Cytosine Deaminase Interferon α2, or Diphtheria Toxin Compared with Inhibition by Transdominant Rev", Human Gene Therapy 10:103-112, Jan. 1, 1999.
Carol Readhead et al., "Expression of a Myelin Basic Protein Gene in Transgenic Shiverer Mice: Correction of the Dysmyelinating Phenotype", Cell, vol. 48, 703-712, Feb. 27, 1987.
John B.B. Ridgway et al., "Knobs-into-holes engineering of antibody $C_H3$ domains for heavy chain heterodimerization", Protein Engineering vol. 9, No. 7, pp. 617-621, 1996.
Lutz Riechmann et al., "Reshaping human antibodies for therapy", Nature, vol. 332, Mar. 24, 1988, pp. 323-327.
Howard Riezman, "Three clathrin-dependent budding steps and cell polarity", Trends in Cell Biology, vol. 3, Oct. 1993, pp. 330-332.
John R. Riordan et al., "Identification of the Cystic Fibrosis Gene: Cloning and Characterization of Complementary DNA", Science vol. 245, pp. 1066-1073, Sep. 8, 1989.
Johanna M. Rommens et al., "Identification of the Cystic Fibrosis Gene: Chromosome Walking and Jumping", Research Articles, Science vol. 245; Sep. 8, 1989, pp. 1059-1065.
Steven A. Rosenberg et al., "Antitumor Effects in Mice of the Intravenous Injection of Attenuated *Salmonella typhimurium*", Journal of Immunotherapy, 25(3)218-225, 2002.
John J. Rossi et al., "Ribozymes as Anti-HIV-1 Therapeutic Agents: Principles Applications and Problems", Aids Research and Human Retroviruses vol. 8, No. 2, 1992, pp. 183-189.

(56) References Cited

OTHER PUBLICATIONS

F.E. Ruiz et al., "A Clinical Inflammatory Syndrome Attributable to Aerosolized Lipid-DNA Administration in Cystic Fibrosis", Human Gene Therapy 12: 751-761 (May 1, 2001).
David S. Solomon et al., "Epidermal growth factor-related peptides and their receptors in human malignancies", Critical Reviews in Oncology/Hematology 19 (1995) 183-232.
Tristan J. Vaughan et al., "Human antibodies by design"; Nature Biotechnology; vol. 18; pp. 535-539; Jun. 1998,.
Arnold Hampel et al.; "'Hairpin' catalytic RNA model: evidence for helices and sequence requirement for substrate RNA"; Nucleic Acids Research; vol. 18; No. 2; pp. 299-304; 1989.
Len W. Seymore, Ph.D.; "Passive Tumor Targeting of Soluble Macromolecules and Drug Conjugates" Critical Reviews in Therapeutic Drug Carrier Systems, 9(2):135-187(1992).
Shangara Lal et al.; "Suicide genes: past, present and future perspectives"; Review Immunology Today; vol. 21, No. 1; pp. 48-54; Jan. 2000.
Denise R. Shaw et al.; "Phagocytosis requires repeated triggering of macrophage phagocytic receptors during particle ingestion"; Nature; vol. 289, pp. 409-411; Jan. 29, 1981.
Michael D. Sheets et al.; "Efficient construction of a large nonimmune phage antibody library: The production of high-affinity human single-chain antibodies to protein antigens"; Proc. Natl. Acac. Sci. USA; vol. 95, pp. 6157-6162; May 1998.
Sérgio Simões et al.; "Cationic liposomes as gene transfer vectors: Barriers to successful application in gene therapy"; Current Opinion in Molecular Therapeutics 1999 1(2):147-157.
M. Singh; Transferrin as A Targeting Ligand for Liposomes and Anticancer Drugs; Current Pharmaceutical Designes; 1999; vol. 5; No. 6; pp. 443-451.
Mouldy Sioud; "Therapeutic siRNAs"; Trends in Pharmacological Sciences; vol. 25; No. 1; pp. 22-28; Jan. 2004.
Surren A Soghomonyan et al.; "Positron emission tomography (PET) imaging of tumor-localized *Salmonella* expressing HSV1-TK"; Cancer Gene Therapy (2005) 12, 101-108.
Thomas Ebensen et al., "Bacterial Ghosts Are an Efficient Delivery System for DNA Vaccines", The Journal of Immunology, 2004, 172: 6858-6865.
Susanne Paukner et al., "Sealed Bacterial Ghosts—Novel Targeting Vehicles for Advanced Drug Delivery of Water-soluble Substances", Journal of Drug Targeting, Apr. 2003, vol. 11 (3) pp. 151-161.
Chakameh Azimpour Tabrizi et al., "Bacterial ghosts—biological particles as delivery systems for antigens, nucleic acids and drugs", Current Opinions in Biotechnology 2004, 15:530-537.
Susanne Paukner et al., "Bacterial ghosts as novel advanced drug delivery systems: antiproliferative activity of loaded doxorubicin in human Caco-2 cells", Journal of Controlled Release 94 (2004) 63-74.
Veronika Huter et al., "Bacterial ghosts as drug carrier and targeting vehicles", Journal of Controlled Release, 61 (1999) 51-63.
Alan Bridge et al., "Induction of an interferon response by RNAi vectors in mammalian cells," Nature Genetics, vol. 34, No. 3, (2003), pp. 263-264.
Catherine Grillot-Courvalin et al., "Wild-type intracellular bacteria delivery DNA into mammalian cells," Cellular Microbiology, vol. 4, No. 3, (2002), pp. 177-186.
Dawn E. Colwell et al., "Monoclonal Antibodies to *Salmonella* Lipopolysaccharide: Anti-O-Polysaccharide Antibodies Protect C3H Mice Against Challenge with Virulent *Salmonella* Typhimurium,"The Journal of Immunology, vol. 133, No. 2, Aug. 1984, pp. 950-957.
H. Brahmbhatt et al., U.S. PTO Notice of Allowance, U.S. Appl. No. 10/602,021 dated Jun. 22, 2009, 5 pgs.
H. Brahmbhatt et al., U.S. PTO Office Action, U.S. Appl. No. 10/581,990 dated Mar. 19, 2009, 32 pgs.
H. Brahmbhatt et al., U.S. PTO Office Action, U.S. Appl. No. 10/588,028 dated Mar. 18, 2009, 22 pgs.
H. Brahmbhatt et al., U.S. PTO Office Action, U.S. Appl. No. 10/602,021 dated May 4, 2006, 10 pgs.
H. Brahmbhatt et al., U.S. PTO Office Action, U.S. Appl. No. 10/602,021 dated May 15, 2007, 10 pgs.
H. Brahmbhatt et al., U.S. PTO Office Action, U.S. Appl. No. 10/602,021 dated Jul. 25, 2008, 10 pgs.
H. Brahmbhatt et al., U.S. PTO Office Action, U.S. Appl. No. 11/211,098 dated Feb. 24, 2009, 24 pgs.
H. Brahmbhatt et al., U.S. PTO Office Action, U.S. Appl. No. 11/211,098 dated Apr. 24, 2008, 38 pgs.
H. Brahmbhatt et al., U.S. PTO Office Action, U.S. Appl. No. 11/211,098 dated Aug. 7, 2009, 23 pgs.
H. Brahmbhatt et al., U.S. PTO Office Action, U.S. Appl. No. 11/691,698 dated Dec. 24, 2008, 13 pgs.
H. Brahmbhatt et al., U.S. PTO Office Action, U.S. Appl. No. 12/053,197 dated Aug. 25, 2009, 25 pgs.
Hao Wu et al., "Small Interfering RNA-induced Suppression of MDRI (P-Glycoprotein) Restores Sensitivity to Multidrug-resistant Cancer Cells," Cancer Research, vol. 63, Apr. 1, 2003, pp. 1515-1519.
Ian Tomlinson et al., "Methods for Generating Multivalent and Bispecific Antibody Fragments," Methods in Enzymology, vol. 326, (2000), pp. 461-479.
Inder M. Verma et al., "Gene Therapy: Twenty-First Century Medicine," Annu. Rev. Biochem., vol. 74, (2005), pp. 711-738.
J. H. Hong et al., "Antisense Bc12 oligonucleotide in cisplatin-resistant bladder cancer cell lines," BJU International, vol. 90, (2002), pp. 113-117.
Jean-Remi Bertrand et al., "Comparison of antisense oligonucleotides and siRNAS in cell culture and in vivo," Biochemical and Biophysical Research Communications, vol. 296, (2002), pp. 1000-1004.
L. R. Kelland, "Of mice and men": values and liabilities of the athymic nude mouse model in anticancer drug development, European Journal of Cancer, vol. 40, (2004), pp. 827-836.
Leoni A. Kunz-Schughart et al., "The Use of 3-D Cultures for High-Throughput Screening: The Multicellular Spheriod Model," Journal of Biomolecular Screening, vol. 9, (2004), pp. 273-285.
Michael J. McCluskie et al., "Route and Method of Delivery of DNA Vaccine Influence Immune Responses in Mice and Non-Human Primates," Molecular Medicine, vol. 5, (1999), pp. 287-300.
Michele Carbone et al., "Multistep and multifactorial carcinogenesis: when does a contributing factor become a carcinogen?," Seminars in Cancer Biology, vol. 14, (2004) pp. 399-405.
Michele De Palma et al., "In Vivo Targeting of Tumor Endothelial Cells by Systemic Delivery of Lentiviral Vectors," Human Gene Therapy, vol. 14, Aug. 10, 2003, pp. 1193-1206.
Robert S. Kerbel, "What is the optimal rodent model for anti-tumor drug testing?," Cancer and Metastasis Reviews, vol. 17, (1999), pp. 301-304.
Stephen L. Eck et al., "Gene-Based Therapy," Chapter 5, Goodman & Gilman's The Pharmacological Basis of Therapeutics, (1996), pp. 77-102.
Yi Lu et al., "Delivery of adenoviral vectors to the prostate for gene therapy," Cancer Gene Therapy, vol. 6, No. 1, (1999), pp. 64-72.
Singapore Written Opinion Application No. 200809513-5 dated Feb. 22, 2010.
Chakameh Azimpour Tabrizi et al., "Bacterial ghosts—biological particles as delivery systems for antigens, nucleic acids and drugs", Current Opinion in Biotechnology 2004, 15:530-537.
USP Guideline for Submitting Requests for Revision to USP-NF V3.Apr. 1, 2007—*Small Molecule Drug* Substances and Products, pp. 1-20.
Sean D. Conner et al., "Regulated Portals of Entry into the Cell", Nature, vol. 422, Mar. 6, 2003, pp. 37-44.
Esteban Veiga et al., "The role of clathrin-dependent endocytosis in bacterial internalization", Trends in Cell Biology, vol. 16, No. 10, pp. 499-504.
Supplementary European Search Report EP 07 82 5666 dated May 11, 2011.
Susanne Paukner et al., "Dna-Loaded Bacterial Ghosts Efficiently Mediate Reporter Gene Transfer and Expression in Macrophages", Molecular Therapy, vol. 11, No. 2, Feb. 2005, pp. 215-223.

(56) References Cited

OTHER PUBLICATIONS

Jennifer A. MacDiarmid et al., Bacterially-Derived Nanocells for Tumor-Targeted Delivery of Chemotherapeutics and Cell Cycle Inhibitors, Cell Cycle, 6:17, 2099-2105, Sep. 1, 2007.
Non-Final Office Action U.S. Appl. No. 13/184,068, dated Apr. 4, 2012.
Office Action issued in related U.S. Appl. No. 14/088,067, dated Jul. 6, 2016.
Chianale et al., (Biochem. J. 314: pp. 781-786 (1996).
Devault et al., Molecular and Cellular Biology 10(4), 1652-1663 (1990).
Office Action issued in related U.S. Appl. No. 14/088,067, dated Mar. 8, 2018.
Office Action issued in related U.S. Appl. No. 14/088,067, dated Oct. 18, 2018.
Office Action issued in co-pending U.S. Appl. No. 14/088,067, dated Jan. 8, 2021.
Notice of Allowance issued in co-pending U.S. Appl. No. 14/088,067, dated Jun. 16, 2021.

\* cited by examiner

TARGETED DELIVERY OF DRUGS, THERAPEUTIC NUCLEIC ACIDS AND FUNCTIONAL NUCLEIC ACIDS TO MAMMALIAN CELLS VIA INTACT KILLED BACTERIAL CELLS

CROSS-REFERENCE TO RELATED PATENT APPLICATIONS

This application is a divisional of U.S. patent application Ser. No. 11/765/,635, filed Jun. 20, 2007, now U.S. Pat. No. 9,878,043, which claims the priority benefit of U.S. Provisional Patent Application No. 60/815,883 filed on Jun. 23, 2006, and U.S. Provisional Patent Application No. 60/909,078 filed on Mar. 30, 2007, all of which are hereby incorporated herein by reference in their entirety.

BACKGROUND OF THE INVENTION

The present invention relates to targeted delivery, by means of intact killed bacterial cells, of bioactive molecules, including therapeutic nucleic acids, functional nucleic acids, drugs, peptides, proteins, carbohydrates and lipids, to mammalian host cells.

A number of hurdles continue to challenge targeted delivery of bioactive molecules to mammalian cells (e.g., cancer cells), particularly in-vivo. Those hurdles include (a) composition, functional characteristics and stability of delivery vehicles, (b) packaging therapeutically significant concentrations of bioactive molecules, (c) targeting desired diseased cells in-vivo, (d) overcoming a series of intracellular barriers and successfully deliver therapeutic concentrations of bioactive molecules to intracellular targets, (e) avoiding a range of host immune elements such as antibodies, complement, and macrophages that may destroy a vector before it reaches a target, (f) crossing the endothelial barrier of blood vessel walls, particularly at the site of a tumor mass, (g) migrating through several layers of cells to reach a target (e.g., it is known that a solid tumor is an organized structure containing both tumor cells and normal cells; hence a vector must cross several layers of normal cells to access malignant cells), (h) migrating through an extracellular matrix (ECM) comprised of glycoproteins, sulfated glycosaminoglycans, hyaluronan, proteoglycans and collagen that fills the space between cells and therefore hampers transport of a vector, and (i) addressing high interstitial hypertension (elevated hydrostatic pressure outside blood vessels) in the tumor microenvironment, which may limit the access of bioactive molecules.

A number of different vectors have been proposed for both nucleic acid and drug delivery, including viral, non-viral non-living, and non-viral living vectors. The non-viral non-living vectors have been adapted for both nucleic acid and drug delivery. The other two types of vectors have been adapted for nucleic acid delivery. Non-viral living vectors are mainly being developed for direct tumor-cell killing capabilities. While all these vectors have advantages, they also have drawbacks.

Viral vectors, such as retrovirus, adenovirus, adeno-associated virus, pox virus, herpes simplex virus, and lentivirus, have been developed for gene delivery. However, viral vectors are unable to deliver genes systemically and specifically to primary and/or metastasized tumor cells without infecting normal tissues (Akporiaye and Hersh, 1999; Biederer et al., 2002; Green & Seymour, 2002). Additionally, the extremely limited diffusibility of virions within extracellular spaces significantly hinders the dissemination of viral vectors. Moreover, viruses are antigenic, and therefore give rise to host immune responses. Such immune responses include both specific adaptive responses and non-specific innate responses (Chen et al., 2003; Ferrari et al., 2003; Wakimoto et al., 2003). The latter plays an important role in eliminating adenoviral vectors (Liu and Muruve, 2003) and HSV (Wakimoto et al., 2003).

Non-viral non-living vectors are exemplified by cationic polymers (polyplexes), cationic lipids (liposomes, lipoplexes) and synthetic nanoparticles (nanoplexes). They are more versatile than viral vectors, and offer several distinct advantages because their molecular composition can be controlled, manufacturing and analysis of such vectors is fairly simple, they can accommodate a range of transgene sizes (Kreiss et al., 1999; de Jong et al., 2001) and they are less immunogenic (Whitmore et al., 1999, 2001; Dow et al., 1999; Ruiz et al., 2001). The efficiency of gene delivery with non-viral non-living vectors is significantly less, however, than with viral vectors. At least $10^6$ plasmid copies are needed to transfect a single cell, with approximately $10^2$-$10^4$ copies actually making it to the nucleus for transgene expression (Feigner and Ringold, 1989; James and Giorgio, 2000; Tachibana et al., 2002). This inefficiency is attributable to the inability of non-viral non-living vectors to overcome the numerous challenges encountered between a site of administration and localization in a target cell nucleus, including, (a) the physical and chemical stability of DNA and its delivery vehicle in the extracellular space, (b) cellular uptake by endocytosis, (c) escape from the endosomal compartments prior to trafficking to lysosomes and cytosolic transport, and (d) nuclear localization of the plasmid for transcription. In addition to these physical and chemical obstacles, biological barriers, such as immunogenic responses to the vector itself and immune stimulation by certain DNA sequences containing a central unmethylated CpG motif exist (Yew et al., 1999; Scheule, 2000; Ruiz et al., 2001).

As an alternate to non-living nucleic acid/drug delivery vehicles, live bacterial vectors have also been developed for tumor targeted therapy (Pawalek et al., 2003; Soghomonyan et al., 2005). These vectors do not carry a payload of nucleic acids or drugs, but preferentially accumulate in tumor cells, replicate intracellularly and kill the infected cells (Pawelek et al., 1997). This phenomenon is thought to be facilitated by a complex bacterial system for introducing bacterial proteins directly into mammalian cells, which can result in the induction of apoptosis (Chen et al., 1996; Monack et al., 1996; Zhou et al., 2000). Currently, *Bifidobacterium* (Yazawa et al., 2000; 2001; Li et al., 2003), *Clostridium* (Minton et al., 1995; Fox et al., 1996; Lemmon et al., 1997; Theys et al., 2001; Dang et al., 2001; Nuyts et al., 2002a; 2002b; Liu et al., 2002) *Salmonella* (Pawelek et al., 1997; Low et al., 1999; Platt et al., 2000; Luo et al., 2001; Rosenberg et al., 2002) and *Vibrio* (Yu et al., 2004) are under investigation as tumor-selective live bacterial vectors.

Live attenuated bacteria have also been explored as vehicles for delivering nucleic acids (Paglia et al., 2000; Weiss and Chakraborty 2001; Yuhua et al., 2001), which may encode angiogenic inhibitors (Lee et al., 2005a; 2005b; Li et al., 2003), prodrug-converting enzymes (King et al., 2002) or cytokines (Yamada et al., 2000). Significant drawbacks of this approach include (a) live recombinant bacteria gradually lose plasmid DNA in vivo, mainly due to the absence of selection pressure and associated plasmid segregation, (b) bacteria carrying plasmid DNA tend to have a lower growth rate and appear to accumulate at lower levels and reside for a shorter period of time within tumors than bacteria without plasmids, (c) live Gram-negative bacterial vectors can cause severe endotoxin response in mammalian hosts, possibly due to in-vivo shedding of endotoxin (lipopolysaccharide; LPS), and evoke a Toll-like receptor response due to cellular invasion, (d) most of the tumor-targeting live bacteria accumulate and grow in the necrotic and relatively hypoxic foci within tumors, but not in well-oxygenated tumors at the rim of the growing nodules where tumor cells are normally most aggressive, (e) the risk associated with possible reversion to a virulent phenotype of these bacteria is a major concern (Dunham, 2002), and (f) the risk of infecting normal cells may lead to bacteremia and associated septic shock. The latter may particularly be a problem in immuno-compromised patients, such as late stage cancer patients.

Because problems continue to hamper the success of cancer therapeutics in particular, an urgent need exists for targeted delivery strategies that will either selectively deliver bioactive agents to tumor cells and target organs, or protect normal tissues from administered antineoplastic agents. Such strategies should improve the efficacy of treatment by increasing the therapeutic indexes of anticancer agents, while minimizing the risks of therapy-related toxicity.

The present invention provides a versatile delivery vehicle for improved drug, therapeutic nucleic acid and functional nucleic acid delivery strategies, especially but not exclusively in the context of cancer chemotherapy.

SUMMARY OF THE INVENTION

To address these and other needs, the present invention provides, in one aspect, a composition that comprises a plurality of intact killed bacterial cells and a pharmaceutically acceptable carrier. The killed bacterial cells contain a therapeutic nucleic acid, a drug or a functional nucleic acid. With respect to the latter, in one embodiment the functional nucleic acid is plasmid-free. In this regard, functional nucleic acids are packaged directly into killed bacterial cells by passing through the bacterial cell's intact membrane, without using plasmid-based expression constructs or the expression machinery of a host cell. Such plasmid-free functional nucleic acids are exemplified by single-, double-, or multi-stranded DNA or RNA. In one embodiment, killed bacterial cells contain plasmid-free functional nucleic acid that is regulatory RNA. In a preferred embodiment, the composition is essentially free of endotoxin.

The invention also provides bispecific ligands useful for targeting killed bacterial cells to mammalian host cells. The bispecific ligand may be polypeptide, carbohydrate or glycopeptide, and may comprise an antibody or antibody fragment. In preferred embodiments, the bispecific ligand has a first arm that carries specificity for a bacterial surface structure and a second arm that carries specificity for a mammalian cell surface structure. Further, the first arm and the second arm of the bispecific ligand may be monospecific or multivalent. A desirable bacterial surface structure for ligand binding is an O-polysaccharide component of a lipopolysaccharide (LPS). Desirable mammalian cell surface structures for ligand binding are receptors, preferably those capable of activating receptor-mediated endocytosis.

According to another aspect, the invention provides a delivery method that comprises bringing a plurality of killed bacterial cells into contact with mammalian cells that are phagocytosis- or endocytosis-competent, such that the killed bacterial cells are engulfed by the mammalian cells and release their payload intracellularly. The payload may comprise a therapeutic nucleic acid, a functional nucleic acid or a drug.

In one embodiment, a method of delivering a functional nucleic acid, comprises (a) providing a plurality of killed bacterial cells in a pharmaceutical carrier, each killed bacterial cell of the plurality encompassing (i) a functional nucleic acid or (ii) a plasmid comprised of a segment that encodes a functional nucleic acid and then (b) bringing said killed bacterial cells of the plurality into contact with target mammalian cells, such that said mammalian cells engulf said killed bacterial cell, whereby said functional nucleic acid is released into the cytoplasm of the target cell. In one aspect, the killed bacterial cells are plasmid-free, while in another the functional nucleic acid is regulatory RNA.

According to another aspect, the invention provides a targeted delivery method that comprises bringing bispecific ligands into contact with (i) intact killed bacterial cells that contain a desired payload and (ii) mammalian cells, preferably non-phagocytic mammalian cells. The bispecific ligands have specificity for both a surface component on the intact killed bacterial cells and a surface component on the mammalian cells, such as a receptor. As a result, the ligands cause the killed bacterial cell to bind to the mammalian cells, the killed bacterial cells are engulfed by the mammalian cells, and the payload contained in the killed bacterial cells is released into the cytoplasm of the mammalian cell. The payload may comprise a therapeutic nucleic acid, a functional nucleic acid or a drug.

In yet another aspect, the invention provides a method of overcoming drug resistance or apoptosis resistance and treating a malignancy in a subject by delivering a functional nucleic acid to a target cell. The method comprises bringing a killed bacterial cell that contains (i) a functional nucleic acid molecule or (ii) a plasmid comprised of a segment that encodes a functional nucleic acid molecule into contact with a target mammalian cell. The mammalian cell engulfs the killed bacterial cell, the functional nucleic acid is released into the cytoplasm, transported to the nucleus and expressed by the target cell.

In relation to this invention, the contact between killed bacterial cells and mammalian cells may be in vitro or in vivo.

The invention further provides methods for loading killed bacterial cells with a drug. One such method involves creating a concentration gradient of the drug between an extracellular medium containing the killed bacterial cells and the killed bacterial cell cytoplasm. The drug naturally moves down this concentration gradient, into the killed bacterial cell cytoplasm. Leakage of the drug from the bacterial cytoplasm is prevented due to the bacterial cells being metabolically inactive.

Another method of loading killed bacterial cells with a drug involves culturing a bacterial cell under conditions, such that the bacterial cell transcribes and translates a therapeutic nucleic acid encoding the drug, such that the drug is released into the cytoplasm of the bacterial cell, and then killing the bacterial cell to form one or more killed bacterial cells containing the drug in their cytoplasm.

In accordance with another aspect, the present invention contemplates a method for formulating a killed bacterial cell with a plasmid-free functional nucleic acid. The method comprises co-incubating a plurality of killed bacterial cells with a functional nucleic acid, such as regulatory RNA like siRNA, miRNA or shRNA, in a buffer. In some embodiments, the co-incubation may involve gentle shaking, while in others the co-incubation is static. In some aspects, the co-incubation lasts about half an hour, while in others it lasts about an hour. In one embodiment, the buffer comprises buffered saline, for example, a 1X phosphate buffer solution. In another embodiment, the co-incubation is conducted at a temperature of about 4° C. to about 37° C., about 20° C. to about 30° C., about 25° C., or about 37° C. The co-incubation can comprise about $10^7$, $10^8$, $10^9$, $10^{10}$, $10^{11}$, $10^{12}$ or $10^{13}$ killed bacterial cells.

The present invention contemplates a use of intact killed bacterial cells and bispecific ligands in the preparation of a medicament, for use in a method of treating a disease or modifying a trait by administration of the medicament to a cell, tissue, or organ. In the medicament, the killed bacterial cells contain a therapeutic nucleic acid molecule, a drug or a functional nucleic acid molecule, and, optionally, bispecific ligands that are capable of binding to the killed bacterial cells and to target non-phagocytic mammalian cells. Such medicaments are useful to treat various conditions and diseases by increasing expression or function of a desired protein, or by inhibiting expression or function of a target protein. Illustrative of such conditions and diseases are a cancer and an acquired disease, such as AIDS, pneumonia emphysema, and tuberculosis. Alternatively, the treatment may affect a trait, such as fertility, or an immune response associated with an allergen or an infectious agent.

The present invention also provides a pharmaceutically acceptable method for purifying intact killed bacterial cells. The method combines (i) killing live bacterial cells with antibiotics, (ii) cross-flow filtration and/or dead-end filtration, to eliminate free endotoxin, cellular debris, free nucleic acids, bacterial membrane blebs, media contaminants, and (iii) antibody-based sequestration, to eliminate residual free endotoxin.

DETAILED DESCRIPTION

Figure 1:
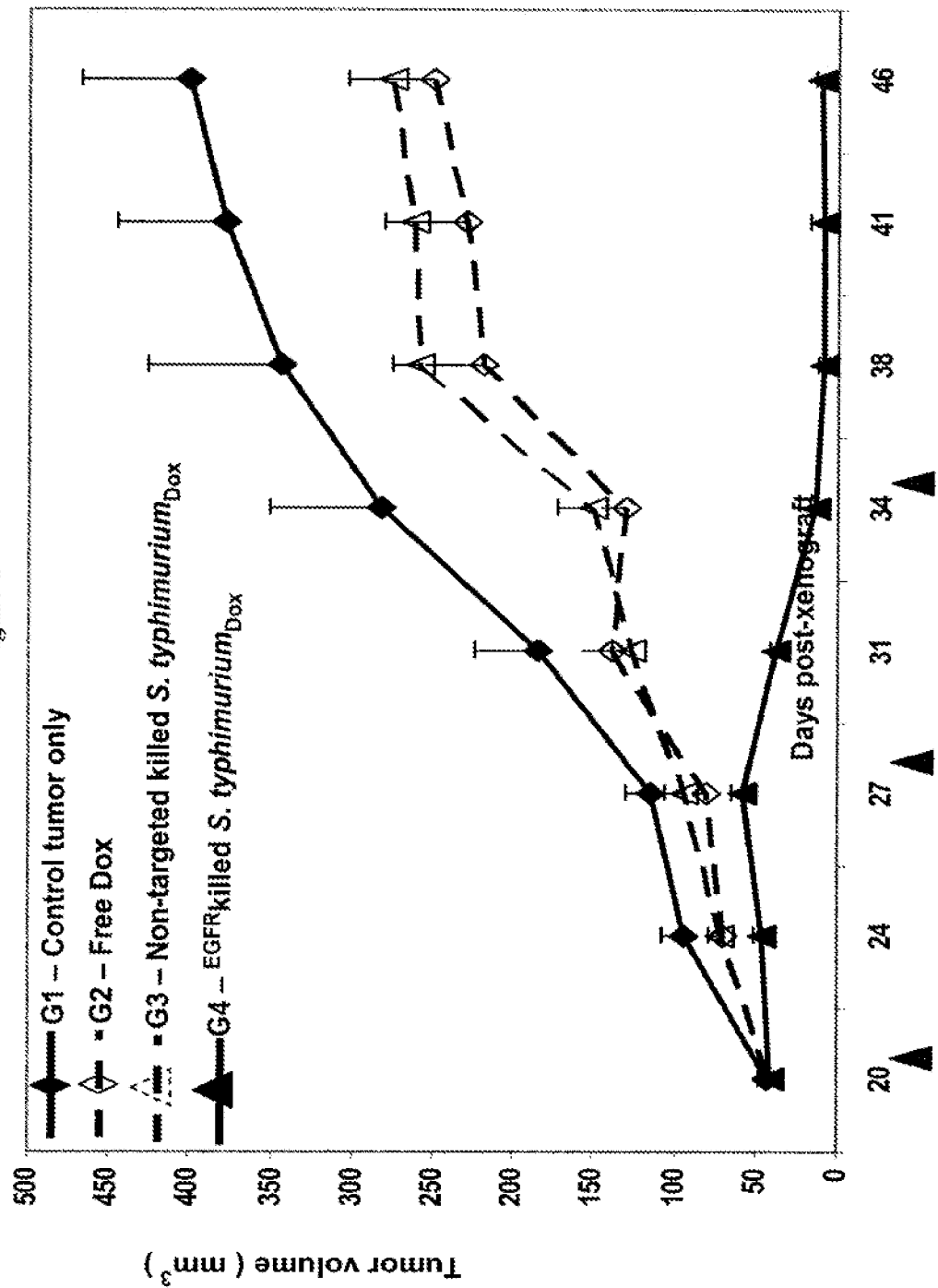
FIG. 1 shows highly significant anti-tumor effects via bispecific antibody-targeted, chemotherapeutic drug-packaged intact killed bacterial cells. Human breast cancer (MDA-MB-468) xenograft was established subcutaneously (between the shoulder blades) in Balb/c nu/nu mice and when tumor volumes reached ~70 mm$^3$, mice were treated (n=11 mice per group) intravenously (i.v.) with free doxorubicin (G2), or non-targeted intact killed *S. typhimurium* bacterial cells packaged with dox (G3), or with EGFR-targeted intact killed *S. typhimurium* bacterial cells packaged with dox (G4). G1 mice were controls and received sterile physiological saline (i.v.). The treatments were administered on the days marked by a triangle on the x-axis and tumor volume was measured as shown on the y-axis. The result shows a highly significant anti-tumor effect when $^{EGFR}$killed *S. typhimurium*$_{Dox}$ (G4) was used as a treatment while the G2 and G3 mice showed no anti-tumor effects. Standard deviation is shown for each measurement.

The present inventors have determined that intact killed bacterial cells are effective vehicles for targeted delivery of therapeutic nucleic acids, functional nucleic acids and drugs to diseased cells, particularly cancer cells, both in vitro and in vivo. A number of surprising discoveries underlie that determination.

For example, the inventors discovered that when compositions comprising (a) intact killed bacterial cells containing a therapeutic nucleic acid, drug or functional nucleic acid payload (b) bispecific targeting ligands, and (c) a pharmaceutically acceptable carrier are brought into contact with diseased cells in vitro or in vivo, the intact killed bacterial cell vehicles are endocytosed at high efficiency into target non-phagocytic mammalian cells. This discovery was a surprise, because although bispecific ligands have been used to target viral and non-viral delivery vehicles to non-phagocytic mammalian cells (Wickham et al., 1996; Nettelbeck et al., 2001; Boucher et al., 2003; Ogris & Wagner, 2002), it was believed that receptor-mediated endocytosis would not work for particles as large as bacterial cells.

For instance, adenoviral vectors have been redirected to target mammalian cell-surface receptors, such as endoglin on endothelial cells, and internalized via clathrin-coated pits in the mammalian cell plasma membrane. Wickham et al., 1996; Nettelbeck et al., 2001; Boucher et al., 2003. The clathrin-coated pits resemble a cup that envelopes the vector, but the size of the cup is understood to be a limiting factor. Clathrin-coated pits have a limited size of 85-110 nm, due to the size of the clathrin coat. Swanson & Watts, 1995. Bacterial cells, by contrast, are at least 400 nm in diameter and 1,000 nm in length. Hence, is was not expected that such a targeting approach would work for killed bacterial cells.

Knowledge concerning other large vectors supported the expectation that killed bacterial cells would not be internalized through clathrin-coated pits. For instance, large lipoplexes (non-viral vectors up to 500 nm) preferentially enter cells by receptor- and clathrin-independent endocytosis, while smaller lipoplexes (less than 200 nm) can be internalized via a non-specific, clathrin-dependent process. Simoes et al., 1999. Likewise, large viruses, such as vaccinia virus, on the order of 350 nm×250 nm in size, do not infect mammalian cells via a clathrin-coated pathway. Essani and Dales, 1979.

In a similar vein, non-phagocytic mammalian cells cannot engulf large pathogens, like bacterial cells. Only professional phagocytes like macrophages engulf such pathogens, and the engulfment process is clathrin- and receptor-independent, being accomplished by phagocytosis. The interaction of large pathogens with the cell surface induces a complex signaling cascade, leading to actin rearrangements at the plasma membrane to form a large phagocytic cup, which engulfs the bacterium. Dramsi and Cossart, 1998. The signaling cascades that are responsible, on bacterial entry, for actin rearrangements at the plasma membrane are poorly understood. Galan, 1996; Menard et al., 1996; Finlay and Cossart, 1997; Dramsi and Cossart, 1998.

Specific investigations into the effect of particle size on receptor-mediated endocytosis show that the process is strongly size-dependent. For example, Aoyama et al., 2003, studied the effect of particle size on glycoviral gene delivery and concluded that the optimal particle size for receptor-mediated endocytosis is ~25 nm. See also Nakai et al., 2003; Osaki et al., 2004. Gao et al., 2005, confirmed that conclusion.

Moreover, even though bispecific ligands reportedly have been used to re-direct viral vectors, the method has not always been successful in the context of gene delivery. In attempted retargeting of viruses from their native receptors to alternative receptors, many experiments have shown that cell surface attachment is insufficient for sustained viral entry and gene expression. Also, when virus envelope proteins were modified for re-targeting, they exhibited low fusion activity, resulting in inefficient viral entry into cells. Zhao et al., 1999. In the absence of specific targeting, strategies have depended on direct injection to a localized site. Akporiaye & Hersh, 1999.

Thus, the art suggested that bispecific ligands would not enable intact killed bacterial cell vehicles to enter non-phagocytic mammalian cells. In further support of this point, the inventors discovered that non-targeted killed bacterial cells are unable to specifically adhere to and deliver a payload to non-phagocytic mammalian cells, even after repeated attempts with prolonged incubation periods in a number of mammalian cell lines. In particular, non-targeted killed bacterial cells are not internalized by non-phagocytic mammalian cells. By contrast, killed bacterial cells are readily phagocytosed by professional phagocytes like macrophages. This corroborates earlier findings that microparticles up to 12 μm are phagocytosed by professional phagocytes (Kanke et al., 1983) and that maximal uptake of microparticles into macrophages occurs with particles of <2 μm (Tabata and Ikada, 1988; 1990). Unlike viral vectors that specifically adhere to viral receptors and trigger their internalization, therefore, killed bacterial cells have no similar mechanism to invade enter non-phagocytic mammalian cells.

Against this background, the inventors also discovered that bispecific ligands can direct the endocytosis of intact killed bacterial cells within non-phagocytic mammalian cells. Preliminary data suggests that internalization of bacterial cells may occur via the receptor- and macropinocytosis-dependent pathway, though the Applicants are not bound to such a theory.

The inventors further discovered that following endocytosis, the killed bacteria are completely degraded in intracellular vacuoles, presumably endo-lysosomal compartments. This was surprising because harsh degradative mechanisms that are capable of degrading large biological particles like bacterial and parasitic cells were thought to operate only in professional phagocytes, like macrophages. Those mechanisms were thought to permit full antigen processing and presentation by professional phagocytes. Because most non-phagocytic cells do not process and present antigens, it was believed that they contained only mild antigen processing systems that are mainly used for re-cycling of cellular components.

After being internalized by receptor-mediated endocytosis, vectors are enclosed within endosomal or lysosomal membranes, and are therefore separated from the cytoplasm. This constitutes a significant impediment to payload delivery, especially because endosomal and lysosomal compartments can become highly caustic and degrade more than 99% of a payload, such as nucleic acids in a vector. Successful gene delivery vectors have mechanisms that allow nucleic acids to enter the cytoplasm, but skilled artisans would not expect minicells to have such mechanisms.

Viruses, for example, have evolved sophisticated processes to enter the mammalian cell cytoplasm. Enveloped retro-viruses, such as HIV-1, gain access to the cytoplasm by direct fusion with the plasma membrane. Stein et al., 1987. Non-enveloped viruses use various strategies to penetrate the endosomal membrane after endocytosis. For example, influenza viruses induce fusion of the viral and endosomal membranes, which is triggered by the acidic environment of the endosome. Marsh & Helenius, 1989. At low pH, the predominant influenza viral envelope glycoprotein hemagglutinin (HA) undergoes conformational changes, leading to the protrusion of a hydrophobic spike into the endosomal membrane that initiates membrane fusion. Bullough et al., 1994. Adenoviruses also are believed to escape into the cytosol by a mechanism tied to acidification of the endosome. Low pH has several effects on the adeno viral capsid. For example, the capsid's penton protein undergoes conformational changes that expose hydrophobic regions for endosomal membrane interaction. Seth et al., 1985. Additionally, intrinsic protease activity of the adeno viral capsid also seems to contribute to endosomal escape. Greber et al., 1996.

For liposomal vectors, the endosomal membrane barrier continues to limit the efficiency of gene delivery. Successful release of liposomal nucleic acids is understood to result from disruption of the endo-lysosome membrane. Xu & Szoka, 1996; El Ouahabi et al., 1997; Zelphati & Szoka, 1996a; Wattiaux et al., 2000. Disruption of the endo-lysosomal membrane is thought to occur via transbilayer flip-flop of lipids, leading to membrane destabilization and penetration of naked DNA into the cytoplasm. Zelphati & Szoka, 1996a; 1996b; Mui et al., 2000. Studies have further demonstrated that cytoplasmic release of liposomal contents involves (a) charge neutralization of a cationic complexing agent with anionic macromolecules such as anionic lipids and proteoglycans, (b) cationic lipid-mediated fusion, and (c) membrane destabilization by pH-sensitive lipids. Wrobel & Collins, 1995; Meyer et al., 1997; Clark & Hersh, 1999. Additional studies have shown that a mixture of neutral lipid (DOPE) with cationic lipid facilitates membrane disruption and increases the amount of liposomal contents released into the cytoplasm, because DOPE promotes the fusion of liposome particles with endosomal membranes. Farhood et al., 1995; Fasbender et al., 1997; Hafez et al., 2001. Also, cationic PEI and polyamine dendrimers have been used to facilitate disruption of the endolysosomal membrane, because they have an extensive buffering capacity that provokes swelling and disruption of endosomes. Klemm, 1998; Sonawane et al., 2003. Additional functionality can be incorporated into liposome vectors in the form of an endosomolytic pore forming protein from *Listeria monocytogenes*, listeriolysin O (LLO). Lorenzi and Lee, 2005. LLO is capable of breaching the endosomal membrane, thereby allowing escape of endosomal contents into the cytoplasm. Lee et al., 1996.

Thus, current teachings suggest that sophisticated mechanisms are necessary to allow some vector payload to escape the lysosomal membrane. The killed bacterial cell is a non-living particle and does not carry any lysosomal membrane destabilizing functions. The inventors discovered, that if killed bacterial cells carry at least 70 to 100 copies of plasmid DNA, then some of this DNA can escape the endosomal membrane without the need to destabilize or disrupt the endosomal membrane. This suggests that while most of the plasmid DNA is likely to be degraded in the endo-lysosomal vacuole, it was possible to overwhelm the system and thereby permit some DNA to escape intact into the mammalian cell cytoplasm. Additionally, the inventors discovered that although non-phagocytic mammalian cells are not thought to carry harsh lysosomal processing mechanisms that could degrade complex multi-component structures like bacterial cells, that may not be true. The current view specifies that intracellular degradation of such complex structures like bacterial cells is limited to professional phagocytic cells that are capable of complete antigen processing and presentation.

In a related aspect, the inventors discovered that a significant concentration of bioactive drug carried by bispecific ligand-targeted, drug-packaged killed bacterial cells also escapes the endo-lysosomal membrane and enters the mammalian cell cytoplasm. Additionally, they discovered that killed bacterial cells are highly versatile in their capacity to package a range of different drugs (e.g., hydrophilic, hydrophobic, and amphipathic drugs such as doxorubicin, paclitaxel, cisplatin, carboplatin, 5-fluorouracil, and irinotecan) and have found that all are readily packaged in killed bacterial cells in therapeutically significant concentrations.

The inventors further discovered that when bispecific antibody-targeted, drug-packaged killed bacterial cells (for simplicity, also designated "therapeutic") were administered intravenously into nude mice carrying human tumor xenografts, they extravasated from the blood vessel walls surrounding the tumor mass and entered into the tumor microenvironment.

Targeting of particle-based systems in the context of cancer therapy has exploited the leaky tumor vasculature (Jain, 1998) and the lack of an effective lymphatic drainage (Maeda and Matsumura, 1989; Seymour, 1992; Yuan et al., 1994), which results in enhanced permeability and retention (EPR) effect (Maeda, 2001) of circulating particles (passive targeting). Tumor vessels have an irregular diameter, an abnormal branching pattern, and do not fit well into the usual classification of arterioles, capillaries, or venules. Warren, 1979; Less et al., 1991, 1997; Konerding et al., 1995. Of particular functional importance, tumor vessels are unusually leaky. Peterson and Appelgren, 1977; Gerlowski and Jain, 1986; Jain, 1987, 1997; Dvorak et al., 1988. The hyperpenneability of tumor microvessels to large molecules has been observed in numerous studies. Gerlowski and Jain, 1986; Jain, 1987; Jain 1996. However, the upper size limit for agents that can traverse vessels of different tumors and how that is regulated are poorly understood. One study measured the pore cutoff size of a human colon carcinoma grown subcutaneously in immunodeficient mice to be between 400-600 nm. Yuan et al., 1995. Others reported that some tumors have a pore cut-off size of only 100 nm. Hobbs et al., (1998). Accordingly, it was surprising to find that intact killed bacterial cells larger than 1,000 µm are able to extravasate the endothelial cell wall surrounding tumors. This discovery enables the use of intact killed bacterial cells for tumor therapy in vivo.

Additionally, it previously was suggested that the abnormal tumor microenvironment is characterized by interstitial hypertension (elevated hydrostatic pressure outside the blood vessels; Less et al., 1992; Jain, 2001) that limits access of anti-cancer therapeutics. For instance, it was reported that when breast cancer (MDA-MD-231) tumors established orthotopically in SCID mice were studied following intravenous injection of contrast agent Gadolinium diethylen-etriamine-penta-acetate, there was a decrease in the entry of the contrast agent to the tumor. Dadiani et al., 2004. The authors of that report speculated that the observed increase in interstitial hypertension suggests that the high interstitial pressure forces fluid to reenter the blood vessels, thereby increasing outflux to influx ratio. Interestingly, the inventors discovered that killed bacterial cells are not hindered by such interstitial hypertension, but are able to achieve highly significant anti-tumor effects (FIG. 1).

The following description outlines the invention related to these discoveries, without limiting the invention to the particular embodiments, methodology, protocols or reagents described. Likewise, the terminology used herein describes particular embodiments only, and does not limit the scope of the invention. Unless defined otherwise, all technical and scientific terms used in this description have the same meaning as commonly understood by those skilled in the relevant art. Additionally, the singular forms "a," "an," and "the" include plural reference unless the context clearly dictates otherwise.

Compositions Comprising Intact Killed Bacterial Cells

In one aspect, the invention provides a composition comprising intact killed bacterial cells and a pharmaceutically acceptable carrier therefor. The killed bacterial cells may contain a therapeutic nucleic acid, a drug, a functional nucleic acid molecule or a combination thereof.

Intact Killed Bacterial Cells

According to the invention, killed bacterial cells are non-living prokaryotic cells of bacteria, cyanobateria, eubacteria and archaebacteria, as defined in the 2nd edition of BERGEY'S MANUAL OF SYSTEMATIC BIOLOGY. Such cells are deemed to be "intact" if they possess an intact cell wall and/or cell membrane and contain genetic material (nucleic acid) that is endogenous to the bacterial species.

Therapeutic Nucleic Acids and Therapeutic Expression Products

A therapeutic nucleic acid molecule encodes a product, such as a peptide, polypeptide or protein, the production of which is desired in a target cell. For example, the genetic material of interest can encode a hormone, receptor, enzyme, or (poly) peptide of therapeutic value. Such methods can result in transient expression of non-integrated transferred DNA, extrachromosomal replication and expression of transferred replicons such as episomes, or integration of transferred genetic material into the genomic DNA of host cells.

The phrase "nucleic acid molecules" and the term "polynucleotides" denote polymeric forms of nucleotides of any length, either ribonucleotides or deoxynucleotides. They include single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The backbone of a polynucleotide can comprise sugars and phosphate groups, as is typical for RNA and DNA, or modified or substituted sugar or phosphate groups. Alternatively, the backbone of the polynucleotide can comprise a polymer of synthetic subunits such as phosphoramidites and thus can be an oligodeoxy-nucleoside phosphoramidate or a mixed phosphoramidate-phosphodiester oligomer. A polynucleotide may comprise modified nucleotides, such as methylated nucleotides and nucleotide analogs, uracyl, other sugars, and linking groups such as fluororibose and thioate, and nucleotide branches. A polynucleotide may be further modified, such as by conjugation with a labeling component. Other types of modifications include caps, substitution of one or more of the naturally occurring nucleotides with an analog, and introduction of means for attaching the polynucleotide to proteins, metal ions, labeling components, other polynucleotides, or a solid support.

"Polypeptide" and "protein," used interchangeably herein, refer to a polymeric form of amino acids of any length, which may include translated, untranslated, chemically modified, biochemically modified, and derivatized amino acids. A polypeptide or protein may be naturally occurring, recombinant, or synthetic, or any combination of these. Moreover, a polypeptide or protein may comprise a fragment of a naturally occurring protein or peptide. A polypeptide or protein may be a single molecule or may be a multi-molecular complex. In addition, such polypeptides or proteins may have modified peptide backbones. The terms include fusion proteins, including fusion proteins with a heterologous amino acid sequence, fusions with heterologous and homologous leader sequences, with or without N-terminal methionine residues, immunologically tagged proteins, and the like.

The term "expression" generally refers to the process by which a polynucleotide sequence undergoes successful transcription and translation such that detectable levels of the amino acid sequence or protein are expressed. In certain contexts herein, expression refers to the production of mRNA. In other contexts, expression refers to the production of protein.

Transcription or translation of a given therapeutic nucleic acid molecule may be useful in treating cancer or an acquired disease, such as AIDS, pneumonia, emphysema, or in correcting inborn errors of metabolism, such as cystic fibrosis. Transcription or translation of a therapeutic nucleic acid may also effect contraceptive sterilization, including contraceptive sterilization of feral animals. Allergen-mediated and infectious agent-mediated inflammatory disorders also can be countered by administering, via the present invention, a therapeutic nucleic acid molecule that, upon expression in a patient, affects immune response(s) associated with the allergen and infectious agent, respectively. A therapeutic nucleic acid molecule also may have an expression product, or there may be a downstream product of post-translational modification of the expression product, that reduces the immunologic sequalae related to transplantation or that helps facilitate tissue growth and regeneration.

The terms "Cancer," "neoplasm," "tumor," "malignancy" and "carcinoma," used interchangeably herein, refer to cells or tissues that exhibit an aberrant growth phenotype characterized by a significant loss of control of cell proliferation. The methods and compositions of this invention particularly apply to precancerous, malignant, pre-metastatic, metastatic, and non-metastatic cells.

A therapeutic nucleic acid molecule may be the normal counterpart of a gene that expresses a protein that functions abnormally or that is present in abnormal levels in a disease state, as is the case, for example, with the cystic fibrosis transmembrane conductance regulator in cystic fibrosis (Kerem et al., 1989; Riordan et al., 1989; Rommens et al., 1989), with β-globin in sickle-cell anemia, and with any of α-globin, β-globin and γ-globin in thalassemia. Thus, an excess production of α-globin over β-globin which characterizes β-thalassemia can be ameliorated by gene therapy, in accordance with the present invention, using an intact killed bacterial cell engineered to contain a plasmid incorporating a sequence that has an antisense RNA transcript vis-à-vis a target sequence of the α-globin mRNA.

In the treatment of cancer, a therapeutic nucleic acid molecule suitable for use according to the present invention could have a sequence that corresponds to or is derived from a gene that is associated with tumor suppression, such as the p53 gene, the retinoblastoma gene, and the gene encoding tumor necrosis factor. A wide variety of solid tumors—cancer, papillomas, and warts—should be treatable by this approach, pursuant to the invention. Representative cancers in this regard include colon carcinoma, prostate cancer, breast cancer, lung cancer, skin cancer, liver cancer, bone cancer, ovary cancer, pancreas cancer, brain cancer, head and neck cancer, and lymphoma. Illustrative papillomas are squamous cell papilloma, choroid plexus papilloma and laryngeal papilloma. Examples of wart conditions are genital warts, plantar warts, epidermodysplasia verruciformis, and malignant warts.

A therapeutic nucleic acid molecule for the present invention also can comprise a DNA segment coding for an enzyme that converts an inactive prodrug into one or more cytotoxic metabolites so that, upon in vivo introduction of the prodrug, the target cell in effect is compelled, perhaps with neighboring cells as well, to commit suicide. Preclinical and clinical applications of such a "suicide gene," which can be of non-human origin or human origin, are reviewed by Spencer (2000), Shangara et al. (2000) and Yazawa et al. (2002). Illustrative of suicide genes of non-human origin are those that code for HSV-thymidine kinase(tk), cytosine deaminase (CDA)+uracil phophoribosyl-transferase, xanthine-guanine phophoribosyl-transferase (GPT), nitroreductase (NTR), purine nucleoside phosphorylase (PNP, DeoD), cytochrome P450 (CYP4B1), carboxypeptidase G2 (CPG2), and D-amino acid oxidase (DAAO), respectively. Human-origin suicide genes are exemplified by genes that encode carboxypeptidase A1 (CPA), deoxycytidine kinase (dCK), cytochrome P450 (CYP2B1,6), LNGFR/FKBP/Fas, FKBP/Caspases, and ER/p53, respectively.

A suicide-gene therapy could be applied to the treatment of AIDS. This strategy has been tested with suicide vectors that express a toxic gene product as soon as treated mammalian cells become infected by HIV-1. These vectors use the HIV-1 regulatory elements, Tat and/or Rev, to induce the expression of a toxic gene such as α-diphtheria toxin, cytosine deaminase, or interferon-a2 after infection by HIV-1. See Curiel et al., 1993; Dinges et al., 1995; Harrison et al., 1992a; Harrison et al., 1992b; Ragheb et al., 1999.

The therapeutic nucleic acid of the invention typically is contained on a plasmid within the killed bacterial cell. The plasmid also may contain an additional nucleic acid segment that functions as a regulatory element, such as a promoter, a terminator, an enhancer or a signal sequence, and that is operably linked to the therapeutic nucleic acid segment. A suitable promoter can be tissue-specific or even tumor-specific, as the therapeutic context dictates.

The therapeutic nucleic acid may encode a suicide gene or a normal counter part of a gene that expresses a protein that functions abnormally or is present in abnormal levels in the mammalian cell. Moreover, the therapeutic nucleic acid may be contained on a plasmid comprised of multiple nucleic acid sequences. Further, the plasmid may contain a regulatory element and/or a reporter element.

The term "gene" refers to a polynucleotide sequence that comprises control and coding sequences necessary for the production of a polypeptide or precursor. The polypeptide can be encoded by a full length coding sequence or by any portion of the coding sequence. A gene may constitute an uninterrupted coding sequence or it may include one or more introns, bound by the appropriate splice junctions. Moreover, a gene may contain one or more modifications in either the coding or the untranslated regions that could affect the biological activity or the chemical structure of the expression product, the rate of expression, or the manner of expression control. Such modifications include, but are not limited to, mutations, insertions, deletions, and substitutions of one or more nucleotides. In this regard, such modified genes may be referred to as "variants" of the "native" gene.

The term "host cell" refers to a cell that may be, or has been, used as a recipient for a recombinant vector or other transfer of polynucleotides, and includes the progeny of the original cell that has been transfected. The progeny of a single cell may not necessarily be completely identical in morphology or in genomic or total DNA complement as the original parent due to natural, accidental, or deliberate mutation.

Regulatory Elements

A nucleic acid molecule to be introduced via the approach of the present invention also can have a desired encoding segment linked operatively to a regulatory element, such as a promoter, a terminator, an enhancer and/or a signal sequence. A suitable promoter can be tissue-specific or even tumor-specific, as the therapeutic context dictates.

A promoter is "tissue-specific" when it is activated preferentially in a given tissue and, hence, is effective in driving expression, in the target tissue, of an operably linked structural sequence. The category of tissue-specific promoters includes, for example: the hepatocyte-specific promoter for albumin and $a_1$-antitrypsin, respectively; the elastase I gene control region, which is active in pancreatic acinar cells; the insulin gene control region, active in pancreatic beta cells; the mouse mammary tumor virus control region, which is active in testicular, breast, lymphoid and mast cells; the myelin basic protein gene control region, active in oligodendrocyte cells in the brain; and the gonadotropic releasing hormone gene control region, which is active in cells of the hypothalamus. See Frain et al. (1990), Ciliberto et al. (1985), Pinkert et al., (1987), Kelsey et al. (1987), Swift et al. (1984), MacDonald (1987), Hanahan, (1985), Leder et al. (1986), Readhead et al. (1987), and Mason et al. (1986).

There also are promoters that are expressed preferentially in certain tumor cells or in tumor cells per se, and that are useful for treating different cancers in accordance with the present invention. The class of promoters that are specific for cancer cells is illustrated by: the tyrosinase promoter, to target melanomas; the MUC1/Df3 promoter, to target breast carcinoma; the hybrid myoD enhancer/SV40 promoter, which targets expression to rhabdomyosarcoma (RMS); the carcinoembryonic antigen (CEA) promoter, which is specific for CEA-expressing cells such as colon cancer cells, and the hexokinase type II gene promoter, to target non-small cell lung carcinomas. See Hart (1996), Morton & Potter (1998), Kurane et al. (1998) and Katabi et al. (1999).

Promoters that are dependent on either RNA polymerase (pol) II or pol II are preferred promoters for gene transcription. Highly preferred promoters for shRNA transcription are the RNA III polymerase promoters H1 and U6.

A signal sequence can be used, according to the present invention, to effect secretion of an expression product or localization of an expression product to a particular cellular compartment. Thus, a therapeutic polynucleotide molecule that is delivered via intact killed bacterial cells may include a signal sequence, in proper reading frame, such that the expression product of interest is secreted by an engulfing cell or its progeny, thereby to influence surrounding cells, in keeping with the chosen treatment paradigm. Illustrative signal sequences include the haemolysin C-terminal secretion sequence, described in U.S. Pat. No. 5,143,830, the BAR1 secretion sequence, disclosed in U.S. Pat. No. 5,037,743, and the signal sequence portion of the zsig32 polypeptide, described in U.S. Pat. No. 6,025,197.

Reporter Elements

A nucleic acid molecule to be introduced via the approach of the present invention can include a reporter element. A reporter element confers on its recombinant host a readily detectable phenotype or characteristic, typically by encoding a polypeptide, not otherwise produced by the host, that can be detected, upon expression, by histological or in situ analysis, such as by in vivo imaging techniques. For example, a reporter element delivered by an intact killed bacterial cell, according to the present invention, could code for a protein that produces, in the engulfing host cell, a colorimetric or fluorometric change that is detectable by in situ analysis and that is a quantitative or semi-quantitative function of transcriptional activation. Illustrative of these proteins are esterases, phosphatases, proteases and other enzymes, the activity of which generates a detectable chromophore or fluorophore.

Preferred examples are *E. coli* β-galactosidase, which effects a color change via cleavage of an indigogenic substrate, indolyl-β-D-galactoside, and a luciferase, which oxidizes a long-chain aldehyde (bacterial luciferase) or a heterocyclic carboxylic acid (luciferin), with the concomitant release of light. Also useful in this context is a reporter element that encodes the green fluorescent protein (GFP) of the jellyfish, *Aequorea victoria*, as described by Prasher et al. (1995). The field of GFP-related technology is illustrated by two published PCT applications, WO 095/21191 (discloses a polynucleotide sequence encoding a 238 amino-acid GFP apoprotein, containing a chromophore formed from amino acids 65 through 67) and WO 095/21191 (discloses a modification of the cDNA for the apopeptide of *A. victoria* GFP, providing a peptide having altered fluorescent properties), and by a report of Heim et al. (1994) of a mutant GFP, characterized by a 4-to-6-fold improvement in excitation amplitude.

Another type of a reporter element is associated with an expression product that renders the recombinant killed bacterial cell resistant to a toxin. For instance, the neo gene protects a host against toxic levels of the antibiotic G418, while a gene encoding dihydrofolate reductase confers resistance to methotrexate, and the chloramphenicol acetyltransferase (CAT) gene bestows resistance to chloramphenicol.

Other genes for use as a reporter element include those that can transform a host killed bacterial cell to express distinguishing cell-surface antigens, e.g., viral envelope proteins such as HIV gp120 or herpes gD, which are readily detectable by immunoassays.

Drugs

Drugs useful in the invention may be any physiologically or pharmacologically active substance that produces a desired local or systemic effect in animals, particularly mammals and humans. Drugs may be inorganic or organic compounds, without limitation, including peptides, proteins, nucleic acids, and small molecules, any of which may be characterized or uncharacterized. They may be in various forms, such as unchanged molecules, molecular complexes, pharmacologically acceptable salts, such as hydrochloride, hydrobromide, sulfate, laurate, palmitate, phosphate, nitrite, nitrate, borate, acetate, maleate, tartrate, oleate, salicylate, and the like. For acidic drugs, salts of metals, amines or organic cations, for example, quaternary ammonium, can be used. Derivatives of drugs, such as bases, esters and amides also can be used. A drug that is water insoluble can be used in a form that is a water soluble derivative thereof, or as a base derivative thereof, which in either instance, or by its delivery, is converted by enzymes, hydrolyzed by the body pH, or by other metabolic processes to the original therapeutically active form.

Useful drugs include chemotherapeutic agents, immunosuppressive agents, cytokines, cytotoxic agents, nucleolytic compounds, radioactive isotopes, receptors, and pro-drug activating enzymes, which may be naturally occurring or produced by synthetic or recombinant methods.

Drugs that are affected by classical multidrug resistance have particular utility in the invention, such as *vinca* alkaloids (e.g., vinblastine and vincristine), the anthracyclines (e.g., doxorubicin and daunorubicin), RNA transcription inhibitors (e.g., actinomycin-D) and microtubule stabilizing drugs (e.g., paclitaxel). (Ambudkar et al., 1999).

In general, cancer chemotherapy agents are preferred drugs. Useful cancer chemotherapy drugs include nitrogen mustards, nitrosorueas, ethyleneimine, alkane sulfonates, tetrazine, platinum compounds, pyrimidine analogs, purine analogs, antimetabolites, folate analogs, anthracyclines, taxanes, *vinca* alkaloids, topoisomerase inhibitors and hormonal agents. Exemplary chemotherapy drugs are Actinomycin-D, Alkeran, Ara-C, Anastrozole, Asparaginase, BiCNU, Bicalutamide, Bleomycin, Busulfan, Capecitabine, Carboplatin, Carboplatinum, Carmustine, CCNU, Chlorambucil, Cisplatin, Cladribine, CPT-11, Cyclophosphamide, Cytarabine, Cytosine arabinoside, Cytoxan, Dacarbazine, Dactinomycin, Daunorubicin, Dexrazoxane, Docetaxel, Doxorubicin, DTIC, Epirubicin, Ethyleneimine, Etoposide, Floxuridine, Fludarabine, Fluorouracil, Flutamide, Fotemustine, Gemcitabine, Herceptin, Hexamethylamine, Hydroxyurea, Idarubicin, Ifosfamide, Irinotecan, Lomustine, Mechlorethamine, Melphalan, Mercaptopurine, Methotrexate, Mitomycin, Mitotane, Mitoxantrone, Oxaliplatin, Paclitaxel, Pamidronate, Pentostatin, Plicamycin, Procarbazine, Rituximab, Steroids, Streptozocin, STI-571, Streptozocin, Tamoxifen, Temozolomide, Teniposide, Tetrazine, Thioguanine, Thiotepa, Tomudex. Topotecan, Treosulphan, Trimetrexate, Vinblastine, Vincristine, Vindesine, Vinorelbine, VP-16, and Xeloda.

Useful cancer chemotherapy drugs also include alkylating agents such as Thiotepa and cyclosphosphamide; alkyl sulfonates such as Busulfan, Improsulfan and Piposulfan; aziridines such as Benzodopa, Carboquone, Meturedopa, and Uredopa; ethylenimines and methylamelamines including altretamine, triethylenemelamine, trietylenephosphoramide, triethylenethiophosphaoramide and trimethylolomelamine; nitrogen mustards such as Chlorambucil, Chlornaphazine, Cholophosphamide, Estramustine, Ifosfamide, mechlorethamine, mechlorethamine oxide hydrochloride, Melphalan, Novembichin, Phenesterine, Prednimustine, Trofusfamide, uracil mustard; nitroureas such as Cannustine, Chlorozotocin, Fotemustine, Lomustine, Nimustine, and Ranimustine; antibiotics such as Aclacinomysins, Actinomycin, Authramycin, Azaserine, Bleomycins, Cactinomycin, Calicheamicin, Carabicin, Carminomycin, Carzinophilin, Chromoinycins, Dactinomycin, Daunorubicin, Detorubicin, 6-diazo-5-oxo-L-norleucine, Doxorubicin, Epirubicin, Esorubicin, Idambicin, Marcellomycin, Mitomycins, mycophenolic acid, Nogalamycin, Olivomycins, Peplomycin, Potfiromycin, Puromycin. Quelamycin, Rodorubicin, Streptonigrin, Streptozocin, Tubercidin, Ubenimex, Zinostatin, and Zorubicin; anti-metabolites such as Methotrexate and 5-fluorouracil (5-FU); folic acid analogues such as Denopterin, Methotrexate, Pteropterin, and Trimetrexate; purine analogs such as Fludarabine, 6-mercaptopurine, Thiamiprine, and Thioguanine; pyrimidine analogs such as Ancitabine, Azacitidine, 6-azauridine, Carmofur, Cytarabine, Dideoxyuridine, Doxifluridine, Enocitabine, Floxuridine, and 5-FU; androgens such as Calusterone, Dromostanolone Propionate, Epitiostanol, Rnepitiostane, and Testolactone; anti-adrenals such as aminoglutethimide, Mitotane, and Trilostane; folic acid replenisher such as frolinic acid; aceglatone; aldophosphamide glycoside; aminolevulinic acid; Amsacrine; Bestrabucil; Bisantrene; Edatraxate; Defofamine; Demecolcine; Diaziquone; Elfomithine; elliptinium acetate; Etoglucid; gallium nitrate; hydroxyurea; Lentinan; Lonidamine; Mitoguazone; Mitoxantrone; Mopidamol; Nitracrine; Pentostatin; Phenamet; Pirarubicin; podophyllinic acid; 2-ethylhydrazide; Procarbazine; PSK®; Razoxane; Sizofrran; Spirogermanium; tenuazonic acid; triaziquone; 2, 2',2"-trichlorotriethylamine; Urethan; Vindesine; Dacarbazine; Mannomustine; Mitobronitol; Mitolactol; Pipobroman; Gacytosine; Arabinoside ("Ara-C"); cyclophosphamide; thiotEPa; taxoids, e.g., Paclitaxel (TAXOL®, Bristol-Myers Squibb Oncology, Princeton, N.J.) and Doxetaxel (TAXOTERE®, Rhone-Poulenc Rorer, Antony, France); Chlorambucil; Gemcitabine; 6-thioguanine; Mercaptopurine; Methotrexate; platinum analogs such as Cisplatin and Carboplatin; Vinblastinc; platinum; etoposide (VP-16); Ifosfamide; Mitomycin C; Mitoxantrone; Vincristine; Vinorelbine; Navelbino; Novantrone; Teniposide; Daunomycin; Aminopterin; Xeloda; Ibandronate; CPT-11; topoisomerase inhibitor RFS 2000; ditluoromethylornithine (DMFO); retinoic acid; Esperamicins; Capecitabine; and pharmaceutically acceptable salts, acids or derivatives of any of the above. Also included are anti-hormonal agents that act to regulate or inhibit hormone action on tumors such as anti-estrogens including for example Tamoxifen, Raloxifene, aromatase inhibiting 4(5)-imidazoles, 4 Hydroxytamoxifen, Trioxifene, Keoxifene, Onapristone, And Toremifene (Fareston); and anti-androgens such as Flutamide, Nilutamide, Bicalutamide, Leuprolide, and Goserelin; and pharmaceutically acceptable salts, acids or derivatives of any of the above.

Useful drugs also include cytokines. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoictin (TPO); nerve growth factors such as NGF-β; platelet growth factor; transforming growth factors (TGFs) such as TGF-α and TGF-β; insulin-like growth factor-I and -II; erythropoietin (EPO); osteoinductive factors; interferons such as interferon-α, -β and -γ; colony stimulating factors (CSFs) such as macrophage-CSF (M-CSF); granulocyte-macrophage-CSF (GM-CSF); and granulocyte-CSF (GCSF); interleukins (ILs) such as IL-1, IL-1a, IL-2, IL-3, IL-4, IL-5, IL-6, IL-7, IL-8, IL-9, IL-11, IL-12, IL-15; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The drugs may be prodrugs, subsequently activated by a prodrug-activating enzyme that converts a prodrug like a peptidyl chemotherapeutic agent to an active anti-cancer drug. See, e.g., WO 88/07378; WO 81/01145; U.S. Pat. No. 4,975,278. In general, the enzyme component includes any enzyme capable of acting on a prodrug in such a way so as to covert it into its more active, cytotoxic form.

For purposes of the invention, an intact killed bacterial cell contains a drug if it contains a nucleic acid encoding a drug. For example, a plasmid may encode a drug that is expressed inside of mammalian target cells. This makes possible endogenous delivery of drugs, which has advantages over the transient nature of exogenous delivery.

Functional Nucleic Acids

"Functional nucleic acid" refers to a nucleic acid molecule that, upon introduction into a host cell, specifically interferes with expression of a protein. In general, functional nucleic acid molecules have the capacity to reduce expression of a protein by directly interacting with a transcript that encodes the protein. Regulatory RNA, such as siRNA, shRNA, short RNAs (typically less than 400 bases in length), micro-RNAs (miRNAs), ribozymes and decoy RNA, and antisense nucleic acids constitute exemplary functional nucleic acids.

"Regulatory RNA" denotes a category inclusive of RNAs that affect expression by RNA interference, suppression of gene expression, or another mechanism. Accordingly, in addition to shRNA, siRNA, miRNA, and antisense ssRNA, the category of regulatory RNAs includes ribozymes and decoy RNAs, inter alia.

Targets of Functional Nucleic Acids

Functional nucleic acids of the invention preferably target the gene or transcript of a protein that promotes drug resistance, inhibits apoptosis or promotes a neoplastic phenotype. Successful application of functional nucleic acid strategies in these contexts have been achieved in the art, but without the benefits of killed bacterial cell vectors. See, e.g., Sioud (2004), Caplen (2003), Wu et al. (2003), Nieth et al. (2003), Caplen and Mousses (2003), Duxbury et al. (2004), Yague et al. (2004), Duan et al. (2004).

Proteins that contribute to drug resistance constitute preferred targets of functional nucleic acids. The proteins may contribute to acquired drug resistance or intrinsic drug resistance. When diseased cells, such as tumor cells, initially respond to drugs, but become refractory on subsequent treatment cycles, the resistant phenotype is acquired. Useful targets involved in acquired drug resistance include ATP binding cassette transporters such as P-glycoprotein (P-gp, P-170, PGY 1, MDR1, ABCB1, MDR-associated protein, Multidrug resistance protein 1), MDR-2 and MDR-3. MRP2 (multi-drug resistance associated protein), BCR-ABL (breakpoint cluster region—Abelson protooncogene), a STI-571 resistance-associated protein, lung resistance-related protein, cyclooxygenase-2, nuclear factor kappa, XRCC1 (X-ray cross-complementing group 1), ERCC1 (Excision cross-complementing gene), GSTP1 (Glutathione S-transferase), mutant 1-tubulin, and growth factors such as IL-6 are additional targets involved in acquired drug resistance. When previously untreated cells fail to respond to one or more drugs, the resistant phenotype is intrinsic. An example of a protein contributing to intrinsic resistance is LRP (lung resistance-related protein).

Particularly useful targets that contribute to drug resistance include ATP binding cassette transporters such as P-glycoprotein, MDR-2, MDR-3, BCRP, APT11a and LRP.

Useful targets also include proteins that contribute to apoptosis resistance. These include Bcl-2 (B cell leukemia/lymphoma), Bcl-$X_L$, A1/Bfl 1, focal adhesion kinase, Dihydrodiol dehydrogenase and p53 mutant protein.

Useful targets further include oncogenic and mutant tumor suppressor proteins. Examples include β-Catenin, PKC-α (protein kinase C), C-RAF, K-Ras (V12), DP97 Dead box RNA helicase, DNMT1 (DNA methyltransferase 1), FLIP (Flice-like inhibitory protein), C-Sfc, 53BPl, Polycomb group protein EZH2 (Enhancer of zeste homologue), ErbB1, HPV-16 E5 and E7 (human papillomavirus early 5 and early 7), Fortilin & MCl1P (Mycloid cell leukemia 1 protein), DIP13α (DDC interacting protein 13a), MBD2 (Methyl CpG binding domain), p21, KLF4 (Kruppel-like factor 4), tpt/TCTP (Translational controlled tumor protein), SPK1 & SPK2 (Sphingosine kinase), P300, PLK1 (Polo-like kinase-1), Trp53, Ras, ErbB1, VEGF (Vascular endothelial growth factor), BAG-1 (BCL2-associated athanogene 1), MRP2, BCR-ABL, STI-571 resistance-associated protein, lung resistance-related protein, cyclooxygenase-2, nuclear factor kappa, XRCC1, ERCC1, GSTP1, mutant β-tubulin, and growth factors.

With regard to HIV infection, targets include HIV-Tat, HIV-Rev, HIV-Vif, HIV-Nef, HIV-Gag, HIV-Env, LTR, CD4, CXCR4 (chemokine receptor) and CCR5 (chemokine receptor).

Because of tumor cell heterogeneity, a number of different drug resistance or apoptosis resistance pathways may be operational in target cells. Therefore, the functional nucleic acids used in methods of the invention may require change over time. For instance, if biopsy samples reveal new mutations that result in acquired drug resistance, specific siRNAs can be designed and encoded on a suitable expression plasmid, which is transformed into a killed bacterial cell-producing bacterial strain, which is used to produce recombinant killed bacterial cells that are administered to address the acquired drug resistance.

siRNA Molecule

Short interfering RNA (siRNA) molecules are useful for performing RNA interference (RNAi), a post-transcriptional gene silencing mechanism. According to this invention, siRNAs refer to double-stranded RNA molecules or single-stranded hairpin RNA molecules from about 10 to about 30 nucleotides long, which are named for their ability specifically to interfere with protein expression. Preferably, double-stranded siRNA molecules are 12-28 nucleotides long, more preferably 15-25 nucleotides long, still more preferably 19-23 nucleotides long and most preferably 21-23 nucleotides long. Therefore, preferred siRNA molecules are 12, 13, 14, 15, 16, 17, 18, 19, 20, 21, 22, 23, 24, 25, 26, 27 28 or 29 nucleotides in length.

The length of one strand designates the length of a double-stranded siRNA molecule. For instance, a double-stranded siRNA that is described as 21 ribonucleotides long (a 21-mer) could comprise two opposite strands of RNA that anneal together for 19 contiguous base pairings. The two remaining ribonucleotides on each strand would form an "overhang." When an siRNA contains two strands of different lengths, the longer of the strands designates the length of the siRNA. For instance, a dsRNA containing one strand that is 21 nucleotides long and a second strand that is 20 nucleotides long, constitutes a 21-mer.

Double-stranded siRNAs that comprise an overhang are desirable. The overhang may be at the 5' or the 3' end of a strand. Preferably, it is at the 3' end of the RNA strand. The length of an overhang may vary, but preferably is about 1 to about 5 bases, and more preferably is about 2 nucleotides long. Preferably, the siRNA of the present invention will comprise a 3' overhang of about 2 to 4 bases. More preferably, the 3' overhang is 2 ribonucleotides long. Even more preferably, the 2 ribonucleotides comprising the 3' overhang are uridine (U).

siRNAs of the invention are designed to interact with a target ribonucleotide sequence, meaning they complement a target sequence sufficiently to hybridize to the target sequence. In one embodiment, the invention provides an siRNA molecule comprising a ribonucleotide sequence at least 70%, 75%, 80%, 85% or 90% identical to a target ribonucleotide sequence or the complement of a target ribonucleotide sequence. Preferably, the siRNA molecule is at least 90%, 95%, 96%, 97%, 98%, 99% or 100% identical to the target ribonucleotide sequence or the complement of the target ribonucleotide sequence. Most preferably, an siRNA will be 100% identical to the target nucleotide sequence or the complement of the ribonucleotide sequence. However, siRNA molecules with insertions, deletions or single point mutations relative to a target may also be effective.

Tools to assist siRNA design are readily available to the public. For example, a computer-based siRNA design tool is available on the internet at www.dharmacon.com.

Relatedly, shRNAs comprise a single strand of RNA that forms a stem-loop structure, where the stem consists of the complementary sense and antisense strands that comprise a double-stranded siRNA, and the loop is a linker of varying size. The stem structure of shRNAs generally is from about 10 to about 30 nucleotides long. Preferably, the stem of shRNA molecules are 12-28 nucleotides long, more preferably 15-25 nucleotides long, still more preferably 19-23 nucleotides long and most preferably 21-23 nucleotides long. Therefore, preferred shRNA molecules comprise stems that are 12, 13, 14, 15, 16, 17, 18, 19, 20, 21, 22, 23, 24, 25, 26, 27 28 or 29 nucleotides in length.

Ribozymes

Ribozymes are RNA molecules having an enzymatic activity that can repeatedly cleave other RNA molecules in a nucleotide base sequence-specific manner. Such enzymatic RNA molecules may be targeted to virtually any RNA transcript, and efficient cleavage achieved in vitro.

Six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic polynucleotides act by first binding to a target RNA. Such binding occurs through the target binding portion of a enzymatic polynucleotide which is held in close proximity to an enzymatic portion of the molecule that acts to cleave the target RNA. Thus, the enzymatic polynucleotide first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic polynucleotide has bound and cleaved its RNA target, it is released from that RNA to search for another target and can repeatedly bind and cleave new targets.

The enzymatic nature of a ribozyme is advantageous. Because a single ribozyme molecule is able to cleave many molecules of target RNA, effective concentrations of ribozyme can be quite low.

Useful ribozymes may comprise one of several motifs, including hammerhead (Rossi et al. (1992)), hairpin (Hampel and Tritz, (1989), Hampel et al. (1990)), hepatitis delta virus motif (Perrotta and Been (1992), group I intron (U.S. Pat. No. 4,987,071), RNaseP RNA in association with an RNA guide sequence (Guerrier-Takada et al. (1983)), and Neurospora VS RNA (Saville & Collins (1990); Saville & Collins (1991); Collins & Olive (1993)). These specific motifs are not limiting, as all that is important in a ribozyme of this invention is that it has a specific substrate binding site that is complementary to one or more target RNA regions, and that it have nucleotide sequences within or surrounding that substrate binding site which impart an RNA cleaving activity to the molecule.

Ribozymes of the invention may comprise modified oligonucleotides (e.g., for improved stability, targeting, etc.). Nucleic acid sequences encoding the ribozymes may be under the control of a strong constitutive promoter, such as, for example, RNA Polymerase II or RNA Polymerase III promoter, so that transfected cells will produce sufficient quantities of the ribozyme to destroy target endogenous messages and inhibit translation.

Antisense Oligonucleotides

Antisense oligonucleotides of the invention specifically hybridize with a nucleic acid encoding a protein, and interfere with transcription or translation of the protein. In one embodiment, an antisense oligonucleotide targets DNA and interferes with its replication and/or transcription. In another embodiment, an antisense oligonucleotide specifically hybridizes with RNA, including pre-mRNA and mRNA. Such antisense oligonucleotides may affect, for example, translocation of the RNA to the site of protein translation, translation of protein from the RNA, splicing of the RNA to yield one or more mRNA species, and catalytic activity that may be engaged in or facilitated by the RNA. The overall effect of such interference is to modulate, decrease, or inhibit target protein expression.

"Oligonucleotide" refers to a polynucleotide comprising, for example, from about 10 nucleotides (nt) to about 1000 nt. Oligonucleotides for use in the invention are preferably from about 10 nt to about 150 nt. The oligonucleotide may be a naturally occurring oligonucleotide or a synthetic oligonucleotide. Oligonucleotides may be modified.

"Modified oligonucleotide" and "Modified polynucleotide" refer to oligonucleotides or polynucleotides with one or more chemical modifications at the molecular level of the natural molecular structures of all or any of the bases, sugar moieties, internucleoside phosphate linkages, as well as to molecules having added substitutions or a combination of modifications at these sites. The internucleoside phosphate linkages may be phosphodiester, phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone internucleotide linkages, or 3'-3', 5'-3', or 5'-5' linkages, and combinations of such similar linkages. The phosphodiester linkage may be replaced with a substitute linkage, such as phosphorothioate, methylamino, methylphosphonate, phosphoramidate, and guanidine, and the ribose subunit of the polynucleotides may also be substituted (e.g., hexose phosphodiester; peptide nucleic acids). The modifications may be internal (single or repeated) or at the end(s) of the oligonucleotide molecule, and may include additions to the molecule of the internucleoside phosphate linkages, such as deoxyribose and phosphate modifications which cleave or crosslink to the opposite chains or to associated enzymes or other proteins. The terms "modified oligonucleotides" and "modified polynucleotides" also include oligonucleotides or polynucleotides comprising modifications to the sugar moieties (e.g., 3'-substituted ribonucleotides or deoxyribonucleotide monomers), any of which are bound together via 5' to 3' linkages.

There are several sites within a gene that may be utilized in designing an antisense oligonucleotide. For example, an antisense oligonucleotide may bind the region encompassing the translation initiation codon, also known as the start codon, of the open reading frame. In this regard, "start codon and "translation initiation codon" generally refer to the portion of such mRNA or gene that encompasses from at least about 25 to at least about 50 contiguous nucleotides in either direction (i.e., 5' or 3') from a translation initiation codon.

Another site for antisense interaction to occur is the termination codon of the open reading frame. The terms "stop codon region" and "translation termination codon region" refer generally to a portion of such a mRNA or gene that encompasses from at least about 25 to at least about 50 contiguous nucleotides in either direction form a translation termination codon.

The open reading frame or coding region also may be targeted effectively. The open reading frame is generally understood to refer to the region between the translation initiation codon and the translation termination codon. Another target region is the 5' untranslated region, which is the portion of a mRNA in the 5' direction from the translation initiation codon. It includes the nucleotides between the 5' cap site and the translation initiation codon of a mRNA or corresponding nucleotides on the gene.

Similarly, the 3' untranslated region may be used as a target for antisense oligonucleotides. The 3' untranslated region is that portion of the mRNA in the 3' direction from the translation termination codon, and thus includes the nucleotides between the translation termination codon and the 3' end of a mRNA or corresponding nucleotides of the gene.

An antisense oligonucleotide may also target the 5' cap region of an mRNA. The 5' cap comprises an N7-methylated guanosine residue joined to the 5'-most residue of the mRNA via 5'-5' triphosphate linkage. The 5' cap region is considered to include the 5' cap structure itself as well as the first 50 nucleotides adjacent to the cap.

Although some eukaryotic mRNA transcripts are directly translated, many contain one or more intron regions, which are excised from a transcript before it is translated. The remaining (and therefore translated) exon regions are spliced together to form a continuous mRNA sequence. mRNA splice sites, i.e., intron-exon junctions, represent possible target regions, and are particularly useful in situations where aberrant splicing is implicated in disease, or where an overproduction of a particular mRNA splice product is implicated in disease. Moreover, aberrant fusion junctions due to rearrangements or deletions are also possible targets for antisense oligonucleotides.

With these various target sites in mind, antisense oligonucleotides that are sufficiently complementary to the target polynucleotides must be chosen. "Complementary" refers to the topological compatibility or matching together of the interacting surfaces of two molecules. There must be a sufficient degree of complementarity or precise pairing such that stable and specific binding occurs between the oligonucleotide and the polynucleotide target. Importantly, the sequence of an antisense oligonucleotide need not be 100% complementary to that of its target polynucleotide to be specifically hybridizable. An antisense oligonucleotide is specifically hybridizable when binding of the antisense oligonucleotide to the target polynucleotide interferes with the normal function of the target polynucleotide to cause a loss of utility, and there is a sufficient degree of complementarity to avoid non-specific binding of the antisense oligonucleotide to non-target sequences under conditions in which specific binding is desired, i.e., under physiological conditions in the case of in vivo assays or therapeutic treatment, and in the case of in vitro assays, under conditions in which the assays are performed.

The antisense oligonucleotides may be at least about 8 nt to at least about 50 nt in length. In one embodiment, the antisense oligonucleotides may be about 12 to about 30 nt in length.

The antisense oligonucleotides used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Nucleic Acids Encoding Functional Nucleic Acids

For purposes of the invention, an intact killed bacterial cell contains a functional nucleic acid if it contains a nucleic acid encoding a functional nucleic acid. For example, a plasmid may encode a functional nucleic acid that is expressed inside of mammalian target cells. This makes possible endogenous delivery of functional nucleic acids, which has advantages over the transient nature of exogenous delivery.

Thus, recombinant intact killed bacterial cells may carry plasmid DNA encoding one or more siRNA sequences aimed at silencing drug resistance or apoptosis resistance genes. Using killed bacterial cells that encode multiple functional nucleic acids, it is possible to treat cells that express multiple drug resistance mechanisms. Different siRNA sequences can be expressed individually from different promoters. For example, siRNA targeting Pgp mRNA can be expressed from the U6 promoter and siRNA targeting Bcl-2 mRNA can be expressed from the H1 promoter. These multiple expression cassettes preferably are carried on a single plasmid, but may also be on different plasmids. Different siRNA sequences also can be expressed from a single promoter, where the recombinant plasmid carries an expression cassette comprised of multiple siRNA-encoding sequences, which are linked together via non-coding polynucleotide sequences. A single gene transcription terminator can be placed downstream of the complete expression cassette.

In one strategy, a plasmid encodes the sense and antisense strands of an siRNA as two independent transcripts that, after expression within a target cell, hybridize to form functional siRNA duplexes. In a second preferred strategy, a plasmid encodes one or more siRNAs that each are expressed as a single transcript that forms a short hairpin RNA stem-loop structure. The hairpin structure may be processed by a Dicer enzyme into functional siRNA.

Pharmaceutically Acceptable Carriers

"Pharmaceutically acceptable" refers to physiological compatibility. A pharmaceutically acceptable carrier or excipient does not abrogate biological activity of the composition being administered, is chemically inert and is not toxic to the organism in which it is administered.

Endotoxin

"Endotoxin" refers to free lipopolysaccharide (LPS). Accordingly, a composition that is "free of endotoxin" lacks LPS that is unassociated with a bacterial cell membrane. A composition that is "essentially free of endotoxin" lacks a sufficient quantity or concentration of LPS to cause toxicity in a mammal, such as a human. Endotoxin/LPS that is unassociated with a bacterial cell membrane also is referred to as "free endotoxin."

Endotoxin can be eliminated from a composition via filtration through a 0.2 µm filter. Free endotoxin and endotoxin micelles are smaller than 0.2 µm and hence are readily filtered from a composition that retains killed bacterial cells, which are larger than 0.2 µm. Additionally, anti-lipid A monoclonal antibodies can be used to bind to free endotoxin. The anti-lipid A monoclonal antibodies can be bound to a solid support such as an affinity chromatography column or magnetic beads via their Fc component, leaving the lipid A-binding Fab fragments free to bind to free LPS.

Bispecific Ligands

Compositions of the invention also may comprise one or more bispecific ligands. Ligands useful in the invention include any agent that binds to a surface component on a target cell and to a surface component on a killed bacterial cell. Preferably, the surface component on a target cell is a receptor, especially a receptor capable of mediating endocytosis. The ligands may comprise a polypeptide and/or carbohydrate component. Antibodies are preferred ligands. For example, a bispecific antibody that carries dual specificities for a surface component on bacterially derived intact killed bacterial cells and for a surface component on target mammalian cells, can be used efficiently to target the killed bacterial cells to the target mammalian cells in vitro and in vivo. The category of useful ligands also includes receptors, enzymes, binding peptides, fusion/chimeric proteins and small molecules.

The selection of a particular ligand is made on two primary criteria: (i) specific binding to one or more domains on the surface of intact killed bacterial cells and (ii) specific binding to one or more domains on the surface of the target cells. Thus, ligands preferably have a first arm that carries specificity for a bacterially derived intact killed bacterial cell surface structure and a second arm that carries specificity for a mammalian cell surface structure. Each of the first and second arms may be multivalent. Preferably, each arm is monospecific, even if multivalent.

For binding to bacterially derived killed bacterial cells, it is desirable for one arm of the ligand to be specific for the O-polysaccharide component of a lipopolysaccharide found on the parent bacterial cell. Other killed bacterial cell surface structures that can be exploited for ligand binding include cell surface-exposed polypeptides and carbohydrates on outer membranes, such as pilli, fimbrae, outer-membrane protein and flagella cell surface exposed peptide segments.

For binding to target cells, one arm of the ligand is specific for a surface component of a mammalian cell. Such components include cell surface proteins, peptides and carbohydrates, whether characterized or uncharacterized. Cell surface receptors, especially those capable of activating receptor-mediated endocytosis, are desirable cell surface components for targeting. Such receptors, if over-expressed on the target cell surface, confer additional selectivity for targeting the cells to be treated, thereby reducing the possibility for delivery to non-target cells.

By way of example, one may target tumor cells, metastatic cells, vasculature cells, such as endothelial cells and smooth muscle cells, lung cells, kidney cells, blood cells, bone marrow cells, brain cells, liver cells, and so forth, or precursors of any selected cell by selecting a ligand that specifically binds a cell surface receptor motif on the desired cells. Examples of cell surface receptors include carcinoembryonic antigen (CEA), which is overexpressed in most colon, rectum, breast, lung, pancreas and gastrointestinal tract carcinomas (Marshall, 2003); heregulin receptors (HER-2, neu or c-erbB-2), which is frequently overexpressed in breast, ovarian, colon, lung, prostate and cervical cancers (Hung et al., 2000); epidermal growth factor receptor (EGFR), which is highly expressed in a range of solid tumors including those of the breast, head and neck, non-small cell lung and prostate (Salomon et al., 1995); asialoglycoprotein receptor (Stockert, 1995); transferrin receptor (Singh, 1999); serpin enzyme complex receptor, which is expressed on hepatocytes (Ziady et al., 1997); fibroblast growth factor receptor (FGFR), which is overexpressed on pancreatic ductal adenocarcinoma cells (Kleeff et al., 2002); vascular endothelial growth factor receptor (VEGFR), for anti-angiogenesis gene therapy (Becker et al., 2002 and Hoshida et al., 2002); folate receptor, which is selectively overexpressed in 90% of nonmucinous ovarian carcinomas (Gosselin and Lee, 2002); cell surface glycocalyx (Batra et al., 1994); carbohydrate receptors (Thurnher et al., 1994); and polymeric immunoglobulin receptor, which is useful for gene delivery to respiratory epithelial cells and attractive for treatment of lung diseases such as Cystic Fibrosis (Kaetzel et al., 1997).

Preferred ligands comprise antibodies and/or antibody derivatives. As used herein, the term "antibody" encompasses an immunoglobulin molecule obtained by in vitro or in vivo generation of an immunogenic response. The term "antibody" includes polyclonal, monospecific and monoclonal antibodies, as well as antibody derivatives, such as single-chain antibody fragments (scFv). Antibodies and antibody derivatives useful in the present invention also may be obtained by recombinant DNA techniques.

Wild type antibodies have four polypeptide chains, two identical heavy chains and two identical light chains. Both types of polypeptide chains have constant regions, which do not vary or vary minimally among antibodies of the same class, and variable regions. Variable regions are unique to a particular antibody and comprise an antigen binding domain that recognizes a specific epitope. The regions of the antigen binding domain that are most directly involved in antibody binding are "complementarity-determining regions" (CDRs).

The term "antibody" also encompasses derivatives of antibodies, such as antibody fragments that retain the ability to specifically bind to antigens. Such antibody fragments include Fab fragments (a fragment that contains the antigen-binding domain and comprises a light chain and part of a heavy chain bridged by a disulfide bond), Fab' (an antibody fragment containing a single antigen-binding domain comprising a Fab and an additional portion of the heavy chain through the hinge region, P(ab')2 (two Fab' molecules joined by interchain disulfide bonds in the hinge regions of the heavy chains), a bispecific Fab (a Fab molecule having two antigen binding domains, each of which may be directed to a different epitope), and an scFv (the variable, antigen-binding determinative region of a single light and heavy chain of an antibody linked together by a chain of amino acids).

When antibodies, including antibody fragments, constitute part or all of the ligands, they preferably are of human origin or are modified to be suitable for use in humans. So-called "humanized antibodies" are well known in the art. See, e.g., Osbourn et al., 2003. They have been modified by genetic manipulation and/or in vitro treatment to reduce their antigenicity in a human. Methods for humanizing antibodies are described, e.g., in U.S. Pat. Nos. 6,639,055, 5,585,089, and 5,530,101. In the simplest case, humanized antibodies are formed by grafting the antigen-binding loops, known as complementarity-determining regions (CDRs), from a mouse mAb into a human IgG. See Jones et al., 1986; Riechmann et al., 1988; and Verhoeyen et al., 1988. The generation of high-affinity humanized antibodies, however, generally requires the transfer of one or more additional residues from the so-called framework regions (FRs) of the mouse parent mAb. Several variants of the humanization technology also have been developed. See Vaughan et al., 1998.

Human antibodies, rather than "humanized antibodies," also may be employed in the invention. They have high affinity for their respective antigens and are routinely obtained from very large, single-chain variable fragments (scFvs) or Fab phage display libraries. See Griffiths et al., 1994; Vaughan et al., 1996; Sheets et al., 1998; de Haard et al., 1999; and Knappik et al., 2000.

Useful ligands also include bispecific single chain antibodies, which typically are recombinant polypeptides consisting of a variable light chain portion covalently attached through a linker molecule to a corresponding variable heavy chain portion. See U.S. Pat. Nos. 5,455,030, 5,260,203, and 4,496,778. Bispecific antibodies also can be made by other methods. For example, chemical heteroconjugates can be created by chemically linking intact antibodies or antibody fragments of different specificities. See Karpovsky et al., 1984. However, such heteroconjugates are difficult to make in a reproducible manner and are at least twice as large as normal monoclonal antibodies. Bispecific antibodies also can be created by disulfide exchange, which involves enzymatic cleavage and reassociation of the antibody fragments. See Glennie et al., 1987.

Because Fab and scFv fragments are monovalent they often have low affinity for target structures. Therefore, preferred ligands made from these components are engineered into dimeric, trimeric or tetrameric conjugates to increase functional affinity. See Tomlinson and Holliger, 2000; Carter, 2001; Hudson and Souriau, 2001; and Todorovska et al., 2001. Such conjugate structures may be created by chemical and/or genetic cross-links.

Bispecific ligands of the invention preferably are monospecific at each end, i.e., specific for a single component on killed bacterial cells at one end and specific for a single component on target cells at the other end. The ligands may be multivalent at one or both ends, for example, in the form of so-called diabodies, triabodies and tetrabodies. See Hudson and Souriau, 2003. A diabody is a bivalent dimer formed by a non-covalent association of two scFvs, which yields two Fv binding sites. Likewise, a triabody results from the formation of a trivalent trimer of three scFvs, yielding three binding sites, and a tetrabody results from the formation of a tetravalent tetramer of four scFvs, yielding four binding sites.

Several humanized, human, and mouse monoclonal antibodies and fragments thereof that have specificity for receptors on mammalian cells have been approved for human therapeutic use, and the list is growing rapidly. See Hudson and Souriau, 2003. An example of such an antibody that can be used to form one arm of a bispecific ligand has specificity for HER2: Herceptin™; Trastuzumab.

Antibody variable regions also can be fused to a broad range of protein domains. Fusion to human immunoglobulin domains such as IgG1 CH3 both adds mass and promotes dimerization. See Hu et al., 1996. Fusion to human Ig hinge-Fc regions can add effector functions. Also, fusion to heterologous protein domains from multimeric proteins promotes multimerization. For example, fusion of a short scFv to short amphipathic helices has been used to produce miniantibodies. See Pack and Pluckthun, 1992. Domains from proteins that form heterodimers, such as fos/jun, can be used to produce bispecific molecules (Kostelny et al., 1992) and, alternately, homodimerization domains can be engineered to form heterodimers by engineering strategies such as "knobs into holes" (Ridgway et al., 1996). Finally, fusion protein partners can be selected that provide both multimerization as well as an additional function, e.g. streptavidin. See Dubel et al., 1995.

Additional Compositions

In one embodiment, the composition comprises a killed bacterial cell that contains a functional nucleic acid molecule and a drug. The functional nucleic acid molecule may be one that targets the transcript of a protein that contributes to drug resistance. Preferably, the functional nucleic acid molecule targets the transcript of a protein that contributes to resistance against the same drug in the composition. The drug may be contained within a killed bacterial cell, even the same killed bacterial cell as the functional nucleic acid molecule, but need not be so contained.

Delivery Methods to Phagocytosis- or Endocytosis-Competent Cells

In another aspect, the invention provides for delivery by means of bringing bacterially derived killed bacterial cells into contact with mammalian cells that are phagocytosis- or endocytosis-competent. Such mammalian cells, which are capable of engulfing parent bacterial cells in the manner of intracellular bacterial pathogens, likewise engulf the killed bacterial cells, which release their payload into the cytoplasm of the mammalian cells. This delivery approach can be effected without the use of targeting ligands.

A variety of mechanisms may be involved in the engulfing of killed bacterial cells by a given type of cell, and the present invention is not dependent on any particular mechanism in this regard. For example, phagocytosis is a well-documented process in which macrophages and other phagocyte cells, such as neutrophils, ingest particles by extending pseudopodia over the particle surface until the particle is totally enveloped. Although described as "non-specific" phagocytosis, the involvement of specific receptors in the process has been demonstrated. See Wright & Jong (1986); Speert et al. (1988).

Thus, one form of phagocytosis involves interaction between surface ligands and ligand-receptors located at the membranes of the pseudopodia (Shaw and Griffin, 1981). This attachment step, mediated by the specific receptors, is thought to be dependent on bacterial surface adhesins. With respect to less virulent bacteria, such as non-enterotoxigenic *E. coli*, phagocytosis also may occur in the absence of surface ligands for phagocyte receptors. See Pikaar et al. (1995), for instance. Thus, the present invention encompasses but is not limited to the use of killed bacterial cells that either possess or lack surface adhesins, in keeping with the nature of their parent bacterial cells, and are engulfed by phagocytes (i.e., "phagocytosis-competent" host cells), of which neutrophils and macrophages are the primary types in mammals.

Another engulfing process is endocytosis, by which intracellular pathogens exemplified by species of *Salmonella, Escherichia, Shigella, Helicobacter, Pseudomonas* and *Lactobacilli* gain entry to mammalian epithelial cells and replicate there. Two basic mechanisms in this regard are Clathrin-dependent receptor-mediated endocytosis, also known as "coated pit endocytosis" (Riezman, 1993), and Clathrin-independent endocytosis (Sandvig & Deurs, 1994). Either or both may be involved when an engulfing-competent cell that acts by endocytosis (i.e., an "endocytosis-competent" host cell) engulfs killed bacterial cells in accordance with the invention. Representative endocytosis-competent cells are breast epithelial cells, enterocytes in the gastrointestinal tract, stomach epithelial cells, lung epithelial cells, and urinary tract and bladder epithelial cells.

When effecting delivery to an engulfing-competent mammalian cell without the use of a targeting ligand, the nature of the application contemplated will influence the choice of bacterial source for the killed bacterial cells employed. For example, *Salmonella, Escherichia* and *Shigella* species carry adhesins that are recognized by endocytosis-mediating receptors on enterocytes in the gastrointestinal tract, and may be suitable to deliver a drug that is effective for colon cancer cells. Similarly, killed bacterial cells derived from *Helicobacter pylori*, carrying adhesins specific for stomach epithelial cells, could be suited for delivery aimed at stomach cancer cells. Inhalation or insufflation may be ideal for administering intact killed bacterial cells derived from a *Pseudomonas* species that carry adhesins recognized by receptors on lung epithelial cells. Killed bacterial cells derived from *Lactobacilli* bacteria, which carry adhesins specific for urinary tract and bladder epithelial cells, could be well-suited for intraurethral delivery of a drug to a urinary tract or a bladder cancer.

In one embodiment, the delivery method is a therapeutic nucleic acid delivery method that comprises bringing killed bacterial cells that contain a plasmid comprised of a nucleic acid sequence into contact with mammalian cells that are phagocytosis- or endocytosis-competent, such that the killed bacterial cells are engulfed by the mammalian cells. The plasmid preferably encodes a therapeutic expression product. After the killed bacterial cells are brought into contact with the mammalian cells, the latter cells produce an expression product of the therapeutic nucleic acid sequence. The therapeutic nucleic acid delivery method may be performed in vitro or in vivo.

In another embodiment, the delivery method is a drug delivery method that comprises bringing killed bacterial cells that contain a drug into contact with mammalian cells that are phagocytosis- or endocytosis-competent, such that the killed bacterial cells are engulfed by the mammalian cells. The drug is then released into the cytoplasm of the mammalian cells. Alternatively, the killed bacterial cells may contain a plasmid that encodes a drug, in which case the plasmid optionally comprises a regulatory element and/or a reporter element. The drug delivery method may be performed in vitro or in vivo.

In another embodiment, the delivery method is a functional nucleic acid delivery method that comprises bringing a killed bacterial cell that contains either a functional nucleic acid molecule or a plasmid that encodes a functional nucleic acid molecule into contact with mammalian cells that are phagocytosis- or endocytosis-competent, such that the killed bacterial cells are engulfed by the mammalian cells. The functional nucleic acid or plasmid is then released into the mammalian cell. In the case that the killed bacterial cell contains a plasmid encoding a functional nucleic acid molecule, the plasmid optionally comprises a regulatory element and/or a reporter element and the mammalian cell preferably expresses the functional nucleic acid. The functional nucleic acid delivery method may be performed in vitro or in vivo.

Thus, in one aspect a method of delivering functional nucleic acid involves the use of killed bacterial cells that comprise plasmid-free functional nucleic acid. In this regard, functional nucleic acids are packaged directly into killed bacterial cells by passing through the bacterial cell's intact membrane without using plasmid-based expression constructs or the expression machinery of a host cell. In one embodiment, therefore, a method of delivering functional nucleic acid comprises (a) providing a plurality of intact killed bacterial cells in a pharmaceutically acceptable carrier, each bacterial cell of the plurality encompassing plasmid-free functional nucleic acid, and (b) bringing the killed bacterial cells of the plurality into contact with mammalian cells such that the mammalian cells engulf killed bacterial cells of the plurality, whereby the functional nucleic acid is released into the cytoplasm of the target cells.

The qualifier "plasmid-free" connotes the absence of a construct, such as a plasmid or viral vector, for in situ expression of a regulatory RNA.

Directing Killed Bacterial Cells to Specific Mammalian Cells

In another aspect, the invention provides for targeted delivery mediated that employs a bispecific ligand. The ligand brings a killed bacterial cell into contact with a target mammalian cell, such that the mammalian cell engulfs the killed bacterial cell, including the killed bacterial cell's payload.

In one embodiment, the targeted delivery method is a therapeutic nucleic acid delivery method that comprises bringing bispecific ligands into contact with killed bacterial cells that contain a therapeutic nucleic acid sequence and non-phagocytic mammalian cells. The bispecific ligands cause the killed bacterial cells to bind to the mammalian cells, and the killed bacterial cells become engulfed by the mammalian cells. The mammalian cells may then produce an expression product of the therapeutic nucleic acid.

The efficiency of nucleic acid delivery relates to the copy number of plasmid DNA that the killed bacterial cells carry. It is well known that a bottleneck of nucleic acid delivery is that >99% of the internalized DNA is degraded in the endosome or lysosome, without reaching the cytoplasm of the target cell. As a non-living particle, killed bacterial cells are expected to lack functions destabilizing or disrupting the endo-lysosomal membrane of target cells and are unlikely to possess sophisticated mechanisms for allowing internalized DNA to escape the endo-lysosomal membrane. Pursuant to the present invention, therefore, killed bacterial cells carrying at least 70 to 100 copies of plasmid DNA are preferred. The inventors have used such killed bacterial cells for successful nucleic acid delivery. The successful result suggests that even if most of the plasmid DNA is degraded in the endo-lysosomal vacuole, it is possible to overwhelm the system and to have some DNA to escape intact into the mammalian cell cytoplasm.

In another embodiment, the targeted delivery method is a drug delivery method that comprises bringing bispecific ligands into contact with killed bacterial cells that contain a drug molecule and non-phagocytic mammalian cells. The bispecific ligands cause the killed bacterial cells to bind to the mammalian cells, and the killed bacterial cells become engulfed by the mammalian cells. The drug molecule then is released into the cytoplasm of the mammalian cells.

The inventors have discovered that a significant concentration of the drug carried by bispecific ligand-targeted killed bacterial cells also escapes the endo-lysosomal membrane and enters the mammalian cell cytoplasm. Moreover, the killed bacterial cells are highly versatile in their capacity to package a range of different drugs, e.g., hydrophilic, hydrophobic, and amphipathic, such as doxorubicin, paclitaxel, cisplatin, carboplatin, 5-fluorouracil, irinotecan. All these drugs are readily packaged in killed bacterial cells in therapeutically significant concentrations.

In another embodiment, the targeted delivery method is a functional nucleic acid delivery method that comprises bringing bispecific ligands into contact with (a) killed bacterial cells that contain a functional nucleic acid molecule or a plasmid comprised of a segment that encodes a functional nucleic acid molecule and (b) target mammalian cells. The bispecific ligands cause the killed bacterial cells to bind to the mammalian cells, and the killed bacterial cells become engulfed by the mammalian cells. Following engulfment of the killed bacterial cell, the functional nucleic acid molecule is released into the cytoplasm of the target cell or expressed by the target cell.

These targeted delivery methods may be performed in vivo or in vitro, or both in vivo and in vitro. Contact between bispecific ligand, killed bacterial cell and mammalian cell may occur in a number of different ways. For in vive delivery, it is preferable to administer a killed bacterial cell that already has the bispecific ligand attached to it. Thus, killed bacterial cell, bispecific ligand and target cell all are brought into contact when the bispecific ligand-targeted killed bacterial cell reaches the target cell in vivo. Alternatively, bispecific ligand and killed bacterial cell can be separately administered in vivo.

Contact between the bispecific ligands, killed bacterial cells and mammalian cells also may occur during one or more incubations in vitro. In one embodiment, the three elements are incubated together all at once. Alternatively, step-wise incubations may be performed. In one example of a step-wise approach, killed bacterial cells and bi-specific ligands are first incubated together to form bispecific ligand-targeted killed bacterial cells, which are then incubated with target cells. In another example, bispecific ligands are first incubated with target cells, followed by an incubation with killed bacterial cells. A combination of one or more in vitro incubations and in vivo administrations also may bring bispecific ligands, killed bacterial cells and mammalian target cells into contact.

The inventors found that the targeted delivery approach is broadly applicable to a range of mammalian cells, including cells that normally are refractory to specific adhesion and endocytosis of killed bacterial cells. For example, bispecific antibody ligands with anti-O-polysaccharide specificity on one arm and anti-HER2 receptor, anti-EOF receptor or anti-androgen receptor specificity on the other arm efficiently bind killed bacterial cells to the respective receptors on a range of target non-phagocytic cells. These cells include lung, ovarian, brain, breast, prostate and skin cancer cells. Moreover, the efficient binding precedes rapid endocytosis of the killed bacterial cells by each of the non-phagocytic cells.

Target cells of the invention include any cell into which a therapeutic nucleic acid, drug or functional nucleic acid is to be introduced. Desirable target cells are characterized by expression of a cell surface receptor that, upon binding of a ligand, facilitates endocytosis. Preferred target cells are non-phagocytic, meaning that the cells are not professional phagocytes, such as macrophages, dendritic cells and Natural Killer (NK) cells. Preferred target cells also are mammalian.

Delivery methods of the invention may be employed for the purpose of treating disease conditions. The terms "treatment," "treating," "treat," and the like refer to obtaining a desired pharmacological and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

Use of Functional Nucleic Acids to Overcome Drum Resistance and Treat Disease

In another aspect, the invention provides a method of overcoming drug resistance and treating a disease, such as cancer or AIDS, in a subject through the use of functional nucleic acids. The method comprises (a) providing an intact killed bacterial cell that contains a functional nucleic acid molecule or a plasmid comprising a segment that encodes a functional nucleic acid molecule, where the functional nucleic acid molecule targets the gene or transcript of a protein that promotes drug resistance, (b) bringing the killed bacterial cell into contact with a target mammalian cell, such that the mammalian cell engulfs the killed bacterial cell, and (c) delivering a drug to the target mammalian cell. Preferably, step (c) is performed after steps (a) and (b), to allow the functional nucleic acid to diminish resistance to the drug prior to the drug's administration. Delivery of the drug and introduction of the functional nucleic acid can occur consecutively, in any order, or simultaneously.

Drugs may be delivered by any conventional means. For example, drugs may be delivered orally, parenterally (including subcutaneously, intravenously, intramuscularly, intraperitoneally, and by infusion), topically, transdermally or by inhalation. The appropriate mode of delivery and dosage of each drug is easily ascertainable by those skilled in the medical arts.

Although drug delivery may occur via conventional means, delivery via killed bacterial cells is preferred. In this regard, the inventors have discovered that the same mammalian cells can be successfully re-transfected by targeted intact killed bacterial cells that are packaged with different payloads. For example, siRNA-encoding plasmid-packaged killed bacterial cells can transfect a mammalian cell, after which drug-packaged killed bacterial cells can deliver drug to the same mammalian cell. This discovery was a surprise, and indicates that the intracellular processes associated with killed bacterial cell breakdown, endosomal release of a payload and escape of the payload to intracellular targets remains fully functional after the first round of transfection and payload delivery.

The drug may be packaged in a separate killed bacterial cell from the functional nucleic acid or plasmid encoding the functional nucleic acid. Alternatively, the drug may be packaged in the same killed bacterial cell as the functional nucleic acid molecule or plasmid encoding the functional nucleic acid molecule. Certain drugs may interact with nucleic acids and preclude co-packaging of drug and nucleic acid in the same killed bacterial cell. For example, Doxorubicin is known to interact with DNA.

Packaging Functional Nucleic Acid into Killed Bacterial Cells

Functional nucleic acid can be packaged directly into intact killed bacterial cells. The process bypasses the previously required steps of, for example, cloning nucleic acids encoding regulatory RNA into expression plasmids, transforming minicell-producing parent bacteria with the plasmids and generating recombinant minicells. Instead, plasmid-free functional nucleic acid can be packaged directly into killed bacterial cells by co-incubating a plurality of intact killed bacterial cells with functional nucleic acid in a buffer.

In some embodiments, the co-incubation may involve gentle shaking, while in others the co-incubation is static. A co-incubation of about one hour is sufficient, but shorter periods, such as about half an hour, also may be effective. In one embodiment, the buffer comprises buffered saline, for example a 1X phosphate buffer solution. The buffered saline can be in gelatin form. In another embodiment, the co-incubation is conducted at a temperature of about 4° C. to about 37° C.; about 20° C. to about 30° C.; about 25° C.; or about 37° C. In other aspects, the co-incubation can comprise about $10^7$, $10^8$, $10^9$, $10^{10}$, $10^{11}$, $10^{12}$ or $10^{13}$ killed bacterial cells. Specific parameters of temperature, time, buffer, minicell concentration, etc. can be optimized for a particular combination of conditions.

Loading Killed Bacteria with Drugs

Preferably, killed bacterial cells of the invention contain a sufficient quantity of drug to exert the drug's physiological or pharmacological effect on a target cell. Also preferably, drugs contained within the killed bacterial cells are heterologous, or foreign, to the killed bacterial cells, meaning that the killed bacterial cells' parent bacterial cells do not normally produce the drug.

Both hydrophilic and hydrophobic drugs can be packaged in killed bacterial cells by creating a concentration gradient of the drug between an extracellular medium containing killed bacterial cells and the killed bacterial cell cytoplasm. When the extracellular medium contains a higher drug concentration than the killed bacterial cell cytoplasm, the drug naturally moves down this concentration gradient, into the killed bacterial cell cytoplasm. When the concentration gradient is reversed, however, the drug does not move out of the killed bacterial cells.

To load killed bacterial cells with drugs that normally are not water soluble, the drugs initially can be dissolved in an appropriate solvent. For example, Paclitaxel can be dissolved in a 1:1 blend of ethanol and cremophore EL (polyethoxylated castor oil), followed by a dilution in PBS to achieve a solution of Paclitaxel that is partly diluted in aqueous media and carries minimal amounts of the organic solvent to ensure that the drug remains in solution. Killed bacterial cells can be incubated in this final medium for drug loading. Thus, the inventors discovered that even hydrophobic drugs can diffuse into the cytoplasm of killed bacterial cells to achieve a high and therapeutically significant cytoplasmic drug load. This is unexpected because the killed bacterial cell membrane is composed of a hydrophobic phospholipid bilayer, which would be expected to prevent diffusion of hydrophobic molecules into the cytoplasm.

Another method of loading killed bacterial cells with a drug involves culturing a recombinant parent bacterial cell under conditions wherein the parent bacterial cell transcribes and translates a nucleic acid encoding the drug, such that the drug is released into the cytoplasm of the parent bacterial cell. For example, a gene cluster encoding the cellular biosynthetic pathway for a desired drug can be cloned and transferred into a parent bacterial strain that is capable of producing killed bacterial cells. Genetic transcription and translation of the gene cluster results in biosynthesis of the drug within the cytoplasm of the parent bacterial cells, filling the bacterial cytoplasm with the drug. When the parent bacterial cell divides and forms progeny killed bacterial cells, the killed bacterial cells also contain the drug in their cytoplasm. The pre-packaged killed bacterial cells can be purified by any of the killed bacterial cell purification processes known in the art and described above.

Similarly, another method of loading killed bacterial cells with a drug involves culturing a recombinant killed bacterial cell that contains an expression plasmid encoding the drug under conditions such that the gene encoding the drug is transcribed and translated within the killed bacterial cell.

Purity of Compositions

Killed bacterial cells of the invention are substantially free from contaminating parent bacterial cells, i.e., live bacterial cells. Thus, killed bacterial cell-containing compositions of the invention preferably contain fewer than about 1 contaminating parent bacterial cell per $10^7$ killed bacterial cells, more preferably contain fewer than about 1 contaminating parent bacterial cell per $10^8$ killed bacterial cells, even more preferably contain fewer than about 1 contaminating parent bacterial cell per $10^9$ killed bacterial cells, still more preferably contain fewer than about 1 contaminating parent bacterial cell per $10^{10}$ killed bacterial cells and most preferably contain fewer than about 1 contaminating parent bacterial cell per $10^{11}$ killed bacterial cells.

A composition consisting essentially of killed bacterial cells and, optionally therapeutic nucleic acids, drugs, functional nucleic acids and bispecific ligands, of the present invention (that is, a formulation that includes such killed bacterial cells with other constituents that do not interfere unduly with the delivering quality of the composition) can be formulated in conventional manner, using one or more pharmaceutically acceptable carriers or excipients.

Bacterial cells in culture can be killed using a number of different procedures including (a) treatment with an antibiotic to which the bacterial strain is sensitive, (b) treatment with heat that is below the level at which protein coagulation occurs, and (c) treatment with solvents like ethanol at a concentration that does not result in loss of bacterial cell integrity and closure of protein channels in the bacterial membrane. The bacterial cell killing process is well known in the art of manufacture of killed bacterial vaccines. Preferably, the process of bacterial cell killing does not involve extensive denaturation of the spatial configuration of the molecules; that is, the process preferably preserves the three-dimensional structure of macromolecules from the bacteria cells, such as proteins, polysaccharides and lipids. Other processes that may be used for obtaining the killed bacterial preparation as defined above are known to those of ordinary skill in the art.

The absence of membrane denaturation in a killed bacterial preparation can be verified by any method well-known in the art. For example, plasmid DNA can be extracted from recombinant killed bacterial cells and can be sequenced to ascertain integrity of the recombinant DNA. Plasmid content can be determined by Real-time PCR and compared to plasmid content in the same number of live recombinant bacterial cells. If membrane integrity was not preserved in the killing process, then plasmid loss would be expected to occur. Additionally, if a killing process damaged recombinant plasmid, then DNA sequence aberrations would be observed. A test can also be conducted where the same number of live and killed bacterial cells are checked for the ability to package a chemotherapeutic drug.

Impurities such as media, buffers, cellular debris, membrane blebs, free nucleic acids and free endotoxin can be eliminated from a killed bacterial preparation by filtration, such as filtration through 0.2 μm cross-flow filtration. A filter pore size of about 0.2 μm is preferred because contaminants generally are smaller than 0.2 μm. Thus, using such a filter pore size allows contaminants to be filtered out, and intact killed bacterial to be retained. The filtration may be dead-end filtration or cross-flow filtration. Cross-flow filtration has the advantage of less filter clogging. Also, it is preferable to perform buffer exchange washing steps, which also can employ a filter pore size of about 0.2 pun.

Administration Routes and Form of Compositions

Compositions of the invention can be administered via various routes and to various sites in a mammalian body, to achieve the therapeutic effect(s) desired, either locally or systemically. Delivery may be accomplished, for example, by oral administration, by application of the formulation to a body cavity, by inhalation or insufflation, or by parenteral, intramuscular, intravenous, intraportal, intrahepatic, peritoneal, subcutaneous, intratumoral, or intradermal administration. The mode and site of administration is dependent on the location of the target cells. For example, cystic-fibrotic cells may be efficiently targeted by inhaled delivery of the targeted killed bacterial cells. Similarly, tumor metastasis may be more efficiently treated via intravenous delivery of targeted killed bacterial cells. Primary ovarian cancer may be treated via intraperitoneal delivery of targeted killed bacterial cells.

Compositions may be presented in unit dosage form, e.g., in ampules or vials, or in multi-dose containers, with or without an added preservative. The composition can be a solution, a suspension, or an emulsion in oily or aqueous vehicles, and may contain formulatory agents, such as suspending, stabilizing and/or dispersing agents. A suitable solution is isotonic with the blood of the recipient and is illustrated by saline, Ringer's solution, and dextrose solution. Alternatively, compositions may be in lyophilized powder form, for reconstitution with a suitable vehicle, e.g., sterile, pyrogen-free water or physiological saline. The compositions also may be in the form of a depot preparation. Such long-acting compositions may be administered by implantation (for example, subcutaneously or intramuscularly) or by intramuscular injection.

With respect to the administration of compositions of the invention, the terms "Individual," "subject," "host," and "patient," used interchangeably herein, refer to any mammalian subject for whom diagnosis, treatment, or therapy is desired. In one preferred embodiment, the individual, subject, host, or patient is a human. Other subjects may include, but are not limited to, cattle, horses, dogs, cats, guinea pigs, rabbits, rats, primates, and mice.

Administration Schedules

In general, the compositions disclosed herein may be used at appropriate dosages defined by routine testing, to obtain optimal physiological effect, while minimizing any potential toxicity. The dosage regimen may be selected in accordance with a variety of factors including age, weight, sex, medical condition of the patient; the severity of the condition to be treated, the route of administration, and the renal and hepatic function of the patient.

Optimal precision in achieving concentrations of killed bacterial cell and therapeutic within the range that yields maximum efficacy with minimal side effects may require a regimen based on the kinetics of the killed bacterial cell and therapeutic availability to target sites and target cells. Distribution, equilibrium, and elimination of a killed bacterial cell or therapeutic may be considered when determining the optimal concentration for a treatment regimen. The dosages of the killed bacterial cells and therapeutics may be adjusted when used in combination, to achieve desired effects.

Moreover, the dosage administration of the compositions may be optimized using a pharmacokinetic/pharmacodynamic modeling system. For example, one or more dosage regimens may be chosen and a pharmacokinetic/pharmacodynamic model may be used to determine the pharmacokinetic/pharmacodynamic profile of one or more dosage regimens. Next, one of the dosage regimens for administration may be selected which achieves the desired pharmacokinetic/pharmacodynamic response based on the particular pharmacokinetic/pharmacodynamic profile. See, e.g., WO 00/67776.

Specifically, the compositions may be administered at least once a week over the course of several weeks. In one embodiment, the compositions are administered at least once a week over several weeks to several months.

More specifically, the compositions may be administered at least once a day for about 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 days. Alternatively, the compositions may be administered about once every day, about once every 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 days or more.

The compositions may alternatively be administered about once every week, about once every 2, 3, 4, 5, 6, 7, 8, 9, 10, 11, 12, 13, 14, 15, 16, 17, 18, 19 or 20 weeks or more. Alternatively, the compositions may be administered at least once a week for about 2, 3, 4, 5, 6, 7, 8, 9, 10, 11, 12, 13, 14, 15, 16, 17, 18, 19 or 20 weeks or more.

Alternatively, the compositions may be administered about once every month, about once every 2, 3, 4, 5, 6, 7, 8, 9, 10, 11 or 12 months or more.

The compositions may be administered in a single daily dose, or the total daily dosage may be administered in divided doses of two, three, or four times daily.

In method in which killed bacterial cells are administered before a drug, administration of the drug may occur anytime from several minutes to several hours after administration of the killed bacterial cells. The drug may alternatively be administered anytime from several hours to several days, possibly several weeks up to several months after the killed bacterial cells.

More specifically, the killed bacterial cells may be administered at least about 1, 2, 3, 4, 5, 6, 7, 8, 9, 10, 11, 12, 13, 14, 15, 16, 17, 18, 19, 20, 21, 22, 23 or 24 hours before the drug. Moreover, the killed bacterial cells may be administered at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 days before the administration of the drug. In yet another embodiment, the killed bacterial cells may be administered at least about 1, 2, 3, 4, 5, 6, 7, 8, 9, 10, 11, 12, 13, 14, 15, 16, 17, 18, 19 or 20 weeks or more before the drug. In a further embodiment, the killed bacterial cells may be administered at least about 1, 2, 3, 4, 5, 6, 7, 8, 9, 10, 11 or 12 months before the drug.

In another embodiment, the killed bacterial cell is administered after the drug. The administration of the killed bacterial cell may occur anytime from several minutes to several hours after the administration of the drug. The killed bacterial cell may alternatively be administered anytime from several hours to several days, possibly several weeks up to several months after the drug.

EXAMPLES

Example 1. Killed Bacteria are Successfully Packaged with the Chemotherapeutic Drug Doxorubicin

*Salmonella typhimurium* strain was cultured overnight in Trypticase Soy Broth (TSB). The strain was then subcultured (1:100) in 100 ml of TSB and grown to early log phase ($OD_{600}$=0.406). Bacterial count was enumerated by plating serial dilutions on TSB agar plates and performing a colony count after overnight incubation. The result showed that the culture carried ~$5\times10^8$ bacteria/ml. To kill the bacterial cells, 10 ml of the culture was incubated for 4 hrs with 500 µg/ml gentamicin and 500 µg/ml chloramphenicol. A 100 µl sample was plated on TSB agar plate to ascertain that the bacterial cells had been killed.

Killed bacterial cells ($1\times10^9$) were incubated with 60 µg/ml doxorubicin for 2 hrs at 37° C. in 1 ml 1×BSG (buffered saline gelatin). Excess drug was washed away from the bacterial cells by six repeat washing steps where the cells were centrifuged at 13,200 rpm for five minutes followed by resuspension in fresh BSG solution.

The doxorubicin was extracted from the killed bacteria following five cycles of vortexing and sonication in the presence of 97 mM HCl-isopropyl alcohol (HCl-IPA). The samples were then diluted in an equal volume of water and the five cycles repeated. After centrifugation at 13,200 rpm for 5 min to pellet debris, the supernatants were harvested for drug quantitation by HPLC. The mobile phase comprised 100 mM ammonium formate+0.05% triethylamine (pH, 3.5): MQ:MeCN (acetonitrile) at a ratio of 28:42:30. The stationary phase comprised a Lichrosphere RP18 column (MERCK) at 40° C. Detection was by excitation at 480 nm and emission at 550 nm, using a Shimadzu 10AVP system comprising an autosampler, solvent degasser, quaternary pump, column heater (40° C.) and fluorescence detector, running version 7.2 SPI rev B software (Shimadzu Corporation).

The area under the peak was interpolated in a standard curve for doxorubicin and the results showed that ~2 µg of doxorubicin was packaged in $1\times10^9$ killed bacterial cells.

Example 2. Tumor Regression/Stabilization Following i.v. Administration of EGFR-Targeted, Doxorubicin-Packaged Killed Bacterial Cells in Nude Mice Carrying Human Breast Cancer Xenografts This example demonstrates that bispecific ligand-targeted and Doxorubicin-packaged intact killed bacterial cells can effect regression of human breast cancer cell tumor xenografts established in 6 week old female athymic nude mice.

As described in Example 1, killed *S. typhimurium* cells were packaged with chemotherapeutic drug Doxorubicin and were purified of free endotoxin by repeat centrifugation and washing away of the supernatant.

A bispecific antibody carrying anti-LPS and anti-human EGFR specificities was constructed as follows. An anti-EGFR monoclonal antibody was selected because the xeno-grafted cells were human breast cancer cells MDA-MB-468 that are known to overexpress the EGF receptor on the cell surface. A BsAb with anti-*S. typhimurium* O-antigen and anti-EGFR specificities was constructed as described in PCT/US2004/041010. Briefly, bispecific antibody (BsAb) was constructed by linking an anti-*S. typhimurium* O-antigen monoclonal antibody (MAb) (IgG1; Biodesign) and a MAb directed against a target cell-surface receptor that is mouse anti-human EGFR (IgG2a; Oncogene). The two antibodies were cross-linked via their Fc regions using purified recombinant protein A/G (Pierce Biotechnology). Briefly, protein A/G (100 µg/ml final concentration) was added to 0.5 mil of a premixed solution containing 20 µg/ml each of anti-*S. typhimurium* O-antigen and anti-human EGFR MAbs, and incubated overnight at 4° C. Excess antibodies were removed by incubation with protein G-conjugated magnetic beads and gentle mixing at room temperature for 40 min. After magnetic separation of the beads, the protein A/G-BsAb complex was incubated with 109 dox-packaged killed bacterial cells for 1 hr at room temperature to coat them with antibody via binding of the O-antigen specific Fab arm to surface LPS.

The mice used in this example were purchased from Animal Resources Centre, Perth, Wash., Australia, and all animal experiments were performed in compliance with the guide of care and use of laboratory animals, and with Animal Ethics Committee approval. The experiments were performed in the NSW Agriculture accredited small animal facility at EnGeneIC Pty Ltd (Sydney, NSW, Australia). Human breast adenocarcinoma cells (MDA-MB-468, ATCC; human mammary epithelial cells; non-phagocytic) were grown in tissue culture to full confluency in T-75 flasks in RPMI 1640 medium supplemented with 5% Bovine Calf Serum (GIBCO-BRL Life Technologies, Invitrogen Corporation, Carlsbad, Calif., USA) and glutamine (Invitrogen) in a humidified atmosphere of 95% air and 5% $CO_2$ at 37° C. $1\times10^6$ cells in 50 uL serum-free media together with 50 uL growth factor reduced matrigel (BD Biosciences, Franklin Lakes, N.J., USA) were injected subcutaneously between the shoulder blades of each mouse using a 23-gauge needle. The tumors were measured twice a week using an electronic digital caliper (Mitutoyo, Japan, precision to 0.001) and mean tumor volume was calculated using the formula, length (mm)×width$^2$(mm)×0.5=volume (mm$^3$). 16 days post-implantation, the tumors reached volumes between 40 mm$^3$ and 70 mm$^3$, and mice were randomized to four different groups of five per group.

The experiment was designed as follows. Group 1 (control) received an i.v. dose of 100 µl of sterile physiological saline. Group 2 (control) received an i.v. dose of free Doxorubicin (7 mg/kg of mouse body weight). Group 3 (control) received $1\times10^8$/dose of dox-packaged killed bacteria (killed *S. typhimurium$_{Dox}$*). Group 4 (experimental) received $1\times10^8$/dose of EGFR-targeted, dox-packaged killed bacteria ($^{EGFR}$killed *S. typhimurium$_{Dox}$*). All doses were administered via the i.v. route and the doses were given on days 21, 28 and 34.

The results showed (FIG. 1) that the $^{EGFR}$killed *S. typhimurium$_{Dox}$* were highly effective in achieving tumor regression/stabilization as compared to the three controls.

Example 3. Anti-Tumor Effects Following i.v. Administration of EGFR-Targeted, Paclitaxel-Packaged or siRNA-Kinesin Spindle Protein-Packaged Killed Bacterial Cells in Nude Mice Carrying Human Colon Cancer Xenografts This example considers whether intact killed bacterial cells packaged with paclitaxel or siRNA can inhibit the growth human colon cancer cell tumor in vivo.

Using the methods described in Example 1, killed *S. typhimurium* cells were packaged with chemotherapeutic drug paclitaxel and were purified of free endotoxin by repeat centrifugation and washing away of the supernatant. Separately, siRNA against the kinesin spindle protein (KSP) was packaged in the killed *S. typhimurium* strain. KSP, also termed kinesin-5 or Eg5, is a microtubule motor protein that is essential for the formation of bipolar spindles and the proper segregation of sister chromatids during mitosis (Enos and Morris, 1990; Blangy et al., 1995; Dagenbach and Endow, 2004). Inhibition of KSP causes the formation of monopolar mitotic spindles, activates the spindle assembly checkpoint, and arrests cells at mitosis, which leads to subsequent cell death (Blangy et al., 1995, Mayer et al., 1999; Kapoor et al., 2000; Tao et al., 2005). The KSP-siRNA double stranded oligonucleotides sequences (sense strand; 5'-AAC TOG ATC GTA AGA AGG CAG-3') were synthesized and packaged into the killed *S. typhimurium* strain by incubating $1\times10^{10}$ bacteria with 1 µm of the siRNA-KSP.

The co-incubation was carried out in 1×Phosphate Buffer Solution (PBS) (Gibco) for 12 hours at 37° C. with gentle mixing. Post-packaging, the bacteria were pelleted and washed twice with 1×PBS by centrifugation for 10 minutes at 16,200×g. The bacterial cells were washed twice in 1×PBS to eliminate excess non-packaged siRNA-KSP.

A bispecific antibody carrying anti-LPS and anti-human EGFR specificities was constructed as described in Example 2.

The mice used in this example were purchased from Animal Resources Centre, Perth, Wash., Australia, and all animal experiments were performed in compliance with the guide of care and use of laboratory animals, and with Animal Ethics Committee approval. The experiments were performed in the NSW Agriculture accredited small animal facility at EnGeneIC Pty Ltd (Sydney, NSW, Australia). Human colon cancer cells (HCT116, ATCC) were grown in tissue culture to full confluency in T-75 flasks in RPMI 1640 medium supplemented with 5% Bovine Calf Serum (GIBCO-BRL Life Technologies, Invitrogen Corporation, Carlsbad, Calif., USA) and glutamine (Invitrogen) in a humidified atmosphere of 95% air and 5% $CO_2$ at 37° C. $1 \times 10^6$ cells in 50 uL serum-free media together with 50 uL growth factor reduced matrigel (BD Biosciences, Franklin Lakes, N.J., USA) were injected subcutaneously between the shoulder blades in Balb/c nu/nu mice (n=8 mice per group) using a 23-gauge needle. The tumors were measured twice a week using an electronic digital caliper (Mitutoyo, Japan, precision to 0.001), and mean tumor volume was calculated using the formula, length (mm)×width$^2$ (mm)× 0.5=volume (mm$^3$). 16 days post-implantation, the tumors reached volumes ~200 mm$^3$, and mice were randomized to four different groups of eight per group.

The experiment was designed as follows. Group 1 (control) received an i.v. dose of 100 µl of sterile physiological saline. Group 2 (control) EGFR-targeted killed $S.$ $typhimurium$ bacteria not carrying any therapeutic payload (G2; $^{EGFR}S.$ $typhimurium$). Group 3 (expt) EGFR-targeted killed $S.$ $typhimurium$ bacteria packaged with chemotherapeutic drug paclitaxel (G3; $^{EGFR}S.$ $typhimurium_{Paclitaxel}$). Group 4 (expt) EGFR-targeted killed $S.$ $typhimurium$ bacteria packaged with siRNA against kinesin spindle protein (G4; $^{EGFR}S.$ $typhimurium_{siRNA-KSP}$). The treatments were administered three times per week.

Figure 2:
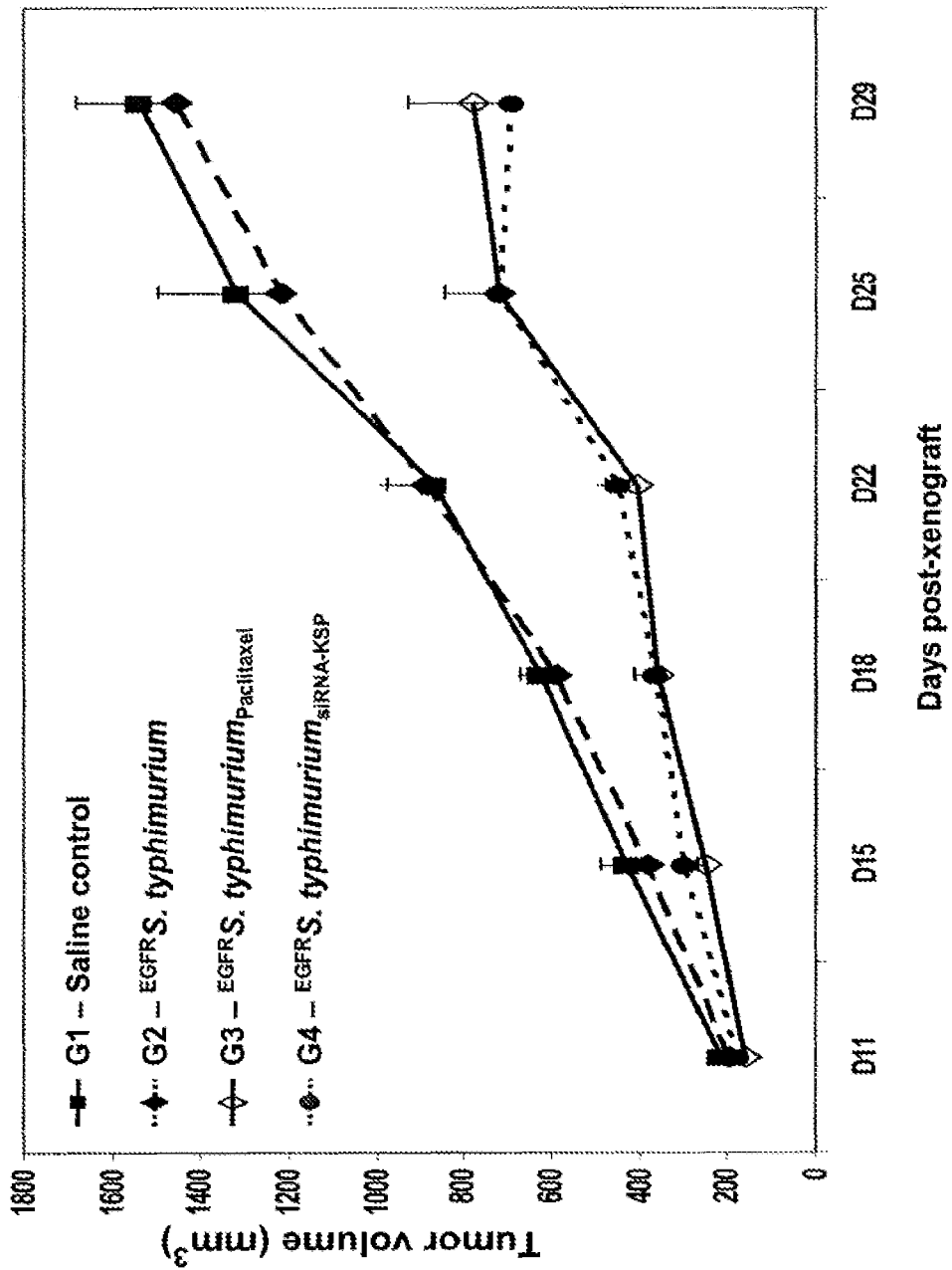
FIG. 2 graphically shows that intact killed bacterial cells packaged with paclitaxel or siRNA inhibit the growth of human colon cancer cell (HCT116) tumors in vivo.

The results show (FIG. 2) that both treatments, i.e. $^{EGFR}$killed $S.$ $typhimurium_{Paclitaxel}$ and $^{EGFR}S.$ $typhimurium_{siRNA-KSP}$, showed highly significant anti-tumor effects as compared to the two controls. Thus, the data demonstrate that intact killed bacterial cells packaged with paclitaxel or siRNA inhibit the growth of human colon cancer cell tumor in vivo.

Example 4. Use of Dual Treatment Comprising Receptor-Targeted Killed Bacteria-Mediated shRNA Followed by Receptor-Targeted Killed Bacteria-Mediated Drug Delivery To demonstrate that receptor-targeted killed bacteria can reverse drug resistance in cancer cells in-vivo, we carried out the following study in Balb/c nu/nu mice. For xenograft cells, we used the human colon cancer cell line Caco-2, which is highly resistant to first-line chemotherapy drugs for colon cancer, such as irinotecan and 5-fluorouracil (5-FU).

Using the methods described in Example 1, $S.$ $typhimurium$ killed bacteria were packaged with chemotherapeutic drug irinotecan or 5-FU. Excess irinotecan or 5-FU non-specifically attached to the outer surface of the killed bacteria was washed away by centrifugation of the bacterial cells at 13,200 rpm for 10 min, and the washed cells were resuspended in fresh 1×PBS. This washing step was repeated.

The irinotecan or 5-FU-packaged killed $S.$ $typhimurium$ cells were targeted to the EGFR via attachment of an anti-O-polysaccharide/anti-EGFR bispecific antibody to the bacterial cell surface, as described in the previous examples. An anti-EGFR monoclonal antibody was selected because the xenograft cells, Caco-2, are known to overexpress the EGFR on the cell surface (Nyati et al., 2004). The EGFR-targeted, drug-packaged killed bacteria were designated $^{EGFR}S.$ $typhimurium_{5-FU}$ and $^{EGFR}S.$ $typhimurium_{Irino}$.

A recombinant $S.$ $typhimurium$ strain carrying a plasmid encoding anti-MDR1 shRNA sequence was generated as follows. The MDR-1 shRNA sequence used in this study (5'-TCGAAAGAAACCAACTGTCAGTGTAgagtactg/TA-CACTGACAGTTGGTTTCTT TTTT-3') was described by Wu et al., 2003. The shRNA sequence was synthesized and subcloned into plasmid IMG-800 (Imgenex Corp., San Diego, Calif., USA) such that the sequence could be expressed from the plasmid U6 promoter. The plasmid carries the pUC origin of replication which enables high plasmid copy numbers in bacterial cells. The recombinant plasmid was sequenced to ensure that the shRNA sequence was correct and in-frame for expression from the U6 promoter. The recombinant plasmid was transformed into the $S.$ $typhimurium$, and the recombinant strain was designated $S.$ $typhimurium_{shRNA-MDR1}$. EGFR-targeted $S.$ $typhimurium_{shRNA-MDR1}$ was constructed by attaching the anti-O-polysaccharide/anti-EGFR bispecific antibody to the surface of the recombinant bacteria to generate $^{EGFR}S.$ $typhimurium_{shRNA-MDR1}$.

The various mice groups (five mice per group) received the following treatments: Group 1 (control) sterile saline; Group 2 (control) $^{EGFR}S.$ $typhimurium_{shRNA-MDR1}$; Group 3 (control) EGFR-targeted, 5-FU-packaged killed bacteria ($^{EGFR}S.$ $typhimurium_{5-FU}$); Group 4 (expt) $^{EGFR}S.$ $typhimurium_{shRNA-MDR1}$ followed by $^{EGFR}S.$ $typhimurium_{5-FU}$; Group 5 (control) EGFR-targeted, Irino-packaged killed bacteria ($^{EGFR}S.$ $typhimurium_{5-FU}$); Group 6 (expt) $^{EGFR}S.$ $typhimurium_{shRNA-MDR1}$ followed by $^{EGFR}S.$ $typhimurium_{Irino}$; Groups 2 to 6 received 1×109 bacterial cells, and all treatments were i.v.

Figure 3:
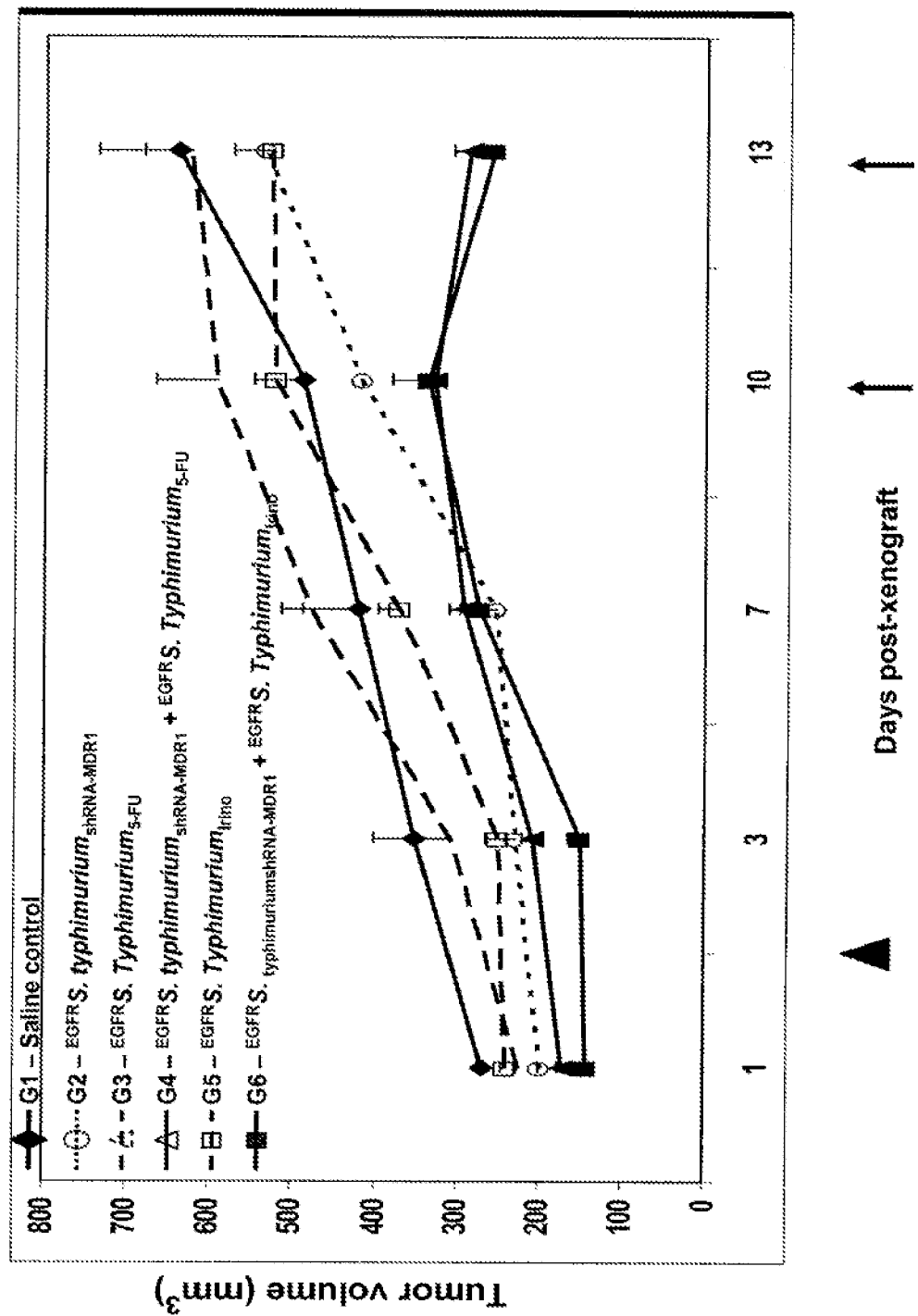
FIG. 3 shows the reversal of drug resistance in mice carrying human colon cancer (Caco-2) xenografts by using a dual treatment protocol, wherein the first treatment comprises EGFR-packaged, killed *S. typhimurium* carrying anti-MDR-1 shRNA and the second treatment comprises EGFR-packaged, killed *S. typhimurium* carrying either Irinotecan or 5-fluorouracil (5-FU). The first treatment and second treatments are shown by a triangle and an arrow, respectively, below the x-axis.

The results showed (FIG. 3) that as expected, the Caco-2 cells remained resistant following treatments with $^{EGFR}S.$ $typhimurium_{Irino}$, $^{EGFR}S.$ $typhimurium_{5-FU}$ and $^{EGFR}S.$ $typhimurium_{shRNA-MDR1}$. Cells that received dual treatment, i.e. $^{EGFR}S.$ $typhimurium_{shRNA-MDR1}$ followed by $^{EGFR}S.$ $typhimurium_{Irino}$ (G6 mice) or $^{EGFR}S.$ $typhimurium_{5-FU}$ (G4 mice), showed highly significant reversal of drug resistance and tumor regression. The data demonstrates that a dual treatment protocol, e.g. receptor-targeted killed bacteria-mediated shRNA delivery followed by receptor-targeted killed bacteria-mediated chemotherapeutic drug delivery, is highly effective in reversing drug resistance in non-phagocytic mammalian cells.

REFERENCES

All publications and patents mentioned in this specification are incorporated herein by reference. Reference to a publication or patent, however, does not constitute an admission as to prior art.

Akporiaye, E. T. & Hersh, E. Clinical aspects of intratumoral gene therapy. Curr. Opin. Mol. Ther. 1: 443-453 (1999).

Ambudkar, et al., *Annu. Rev. Pharmacol. Toxicol.* 39: 361 (1999).

Batra R K, Wang-Johanning F, Wagner E, Garver R I Jr, Curiel D T. Receptor-mediated gene delivery employing lectin-binding specificity. *Gene Ther.* 1994 July; 1(4):255-60.

Becker C M, Farnebo F A, Iordanescu I, Behonick D J, Shih M C, Dunning P, Christofferson R, Mulligan R C, Taylor G A, Kuo C J, Zetter B R. Gene therapy of prostate cancer with the soluble vascular endothelial growth factor receptor Flk1. *Cancer Biol Ther.* 2002 September-October; 1(5):548-53.

Bergey's Manual of Systematic Bioloty, 2$^{nd}$ ed., Springer-Verlag, 2001.

Blangy, A., Lane, H. A., d'Herin, P., Harper, M., Kress, M., Nigg, E. A. Phosphorylation by p34cdc2 regulates spindle association of human Eg5, a kinesin-related motor essential for bipolar spindle formation in vivo. *Cell* 83: 1159-1169 (1995).

Boucher, R. C., Pickles, R. J., Rideout, J. L., Pendergast, W. & Yerxa, B. R. Targeted gene transfer using G protein coupled receptors. U.S. patent application. US 2003/004123 A1. Jan. 2, 2003.

Bullough, P. A., Hughson, F. M., Skehel, J. J., Wiley, D. C. Structure of influenza haemagglutinin at the pH of membrane fusion. *Nature* 371: 37-43 (1994).

Caplen, *Expert Opin. Biol. Ther.*, 3(4): 575-86 (2003).

Caplen and Mousses, *Ann. N.Y. Acad. Sci.*, 1002: 56-62 (2003).

Carter, P. Improving the efficacy of antibody-based cancer therapies. *Nat Rev Cancer.* 2001 November; 1(2):118-29.

Ciliberto et al., "Cell-specific expression of a transfected human alpha 1-antitrypsin gene," *Cell.* 41: 531 (1985).

Chen, L. M., Kaniga, K., Galan, J. E. *Salmonella* spp. are cytotoxic for cultured macrophages. *Mol. Microbiol.* 21: 1101-1115 (1996).

Chen, D., Murphy, B., Sung, R., Bromberg, J. S. Adaptive and innate immune responses to gene transfer vectors: role of cytokines and chemokines in vector function. *Gene Ther,* 10: 991-998 (2003).

Clark, P. R. & Hersh, E. M. Cationic lipid-mediated gene transfer: current concepts. *Curr. Opin. Mol. Ther.* 1: 158-176 (1999).

Collins & Olive, 32 *Biochem.* 2795-99 (1993).

Curiel et al., "Long-term inhibition of clinical and laboratory human immunodeficiency virus strains in human T-cell lines containing an HIV-regulated diphtheria toxin A chain gene," *Hum. Gene Ther.* 4: 741 (1993).

Dagenbach, E. M., and Endow, S. A. A new kinesin tree. *J. Cell Sci.* 117: 3-7 (2004).

Dang, L. H., Bettegowda, C., Huso, D. L., Kinzler, K. W., Vogelstein, B. Combination bacteriolytic therapy for the treatment of experimental tumors. *Proc. Natl. Acad. Sci. USA.* 98: 15155-15160(2001).

de Haard, H. J. et al. A large non-immunized human Fab fragment phage library that permits rapid isolation and kinetic analysis of high affinity antibodies. *J. Biol. Chem.* 274, 18218-18230 (1999).

de Jong, G., Telenius, A., Vanderbyl, S., Meitz, A., Drayer, J. Efficient in-vitro transfer of a 60-Mb mammalian artificial chromosome into murine and hamster cells using cationic lipids and dendrimers. *Chromosome Res.* 9: 475-485 (2001).

Dinges et al., "HIV-regulated diphtheria toxin A chain gene confers long-term protection against HIV type 1 infection in the human promonocytic cell line U937," *Hum. Gene Ther.* 6: 1437 (1995).

Dow, S. W., Fradkin, L. G., Liggitt, D. H., Willson, A. P., Heath, T. D., Potter, T. A. Lipid-DNA complexes induce potent activation of innate immune responses and antitumor activity when administered intravenously. *J. Immunol.* 163: 1552-1561 (1999).

Dramsi, S. & Cossart, P. Intracellular pathogens and the actin cytoskeleton. *Annu. Rev. Cell. Dev. Biol.* 14: 137-166 (1998).

Duan et al., *Mol. Cancer Therapeutics,* 3(7): 833-38 (2004).

Dubel S, Breitling F, Kontermann R, Schmidt T, Skerra A, Little M. Bifunctional and multimeric complexes of streptavidin fused to single chain antibodies (scFv). *J. Immunol. Methods* (1995) 178, 201-209.

Dunham, S. P. The application of nucleic acid vaccines in veterinary medicine, *Res. Vet. Sci.* 73: 9-16 (2002).

Duxbury et al., *J. Am. Coll. Surg.*, 198: 953-59 (2004).

El Ouahabi, A., Thiry, M., Fuks, R., Ruysschaert, J. & Vandenbranden, M. The role of the endosome destabilizing activity in the gene transfer process mediated by cationic lipids. *FEBS Lett.* 414: 187-192 (1997).

Enos, A. P., and Morris, N. R. Mutation of a gene that encodes a kinesin-like protein blocks nuclear division in *A. nidulans*. *Cell* 60: 1019-1027 (1990).

Essani, K. & Dales, S. Biogenesis of vaccinia: evidence for more than 100 polypeptides in the virion. *Virology* 95: 385-394 (1979).

Farhood, H., Serbina, N. & Huang, L. The role of dioleoyl phosphatidylethanolamine in cationic liposome mediated gene transfer. *Biochim. Biophys. Acta* 1235; 289-295 (1995).

Fasbender, A., Marshall, J., Moninger, T. O., Grunst, T., Cheng, S. & Welsh, M. J. Effect of co-lipids in enhancing cationic lipid-mediated gene transfer in vitro and in vivo. *Gene. Ther.* 4: 716-725 (1997).

Feigner, P. L., Ringold, G. M. Cationic liposome-mediated transfection. *Nature* 337: 387-388 (1989).

Ferrari, S., Griesenbach, U., Geddes, D. M., Alton, E. Immunological hurdles to lung gene therapy. *Clin Exp Immunol,* 132: 1-8 (2003).

Finlay, B. B. & Cossart, P. Exploitation of mammalian host cell functions by bacterial pathogens. *Science* 276: 718-25 (1997).

Fox, M. E., Lemmon, M. J., Mauchline, M. L, et al. Anaerobic bacteria as a delivery system for cancer gene therapy: in vitro activation of 5-fluorocytosine by genetically engineered clostridia. *Gene Therapy.* 3: 173-178 (1996).

Frain et al., "Binding of a liver-specific factor to the human albumin gene promoter and enhancer," *Mol. Cell Biol.* 10: 991 (1990).

Galan, J. E. Molecular and cellular bases of *Salmonella* entry into host cells. *Curr. Top. Microbiol. Immunol.* 209: 43-60 (1996).

Gao, H., Shi, W. & Freund, L. B. Mechanics of receptor-mediated endocytosis. *Proc. Natl. Acad. Sci. U.S.A.* 102: 9469-9474 (2005).

Gerlowski, L. & Jain, R. Microvascular permeability of normal and neoplastic tissues. *Microvasc. Res.* 31: 288-305 (1986).

Glennie M J, McBride H M, Worth A T, Stevenson G T. Preparation and performance of bispecific F(ab' gamma)2 antibody containing thioether-linked Fab' gamma fragments. *J Immunol.* 1987 Oct. 1; 139(7):2367-75.

Gosselin M A, Lee R J. Folate receptor-targeted liposomes as vectors for therapeutic agents. *Biotechnol Annu Rev.* 2002; 8:103-31

Greber, U. F., Webster, P., Weber, J. & Helenius, A. The role of the adenovirus protease on virus entry into cells, *EMBO J.* 15: 1766-1777 (1996).

Green, N. K. & Seymour, L. W. Adenoviral vectors: systemic delivery and tumor targeting. *Cancer Gene Ther.* 9: 1036-1042 (2002).

Griffiths, A. D. et al. Isolation of high affinity human antibodies directly from large synthetic repertoires. *EMBO J.* 13, 3245-3260 (1994).

Guerrier-Takada et al., *Cell,* 35: 849 (1983).

Hafez, I. M., Maurer, N. & Cullis, P. R. On the mechanism whereby cationic lipids promote intracellular delivery of polynucleic acids. *Gene Ther.* 8: 1188-1196 (2001).

Hampel and Tritz, *Biochem.,* 28: 4929 (1989).

Hampel et al., *Nucleic Acids Research:* 299 (1990)

Hanahan, Heritable formation of pancreatic beta-cell tumours in transgenic mice expressing recombinant insulin/simian virus 40 oncogenes. 1985 May 9-15; 315 (6015): 115-122.

Harrison et al., "Inhibition of human immunodeficiency virus-1 production resulting from transduction with a retrovirus containing an HIV-regulated diphtheria toxin A chain gene," *Hum. Gene Ther.* 3: 461 (1992a).

Harrison et al., "Inhibition of HIV production in cells containing an integrated, HIV-regulated diphtheria toxin A chain gene," *AIDS. Res. Hum. Retroviruses* 8: 39 (1992b).

Hart, "Tissue specific promoters in targeting systematically delivered gene therapy," *Semin. Oncol.* 23: 154 (1996).

Heim et al., "Wavelength mutations and posttranslational autoxidation of green fluorescent protein," *Proc. Nat'l. Acad. Sci. USA* 91: 12501 (1994).

Hobbs, S. K., Monsky, W. L., Yuan, F., Roberts, W. G., Griffith, L., Torchilin, V. P. and Jain, R. K. Regulation of transport pathways in tumor vessels: Role of tumor type and microenvironment. *Proc. Natl. Acad. Sci. USA* 95: 4607-4612 (1998).

Hoshida T, Sunamura M, Duda D G, Egawa S, Miyazaki S, Shineha R, Hamada H, Ohtani H, Satomi S, Matsuno S. Gene therapy for pancreatic cancer using an adenovirus vector encoding soluble flt-1 vascular endothelial growth factor receptor. *Pancreas.* 2002 August; 25(2):111-21.

Hu, S, L Shively, A Raubitschck, M Sherman, L E Williams, J Y Wong, J E Shively, and A M Wu. Minibody: A novel engineered anti-carcinoembryonic antigen antibody fragment (single-chain Fv-CH3) which exhibits rapid, high-level targeting of xenografts. *Cancer Res.* 1996 56: 3055-3061.

Hudson, P. J. & Souriau, C. Recombinant antibodies for cancer diagnosis and therapy. *Expert Opin. Biol. Ther.* 1, 845-855 (2001).

Hudson P J, Souriau C. Engineered antibodies. *Nat Med.* 2003 January; 9 (1): 129-34.

Hung M C, Hortobagyi G N, Ueno N T. Development of clinical trial of E1A gene therapy targeting HER-2/neu-overexpressing breast and ovarian cancer. *Adv Exp Med Biol.* 2000; 465:171-80.

Jain, R. K. Transport of molecules across tumor vasculature. *Cancer Metastasts Rev.* 6: 559-593 (1987).

Jain, R. K. Delivery of molecular medicine to solid tumors. *Science* 271: 1079-1080 (1996).

Jain, R. K. The Eugene M. Landis Award Lecture 1996: Delivery of molecular and cellular medicine to solid tumors. *Microcirculation* 4: 1-23 (1997).

Jain, R. K. Delivery of molecular and cellular medicine to solid tumors. *J. Control. Release* 53, 49-67 (1998).

Jain, R. K. Delivery of molecular and cellular medicine to solid tumors. *Adv. Drug Deliv. Rev.* 46: 149-68 (2001).

James, M. B., Giorgio, T. D. Nuclear-associated plasmid, but not cell-associated plasmid, is correlated with transgene expression in cultured mammalian cells. *Mol. Ther.* 1: 339-346 (2000).

Jones, P. T., Dear, P. H., Foote, J., Neuberger, M. S. & Winter, G. Replacing the complementarity-determining regions in a human antibody with those from a mouse. *Nature* 321, 522-525 (1986).

Kaetzel C S, Blanch V J, Hempen P M, Phillips K M, Piskurich J F, Youngman K R The polymeric immunoglobulin receptor: structure and synthesis. *Biochem Soc Trans* 25:475-480 (1997).

Kanke, M., Sniccinski, I., & DeLuca, P. P. Interaction of microspheres with blood constituents. I. Uptake of polystyrene spheres by monocytes and granulocytes and effect on immune responsiveness of lymphocytes. *J. Parenter. Sci. Technol.* 37: 210-217 (1983).

Kapoor, T. M., Mayer, T. U., Coughlin, M. L., Mitchison, T. J. Probing spindle assembly mechanisms with monastrol, a small molecule inhibitor of the mitotic kinesin, Eg5. *J. Cell Biol.* 150: 975-988 (2000).

Karpovsky B, Titus J A, Stephany D A, Segal D M. Production of target-specific effector cells using hetero-cross-linked aggregates containing anti-target cell and anti-Fc gamma receptor antibodies. *J Exp Med.* 160:1686-701 (1984).

Katabi et al., "Hexokinase Type II: A Novel Tumor Specific Promoter for Gene-Targeted Therapy Differentially Expressed and Regulated in Human Cancer Cells," *Human Gene Therapy* 10: 155 (1999).

Kelsey et al., "Species- and tissue-specific expression of human alpha 1-antitrypsin in transgenic mice," *Genes and Devel.* 1: 161 (1987).

Kerem et al., "Identification of the cystic fibrosis gene: genetic analysis," *Science* 245: 1073 (1989).

King, I., et al. Tumor-targeted *Salmonella* expressing cytosine deaminase as an anticancer agent. *Hum. Gene Ther.* 13: 1225-1233 (2002).

Kleeff J, Fukahi K, Lopez M E, Friess H, Buchler M W, Sosnowski B A, Korc M. Targeting of suicide gene delivery in pancreatic cancer cells via FGF receptors. *Cancer Gene Ther.* 2002 June; 9(6):522-32.

Klemm, A. R. Effects of polyethylenimine on endocytosis and lysosome stability. *Biochem. Pharmacol.* 56: 41-46 (1998).

Knappik, A. et al. Fully synthetic human combinatorial antibody libraries (HuCAL) based on modular consensus frameworks and CDRs randomized with trinucleotides. *J. Mol. Biol.* 296, 57-86 (2000).

Konerding, M. A., Miodonski, A. J., Lametschwandtner, A. Microvascular corrosion casting in the study of tumor vascularity: a review. *Scanning Microsc.* 9: 1233-1243 (1995).

Kostelny S A, Cole M S, Tso J Y. Formation of a bispecific antibody by the use of leucine zippers. *J Immunol.* 1992 Mar. 1; 148(5):1547-53.

Kreiss, P., Cameron, B., Rangara, R., Mailhe, P., Aguerre-Charriol, O., Airiau, M., Scherman, D., Crouzet, J., Pitard, B. Plasmid DNA size does not affect the physicochemical properties of lipoplexes but modulates gene transfer efficiency. *Nucleic Acids Res.* 27: 3792-3798 (1999).

Kurane et al., "Targeted Gene Transfer for Adenocarcinoma Using a Combination of Tumor specific Antibody and Tissue-specific Promoter," *Jpn. J. Cancer Res.* 89: 1212 (1998).

Leder et al., "Consequences of widespread deregulation of the c-myc gene in transgenic mice: multiple neoplasms and normal development," *Cell* 45: 485 (1986).

Lee, K-D, OhY, Portnoy, D, et al. Delivery of macromolecules into cytosol using liposomes containing hemolysin from *Listeria monocytogenes*. *J. Biol. Chem.* 271: 7249-7252 (1996).

Lee, C. H., Wu, C. L., and Shiau, A. L. (2005a). Endostatin gene therapy delivered by *Salmonella choleraesuis* in murine tumor models. *J. Gene Med.* 6: 1382-1393.

Lee, C. H., Wu, C. L., and Shiau, A. L. (2005b). Systemic administration of attenuated *Salmonella choleraesuis* carrying thrombospondin-1 gene leads to tumor-specific transgene expression, delayed tumor growth and prolonged survival in the murine melanoma model. *Cancer Gene Ther.* 12: 175-184.

Lemmon, M. J., van Zijl, P., Fox, M. E., et al. Anaerobic bacteria as a gene delivery system that is controlled by the tumor microenvironment. *Gene Therapy.* 8: 791-796 (1997).

Less, J. R., Skalak, T. C., Sevick, E. M., Jain, R. K. Microvascular architecture in a mammary carcinoma: branching patterns and vessel dimensions. *Cancer Res.* 51: 265-273 (1991).

Less, J. R., Posner, M. C., Boucher, Y., Borochovitz, D., Wolmark, N., Jain, R. K. Interstitial hypertension in human breast and colorectal tumors. *Cancer Res.* 52: 6371-6374 (1992).

Less, J. R., Posner, M. C., Skalak, T. C., Wolmark, N., Jain, R. K Geometric resistance and microvascular network architecture of human colorectal carcinoma. *Microcirculation* 4: 25-33 (1997).

Li, X., Fu, G-F., Fan, Y-R., et al. *Bifidobacterium adolescentis* as a delivery system of endostatin for cancer gene therapy: selective inhibitor of angiogenesis and hypoxic tumor growth. *Cancer Gene Ther.* 10: 105-111 (2003).

Liu, Q., Muruve, D. A. Molecular basis of the inflammatory response to adenovirus vectors. *Gene Ther.* 10: 935-940 (2003).

Liu, S-C., Minton, N. P., Giaccia, A. J., Brown, J. M. Anticancer efficacy of systemically delivered anaerobic bacteria as gene therapy vectors targeting tumor hypoxia/necrosis. *Gene Ther.* 9: 291-296 (2002).

Lorenzi, G. L., Lee, K. D. Enhanced plasmid DNA delivery using anionic LPDII by listeriolysin O incorporation. *J. Gene Med.* 7: 1077-1085 (2005).

Low K B, Ittensohn M, Le T, et al. Lipid A mutant *Salmonella* with suppressed virulence and TNF☐ induction retain tumor-targeting in vivo. *Nat Biotechnol.* 1999; 17: 37-41.

Luo X, Li Z, Lin S, et al. Antitumor effect of VNP20009, an attenuated *Salmonella*, in murine tumor models. *Oncol Res.* 2001; 12:501-508.

MacDonald et al., "Expression of the pancreatic elastase 1 gene in transgenic mice," *Hepatology* 7: 425 (1987).

Maeda, H. The enhanced permeability and retention (EPR) effect in tumor vasculature: the key role of tumor-selective macromolecular drug targeting. *Adv. Enzyme Regul.* 41: 189-207 (2001).

Maeda, H. & Matsumura, Y. Tumoritropic and lymphotropic principles of macromolecular drugs. *Crit. Rev. Ther. Drug Carrier Syst.* 6, 193-210 (1989).

Marsh, M. & A. M. Helenius, A. M. Virus entry into animal cells. *Adv. Virus Res.* 36: 107-151 (1989).

Marshall. Carcinoembryonic antigen-based vaccines. *Semin. Oncol.* 2003 June; 30 (3 Suppl. 8): 30-36.

Mason et al., "The hypogonadal mouse: reproductive functions restored by gene therapy," *Science* 234: 1372 (1986).

Mayer, T. U., Kapoor, T. M., Haggarty, S. J., King, R. W., Schreiber, S. L., Mitchison, T. J. Small molecule inhibitor of mitotic spindle bipolarity identified in a phenotype-based screen. *Science* 286: 971-974 (1999).

Menard, R., Dehio, C. & Sansonetti, P. J. Bacterial entry into epithelial cells: the paradigm of *Shigella*. *Trends Microbiol.* 4: 220-226 (1996).

Meyer, K., Uyechi, L. S. & Szoka, F. C. J. Manipulating the intracellular trafficking of nucleic acids, in: K. L. Brigham (Ed.), Gene Therapy for Diseases of the Lung, Marcel Dekker Inc, New York, pp. 135-180 (1997).

Minton, N. P., Mauchline, M. L., Lemmon, M. J., et al. Chemotherapeutic tumour targeting using clostridial spores. *FEMS Microbiol. Rev.* 17: 357-364 (1995).

Monack, D. M., Raupach, B., Hromockyj, A. E., Falkow, S. *Salmonella typhimurium* invasion induces apoptosis in infected macrophages. *Proc. Natl. Acad. Sci. USA*. 93: 9833-9838 (1996).

Morton & Potter, "Rhabdomyosarcoma-specific expression of the herpes simplex virus thymidine kinase gene confers sensitivity to ganciclovir," *J. Pharmacology & Exper. Therapeutics* 286: 1066 (1998).

Mui, B., Ahkong, Q., Chow, L. & Hope, M. Membrane perturbation and the mechanism of lipid-mediated transfer of DNA into cells. *Biochim. Biophys. Acta* 1467: 281-292 (2000).

Nakai, T., Kanamori, T., Sando, S. & Aoyama, Y. Remarkably size-regulated cell invasion by artificial viruses. Saccharide-dependent self-aggregation of glycoviruses and its consequences in glycoviral gene delivery. *J. Am. Chem. Soc.* 125: 8465-8475 (2003).

Nettelbeck, D. M., Miller, D. W., Jerome, V., Zuzarte, M., Watkins, S. J., Hawkins, R. E., Muller, R. & Kontermann, R. E. Targeting of adenovirus to endothelial cells by a bispecific single-chain diabody directed against the adenovirus fiber knob domain and human endoglin (CD105). *Mol. Ther.* 3: 882-891 (2001).

Nieth et al., *FEBS Letters,* 545: 144-50 (2003).

Nuyts S, Mellaert IV, Theys J, Landuyt W, Lanbin P, Anne J. *Clostridium* spores for tumor-specific drug delivery. *Anti-Cancer Drugs.* 2002a; 13: 115-125.

Nuyts S, Van Mellaert L, Theys J, et al. Radio-responsive recA promoter significantly increases TNFa production in recombinant clostridia after 2 Gy irradiation. *Gene Therapy.* 2002b; 8:1197-1201.

Ogris, M. & Wagner, E. Targeting tumors with non-viral gene delivery systems. *Drug Discovery Today* 7: 479-485 (2002).

Osaki, F., Kanamori, T., Sando, S., Sera, T. & Aoyama, Y. A quantum dot conjugated sugar ball and its cellular uptake. On the size effects of endocytosis in the subviral region. *J. Am. Chem. Soc.* 126: 6520-6521 (2004).

Osboum, i., Jermutus, L., Duncan, A. Current methods for the generation of human antibodies for the treatment of autoimmune diseases. *Drug Delivery Tech* 8: 845-851 (2003).

Pack P, Pluckthun A. Miniantibodies: use of amphipathic helices to produce functional, flexibly linked dimeric Fv fragments with high avidity in *Escherichia coli*. *Biochemistry.* 1992 Feb. 18; 31(6): 1579-84.

Paglia P, Terrazzini N, Schulze K, Guzman C A, Colombo M P. In vive correction of genetic defects of monocyte/macrophages using attenuated *Salmonella* as oral vectors for targeted gene delivery. *Gene Ther* 2000; 7: 1725-1730.

Pawelek J M, Low K B, Bermudes D. Tumor-targeted *Salmonella* as a novel anticancer vector. *Cancer Res.* 1997; 57:4537-4544.

Pawelek J, Low K B, Bermudes D. Bacteria as tumourtargeting vectors. *Lancet Oncol Rev.* 2003; 4:548-556.

Perrotta and Been, *Biochem.*, 31: 16 (1992).

Peterson H I, Appelgren L: Tumour vessel permeability and transcapillary exchange of large molecules of different size. *Bibl Anat* 1977, 15:262-265.

Pikaar et al., *J. Infect. Dis.* 172: 481 (1995).

Pinkert et al., "An albumin enhancer located 10 kb upstream functions along with its promoter to direct efficient, liver-specific expression in transgenic mice," *Genes and Devel.* 1: 268 (1987).

Platt J, Sodi S, Kelley M, et al. Antitumour effects of genetically engineered *Salmonella* in combination with radiation. *Eur J Cancer.* 2000; 36:2397-2402.

Prasher et al., "Using GFP to see the light," *Trends in Genetics* 11: 320 (1995).

Ragheb et al., "Inhibition of human immunodeficiency virus type 1 by Tat/Rev-regulated expression of cytosine deaminase, interferon alpha2, or diphtheria toxin compared with inhibition by transdominant Rev," *Hum. Gene Ther.* 10: 103 (1999).

Readhead et al., "Myelin deficient mice: expression of myelin basic protein and generation of mice with varying levels of myelin," *Cell* 48: 703 (1987).

Ridgway J B, Presta L G, Carter P. 'Knobs-into-holes' engineering of antibody CH3 domains for heavy chain heterodimerization. *Protein Eng.* 1996 July; 9(7):617-21.

Riechmann, L., Clark, M., Waldmann, H. & Winter, G. Reshaping human antibodies for therapy. *Nature* 332, 323-327 (1988).

Riezman, *Trends in Cell Biology*, 3: 330 (1993).

Riordan et al., "Identification of the cystic fibrosis gene: cloning and characterization of complementary DNA," *Science* 245: 1066 (1989).

Rommens et al., "Identification of the cystic fibrosis gene: Chromosome walking and jumping," *Science* 245: 1059 (1989).

Rosenberg, S. A., Spiess, P. M., and Kleiner, D. E. Antitumour effects in mice of the intravenous injection of attenuated *Salmonella typhimurium. J. Immunother.* 25: 218-225 (2002).

Rossi et al., *Aids Research and Human Retroviruses*, 8: 183 (1992)

Ruiz, F. E., Clancy, J. P., Perricone, M. A., Bebok, Z., Hong, J. S., Cheng, S. H., Meeker, D. P., Young, K. R., Schoumacher, R. A., Weatherly, M. R., Wing, L., Morris, J. E., Sindel, L., Rosenberg, M., van Ginkel, F. W., McGhee, J. R., Kelly, D., Lyrene, R. K., Sorscher, E. J. A clinical inflammatory syndrome attributable to acrosolized lipid-DNA administration in cystic fibrosis. *Hum. Gene Ther.* 12: 751-761 (2001).

Salomon D S, Brandt R, Ciardiello F, Normanno N. Epidermal growth factor-related peptides and their receptors in human malignancies. *Crit Rev Oncol Hematol* 1995, 19, 183-232.

Sandvig & Deurs, *Trends in Cell Biology*, 4: 275 (1994).

Saville & Collins, *Cell,* 61: 685-96 (1990).

Saville & Collins, *PNAS (USA)*, 88: 8826-30 (1991).

Scheule, R. K. The role of CpG motifs in immunostimulation and gene therapy. *Adv. Drug Deliv. Rev.* 44: 119-134 (2000).

Seth, P., Willingham, M. C. & Pastan, I. Binding of adenovirus and its external proteins to Triton X-114. Dependence on pH. *J. Biol. Chem.* 260: 14431-14434 (1985).

Seymour, L. W. Passive tumor targeting of soluble macromolecules and drug conjugates. *Crit. Rev. Ther. Drug Carrier Syst.* 9, 135-187 (1992).

Shangara et al., "Suicide genes: past, present and future perspectives," *Immunology Today* 21: 48 (2000).

Shaw & Griffen, *Nature* 289: 409 (1981).

Sheets, M. D. et al. Efficient construction of a large nonimmune phage antibody library: the production of high-affinity human single-chain antibodies to protein antigens. *Proc. Natl Acad. Sci. USA* 95, 6157-6162 (1998).

Simoes, S., Pedro, P., Duzgunes, N. & Pedrosa de Lima, M. Cationic liposomes as gene transfer vectors: barriers to successful application in gene therapy. *Curr. Opin. Struct. Biol.* 1: 147-157 (1999).

Singh, Transferrin as a targeting ligand for liposomes and anticancer drugs. *Curr Pharm Des.* 1999 June; 5(6):443-51.

Siould, "Therapeutic siRNAs," *Trends in Pharmacological Sciences,* 25(1): 22-28 (2004).

Soghomonyan, S. A., Doubrovin, M., Pike, J., Luo, X., Ittensohn, M., Runyan, J. D., Balatoni, J., Finn, R., Tjuvajev, J. G., Blasberg, R., and Bermudes, D. Positron emission tomography (PET) imaging of tumor-localized *Salmonella* expressing HSV1-TK. *Cancer Gene Ther.* 12: 101-108 (2005).

Sonawane, N., Szoka, F. J. & Verkman, A. Chloride accumulation and swelling in endosomes enhances DNA transfer by polyamine-DNA polyplexes. *J. Biol. Chem.* 278: 44826-44831 (2003).

Speert et al., *J. Clin. Invest.,* 82: 872 (1988).

Spencer, "Developments in suicide genes for preclinical and clinical applications," *Current Opinion in Molecular Therapeutics* 2: 433-440 (2000).

Stein, B. S., Gowda, S. D., Lifson, J. D., Penhallow, R. C., Bensch, K. G., Engleman, E. G. pH-independent HIV entry into CD4-positive T cells via virus envelope fusion to the plasma membrane, *Cell* 49: 659-668 (1987)

Stockert. The asialoglycoprotein receptor: relationships between structure, function, and expression. *Physiol Rev.* 1995 July; 75(3):591-609.

Swanson, J. A. & Watts, C. Macropinocytosis. *Trends Cell Biol.* 5: 424-428 (1995).

Swift et al., "Tissue-specific expression of the rat pancreatic elastase I gene in transgenic mice," *Cell* 38: 639 (1984).

Tabata, Y., & Ikada, Y. Macrophage phagocytosis of biodegradable microspheres composed of 1-lactic acid/glycolic acid homo- and copolymers. *J. Biomed. Mater. Res.* 22: 837-858 (1988).

Tachibana, R., Harashima, H., Ide, N., Ukitsu, S., Ohta, Y., Suzuki, N., Kikuchi, H., Shinohara, Y., Kiwada, H. Quantitative analysis of correlation between number of nuclear plasmids and gene expression activity after transfection with cationic liposomes. *Pharm. Res.* 19: 377-381 (2002).

Tao, W., South, V. J., Zhang, Y., Davide, J. P., Farrell, L., Kohl, N. E., Sepp-Lorenzino, L., Lobell, R. B. Induction of apoptosis by an inhibitor of the mitotic kinesin KSP requires both activation of the spindle assembly checkpoint and mitotic slippage. *Cancer Cell* 8: 49-59 (2005).

Theys, J., Landuyt, W., Nuyts, S., et al. Specific targeting of cytosine deaminase to solid tumors by engineered *Clostridium acetobutylicum. Cancer Gene Ther.* 8: 294-297 (2001).

Thurnher M, Wagner E, Clausen H, Mechtler K, Rusconi S, Dinter A, Birnstiel M L, Berger E G, Cotten M. Carbohydrate receptor-mediated gene transfer to human T leukaemic cells. *Glycobiology.* 1994 August; 4(4):429-35.

Todorovska, A. et al. Design and application of diabodies, triabodies and tetrabodies for cancer targeting. *J. Immunol. Methods* 248, 47-66 (2001).

Tomlinson, I. & Holliger, P. Methods for generating multivalent and bispecific antibody fragments. *Methods Enzymol.* 326, 461-479 (2000).

Vaughan, T. J. et al. Human antibodies with subnanomolar affinities isolated from a large non-immunized phage display library. *Nature Biotechnol.* 14, 309-314 (1996).

Vaughan, T. J., Osbourn, J. K. & Tempest, P. R. Human antibodies by design. *Nature Biotechnol.* 16, 535-539 (1998).

Verhoeyen, M., Milstein, C. & Winter, G. Reshaping human antibodies: grafting an antilysozyme activity. *Science* 239, 1534-1536 (1988).

Wakimoto, H., Johnson, P. R., Knipe, D. M., Chiocca, E. A. (2003) Effects of innate immunity on herpes simplex virus and its ability to kill tumor cells. *Gene Ther.* 10: 983-990 (2003).

Warren, B. A. The vascular morphology of tumors. Tumor Blood Circulation: Angiogenesis, Vascular Morphology and Blood Flow of Experimental and Human Tumors. Edited by Peterson H-I. Boca Raton, CRC Press, Inc., pp 1-48 (1979).

Wattiaux, R., Laurent, N., Wattiaux-De Coninck, S. & Jadot, M. Endosomes, lysosomes: their implication in gene transfer. *Adv. Drug Deliv. Rev.* 41: 201-208 (2000).

Weiss. S. & Chakraborty, T. Transfer of eukaryotic expression plasmids to mammalian host cells by bacterial carriers. *Curr. Opin. Biotechnol.* 12: 467-472 (2001).

Whitmore, M., Li, S., Huang, L. LPD lipopolyplex initiates a potent cytokine response and inhibits tumor growth. *Gene Ther.* 6: 1867-1875 (1999).

Whitmore, M. M., Li, S., Falo, L., Jr, Huang, L. Systemic administration of LPD prepared with CpG oligonucleotides inhibits the growth of established pulmonary metastases by stimulating innate and acquired antitumor immune responses. *Cancer Immunol. Immunother.* 50: 503-514 (2001).

Wickham, T. J., Segal, D. M., Roelvink, P. W., Carrion, M. E., Lizonova, A., Lee, G. M. & Kovesdi, I. Targeted adenovirus gene transfer to endothelial and smooth muscle cells by using bispecific antibodies. *J. Virol.* 70: 6831-6838 (1996).

Wright & Jong, *Experimental Medi.*, 163: 1245 (1986).

Wrobel, I. & Collins, D. Fusion of cationic liposomes with mammalian cells occurs after endocytosis. *Biochim. Biophys. Acta* 1235: 296-304 (1995).

Wu, et al., *Cancer Res.*, 63: 1515-19(2003).

Xu, Y. & Szoka, F. C. Mechanism of DNA release from cationic liposome/DNA complexes used in cell transfection. *Biochem. J.* 35: 5616-5623 (1996).

Yague et al., *Gene Therapy*, 11: 1170-74 (2004).

Yamada, H., Matsumoto, S., Matsumoto, T., Yamada, T., and Yamashita, U. Murine IL-2 secreting recombinant *Bacillus* Calmette-Guerin augments macrophage mediated cytotoxicity against murine bladder cancer MBT-2. *J. Urol.* 164: 526-531 (2000).

Yazawa K, Fujimori M, Amano J, Kano Y, Taniguchi S. *Bifidobacterium longum* as a delivery system for cancer gene therapy: Selective localization and growth in hypoxic tumors. *Cancer Gene Ther.* 2000; 7:269-274.

Yazawa K, Fujimori M, Nakamura T, et al. *Bifidobacterium longum* as a delivery system for cancer gene therapy of chemically induced rat mammary tumors. *Breast Cancer Res Treat.* 2001; 66:165-170.

Yazawa et al., "Current progress in suicide gene therapy for cancer," *World J. Surg.* 26: 783 (2002).

Yew, N. S., Wang, K. X., Przybylska, M., Bagley, R. G., Stedman, M., Marshall, J., Scheule, R. K., Cheng, S. H. Contribution of plasmid DNA to inflammation in the lung after administration of cationic lipid:pDNA complexes. *Hum. Gene Ther.* 10: 223-234 (1999).

Yu, Y. A., Shabahang, S., Timiryasova, T. M., et al. Visualization of tumors and metastases in live animals with bacteria and vaccinia virus encoding light-emitting proteins. *Nat. Biotechnol.* 22: 313-320 (2004).

Yuan, F., Leunig, M., Huang, S. K., Berk, D. A., Papahadjopoulos, D. & Jain, R. K. Microvascular permeability and interstitial penetration of sterically stabilized (stealth) liposomes in a human tumor xenograft. *Cancer Res.* 54, 3352-3356 (1994).

Yuan, F., Dellian, M., Fukumura, D., Leunig, M., Berk, D., Torchillin, V. & Jain, R. Vascular permeability in a human tumor xenograft: molecular size dependence and cutoff size. *Cancer Res.* 55: 3752-3756 (1995).

Yuhua, L., Kunyuan, G., Hui, C., et al. Oral cytokine gene therapy against murine tumor using attenuated *Salmonella typhimurium*. *Int. J. Cancer* 94: 438-443 (2001).

Zelphati, O. & Szoka, F. Intracellular distribution and mechanism of delivery of oligonucleotides mediated by cationic lipids. *Pharm. Res.* 13: 1367-1372 (1996).

Zelphati, O. & Szoka, F. Mechanism of oligonucleotide release from cationic liposomes. *Proc. Natl. Acad. Sci. U.S.A.* 93: 11493-11498 (1996).

Zhao, Y., Zhu, L., Lee, S., Li, L., Chang, E., Soong, N. W., Douer, D. & Anderson, W. F. Identification of the block in targeted retroviral-mediated gene transfer. *Proc. Natl. Acad. Sci. USA* 96: 4005-4010 (1999).

Zhou, X., Mantis, N., Zhang, X. R., Potoka, D. A., Watkins, S. C., and Ford, H. R. *Salmonella typhimurium* induces apoptosis in human monocyte-derived macrophages. *Microblol. Immunol.* 44: 987-995 (2000).

Ziady A G, Perales J C, Ferkol T, Gerken T, Beegen H, Perlmutter D H, Davis P B. Gene transfer into hepatoma cell lines via the serpin enzyme complex receptor. *Am J Physiol.* 1997 August; 273(2 Pt 1):G545-52.

WO 81/01145
WO 88/07378
WO 95/21191
WO 00/67776
U.S. Pat. No. 4,975,278
U.S. Pat. No. 4,987,071

We claim:

1. A composition comprising:
   (i) a plurality of intact killed bacterial cells, each killed bacterial cell of the plurality encompassing a drug,
   (ii) a bispecific ligand comprised of a first arm that carries specificity for a surface structure of a bacterial cell of (i) and a second arm that carries specificity for a non-phagocytic mammalian cell surface receptor, wherein the mammalian cell surface receptor activates receptor-mediated endocytosis of the killed bacterial cell, and
   (iii) a pharmaceutically acceptable carrier therefor;
   wherein the composition is essentially free of endotoxin.

2. The composition according to claim 1, wherein the killed bacterial cells further comprise a functional nucleic acid, wherein the functional nucleic acid is a regulatory RNA.

3. The composition according to claim 1, wherein the killed bacterial cells further comprise a functional nucleic acid, wherein the functional nucleic acid targets the transcript of a protein that contributes to drug resistance, apoptosis resistance, or neoplasticity.

4. The composition according to claim 3, wherein the functional nucleic acid is an siRNA, shRNA or miRNA that targets the transcript of a protein that contributes to drug resistance.

5. The composition according to claim 3, wherein the functional nucleic acid is an antisense molecule that targets the transcript of a protein that contributes to drug resistance.

6. The composition according to claim 3, wherein the functional nucleic acid is a ribozyme that targets the transcript of a protein that contributes to drug resistance.

7. The composition according to claim 3, wherein the functional nucleic acid targets the transcript of P-glycoprotein or MDR-3.

8. The composition according to claim 3, wherein the functional nucleic acid targets the transcript of MRP2, BCR-ABL, STI-571 resistance-associated protein, lung resistance-related protein, cyclooxygenase-2, nuclear factor kappa, XRCC 1, ERCC 1, GSTP 1, mutant β-tubulin, or a growth factor.

9. The composition according to claim 3, wherein the functional nucleic acid targets the transcript of a protein that contributes to apoptosis resistance.

10. The composition according to claim 9, wherein the functional nucleic acid targets a transcript of Bcl-2, BCI-XL, A1/BfI 1, focal adhesion kinase or p53 protein.

11. The composition according to claim 3, wherein the functional nucleic acid targets a transcript of a protein that contributes to neoplasticity.

12. The composition of claim 2, wherein the functional nucleic acid targets the transcript of a protein that contributes to resistance to the drug.

13. The composition of claim 1, wherein the bispecific ligand comprises an antibody or antibody fragment.

14. The composition of claim 1, wherein the bispecific ligand comprises polypeptide or carbohydrate.

15. The composition according to claim 1, wherein the bacterial cell surface structure is an O-polysaccharide component of a lipopolysaccharide on said killed bacterial cell surface.

16. The composition of claim 1, wherein the first arm and the second arm are monospecific.

17. The composition of claim 1, wherein the first arm and the second arm are multivalent.

18. The composition of claim 1, wherein the drug is selected from the group consisting of a chemotherapeutic agent, an immunosuppressive agent, a cytokines, a cytotoxic agent, a nucleolytic compound, and a radioactive isotope.

19. The composition of claim 18, wherein the drug is a chemotherapeutic agent.

* * * * *